United States Patent
Gold

(10) Patent No.: US 11,304,953 B2
(45) Date of Patent: Apr. 19, 2022

(54) COMBINATION THERAPY

(71) Applicant: MEI Pharma, Inc., San Diego, CA (US)

(72) Inventor: Daniel P. Gold, Del Mar, CA (US)

(73) Assignee: MEI Pharma, Inc., San Diego, CA (US)

( * ) Notice: Subject to any disclaimer, the term of this patent is extended or adjusted under 35 U.S.C. 154(b) by 0 days.

(21) Appl. No.: 16/613,638

(22) PCT Filed: May 22, 2018

(86) PCT No.: PCT/US2018/033936
§ 371 (c)(1),
(2) Date: Nov. 14, 2019

(87) PCT Pub. No.: WO2018/217787
PCT Pub. Date: Nov. 29, 2018

(65) Prior Publication Data
US 2020/0197403 A1      Jun. 25, 2020

Related U.S. Application Data

(60) Provisional application No. 62/510,204, filed on May 23, 2017, provisional application No. 62/518,359, filed on Jun. 12, 2017.

(51) Int. Cl.
| | | |
|---|---|---|
| A61K 31/5377 | (2006.01) | |
| A61P 35/04 | (2006.01) | |
| A61K 9/00 | (2006.01) | |
| C07K 16/28 | (2006.01) | |

(52) U.S. Cl.
CPC ........ *A61K 31/5377* (2013.01); *A61K 9/0019* (2013.01); *A61K 9/0053* (2013.01); *A61P 35/04* (2018.01); *C07K 16/2827* (2013.01)

(58) Field of Classification Search
CPC ............................. A61K 31/5377; A61P 35/00
See application file for complete search history.

(56) References Cited

U.S. PATENT DOCUMENTS

| | | | |
|---|---|---|---|
| 5,597,854 A | 1/1997 | Birbaum et al. | |
| 5,750,292 A | 5/1998 | Sato et al. | |
| 6,251,900 B1 | 6/2001 | Kawashima et al. | |
| 7,071,189 B2 | 7/2006 | Kawashima et al. | |
| 7,153,853 B2 | 12/2006 | Kawashima et al. | |
| 7,307,077 B2 | 12/2007 | Kawashima et al. | |
| 7,745,485 B2 | 6/2010 | Durden | |
| 8,486,939 B2 | 7/2013 | Rewcastle et al. | |
| 8,912,180 B2 | 12/2014 | Takahashi et al. | |
| 9,056,852 B2 | 6/2015 | Brown et al. | |
| 9,499,474 B2 | 11/2016 | Kaufhold et al. | |
| 10,064,868 B2 | 9/2018 | Brown et al. | |
| 10,335,415 B2 | 7/2019 | Brown et al. | |
| 10,603,324 B2 | 3/2020 | Brown et al. | |
| 2004/0002424 A1 | 1/2004 | Minn et al. | |
| 2007/0244110 A1 | 10/2007 | Yaguchi et al. | |
| 2008/0113987 A1 | 5/2008 | Haruta et al. | |
| 2008/0221103 A1 | 9/2008 | Sharma et al. | |
| 2008/0287431 A1 | 11/2008 | Kawashima et al. | |
| 2009/0181963 A1 | 7/2009 | Dehnhardt et al. | |
| 2009/0192176 A1 | 7/2009 | Zask et al. | |
| 2009/0233926 A1 | 9/2009 | Butterworth et al. | |
| 2009/0270390 A1 | 10/2009 | Butterworth et al. | |
| 2009/0312319 A1 | 12/2009 | Ren et al. | |
| 2009/0325954 A1 | 12/2009 | Butterworth et al. | |
| 2010/0022534 A1 | 1/2010 | Butterworth et al. | |
| 2010/0202963 A1 | 8/2010 | Gallatin et al. | |
| 2011/0009405 A1 | 1/2011 | Rewcastle et al. | |
| 2012/0165309 A1 | 6/2012 | Takahashi et al. | |
| 2012/0252802 A1 | 10/2012 | Brown et al. | |
| 2013/0150364 A1 | 6/2013 | Takahashi et al. | |
| 2014/0079686 A1 | 3/2014 | Barman et al. | |
| 2014/0088102 A1 | 3/2014 | Brown et al. | |
| 2014/0088103 A1 | 3/2014 | Brown et al. | |
| 2015/0265625 A1 | 9/2015 | Brown et al. | |
| 2016/0193211 A1 | 7/2016 | Lavitrano et al. | |
| 2017/0136014 A1 | 5/2017 | Hamdy et al. | |
| 2017/0231995 A1 | 8/2017 | Hamdy et al. | |
| 2017/0266191 A1 | 9/2017 | Hamdy et al. | |
| 2017/0349594 A1 | 12/2017 | Kim et al. | |
| 2020/0222415 A1 | 7/2020 | Gold | |
| 2021/0000838 A1 | 1/2021 | Gold | |
| 2021/0196725 A1 | 7/2021 | Gold | |

FOREIGN PATENT DOCUMENTS

| | | |
|---|---|---|
| CA | 2808435 A1 | 2/2012 |
| EP | 0711804 A2 | 5/1996 |
| EP | 1020462 A1 | 7/2000 |

(Continued)

OTHER PUBLICATIONS

Mahoney et al., Clinical Therapeutics,2015, 37(4):764-782.*
Davis et al.: Anti-PD-L1 Efficacy Can Be Enhanced by Inhibition of Myeloid-Derived Suppressor Cells with a Selective Inhibitor of PI3K[delta]/[gamma]. Cancer Research. 77(10):2607-2619 (2017).
De Henau et al.: Overcoming resistance to checkpoint blockade therapy by targeting PI3K[gamma] in myeloid cells. Nature. 539(7629):443-447 (2016).
Lichtman: Battling the Hematological Malignancies: The 200 Years' War. The Oncologist. 13:126-138(2008).
Liu et al.: Copanlisib in combination with ANTI-PD-1 induces regression in animal tumor models insensitive or resistant to the monotherapies of PI3K and checkpoint inhibitors. Internet Citation. https://onlinelibrary.wiley.com/doi/full/10.1002/hon.2438_123 (2017).

(Continued)

*Primary Examiner* — Rei Tsang Shiao
(74) *Attorney, Agent, or Firm* — Wilson Sonsini Goodrich & Rosati

(57) ABSTRACT

Provided herein are methods of treating diseases, such as cancer, using a combination therapy. In certain embodiments, the methods comprise administering an effective amount of a phosphoinositide-3-kinase (PI3K) inhibitor and an effective amount of a PD-1 or PD-L1 inhibitor to a patient.

19 Claims, 3 Drawing Sheets

(56) References Cited

FOREIGN PATENT DOCUMENTS

| | | |
|---|---|---|
| EP | 1389617 A1 | 2/2004 |
| EP | 1864665 A1 | 12/2007 |
| EP | 2050749 A1 | 4/2009 |
| EP | 2397479 A1 | 12/2011 |
| JP | H11174638 A | 7/1999 |
| TW | 201105662 A | 2/2011 |
| WO | WO-9905138 A1 | 2/1999 |
| WO | WO-02088112 A1 | 11/2002 |
| WO | WO-03077921 A1 | 9/2003 |
| WO | WO-03078423 A1 | 9/2003 |
| WO | WO-03078426 A1 | 9/2003 |
| WO | WO-03078427 A1 | 9/2003 |
| WO | WO-03097862 A1 | 11/2003 |
| WO | WO-2004037812 A1 | 5/2004 |
| WO | WO-2004048365 A1 | 6/2004 |
| WO | WO-2005028467 A1 | 3/2005 |
| WO | WO-2005066156 A1 | 7/2005 |
| WO | WO-2005095389 A1 | 10/2005 |
| WO | WO-2006021881 A2 | 3/2006 |
| WO | WO-2006053109 A1 | 5/2006 |
| WO | WO-2006053227 A2 | 5/2006 |
| WO | WO-2006095906 A1 | 9/2006 |
| WO | WO-2007066099 A1 | 6/2007 |
| WO | WO-2007066103 A1 | 6/2007 |
| WO | WO-2007084786 A1 | 7/2007 |
| WO | WO-2007127175 A2 | 11/2007 |
| WO | WO-2007127183 A1 | 11/2007 |
| WO | WO-2008018426 A1 | 2/2008 |
| WO | WO-2008032027 A1 | 3/2008 |
| WO | WO-2008032028 A1 | 3/2008 |
| WO | WO-2008032033 A1 | 3/2008 |
| WO | WO-2008032036 A1 | 3/2008 |
| WO | WO-2008032041 A1 | 3/2008 |
| WO | WO-2008032060 A1 | 3/2008 |
| WO | WO-2008032064 A1 | 3/2008 |
| WO | WO-2008032072 A1 | 3/2008 |
| WO | WO-2008032077 A1 | 3/2008 |
| WO | WO-2008032086 A1 | 3/2008 |
| WO | WO-2008032089 A1 | 3/2008 |
| WO | WO-2008032091 A1 | 3/2008 |
| WO | WO-2008098058 A1 | 8/2008 |
| WO | WO-2008115974 A2 | 9/2008 |
| WO | WO-2008116129 A2 | 9/2008 |
| WO | WO-2008154026 A1 | 12/2008 |
| WO | WO-2009007751 A2 | 1/2009 |
| WO | WO-2009045174 A1 | 4/2009 |
| WO | WO-2009045175 A1 | 4/2009 |
| WO | WO-2009066775 A1 | 5/2009 |
| WO | WO-2009093981 A1 | 7/2009 |
| WO | WO-2009097490 A1 | 8/2009 |
| WO | WO-2009099163 A1 | 8/2009 |
| WO | WO-2009120094 A2 | 10/2009 |
| WO | WO-2009143313 A1 | 11/2009 |
| WO | WO-2009143317 A1 | 11/2009 |
| WO | WO-2009157880 A1 | 12/2009 |
| WO | WO-2010005558 A2 | 1/2010 |
| WO | WO-2010048149 A1 | 4/2010 |
| WO | WO-2010052569 A2 | 5/2010 |
| WO | WO-2010092962 A1 | 8/2010 |
| WO | WO-2010110685 A2 | 9/2010 |
| WO | WO-2010110686 A1 | 9/2010 |
| WO | WO-2010136491 A1 | 12/2010 |
| WO | WO-2010138589 A1 | 12/2010 |
| WO | WO-2010151735 A2 | 12/2010 |
| WO | WO-2010151737 A2 | 12/2010 |
| WO | WO-2010151740 A2 | 12/2010 |
| WO | WO-2010151791 A1 | 12/2010 |
| WO | WO-2011005119 A1 | 1/2011 |
| WO | WO-2012020762 A1 | 2/2012 |
| WO | WO-2012129562 A2 | 9/2012 |
| WO | WO2012135160 | * 10/2012 |
| WO | WO-2012135160 A1 | 10/2012 |
| WO | WO-2012135166 A1 | 10/2012 |
| WO | WO-2012135175 A1 | 10/2012 |
| WO | WO-2012178123 A1 | 12/2012 |
| WO | WO-2012178124 A1 | 12/2012 |
| WO | WO-2012178125 A1 | 12/2012 |
| WO | WO-2013006408 A1 | 1/2013 |
| WO | WO-2013068075 A1 | 5/2013 |
| WO | WO-2014025960 A1 | 2/2014 |
| WO | WO-2014055647 A1 | 4/2014 |
| WO | WO-2014141129 A2 | 9/2014 |
| WO | WO-2015015013 A1 | 2/2015 |
| WO | WO-2015083008 A1 | 6/2015 |
| WO | WO-2015125085 A1 | 8/2015 |
| WO | WO-2016010879 A1 | 1/2016 |
| WO | WO-2016024228 A1 | 2/2016 |
| WO | WO-2016049214 A1 | 3/2016 |
| WO | WO-2016105118 A2 | 6/2016 |
| WO | WO-2017015267 A1 | 1/2017 |
| WO | WO-2017035234 A1 | 3/2017 |
| WO | WO-2017059224 A2 | 4/2017 |
| WO | WO-2017066705 A1 | 4/2017 |
| WO | WO-2018017708 A1 | 1/2018 |
| WO | WO-2018060833 A1 | 4/2018 |
| WO | WO-2020036997 A1 | 2/2020 |
| WO | WO-2020036999 A1 | 2/2020 |
| WO | WO-2020132563 A1 | 6/2020 |

OTHER PUBLICATIONS

Peng et al.: Loss of PTEN Promotes Resistance to T Cell-Mediated Immunotherapy. Cancer Discovery. 6(2):202-216 (2016).
Rodgers et al.: Targeting the B-cell receptor pathway: a review of current and future therapies for non-Hodgkin's lymphoma. Expert Opinion on Emerging Drugs. 23(2):111-122 (2018).
Sai et al.: Pl3K Inhibition Reduces Mammary Tumor Growth and Facilitates Antitumor Immunity and Anti-PD1 Responses. Clinical Cancer Research. 23(13):3371-3384.
Shayan et al.: Adaptive resistance to anti-PD1 therapy by Tim-3 upregulation is mediated by the Pl3K-Akt pathway in head and neck cancer. ONCOIMMUNOLOGY. 6(1):1-11 (2016).
U.S. Appl. No. 16/334,303 Final Office Action dated Nov. 3, 2020.
U.S. Appl. No. 16/334,303 Office Action dated Apr. 29, 2020.
U.S. Appl. No. 16/789,954 Office Action dated Dec. 22, 2020.
Bedingfield et al.: Structure activity relationships for a series of phenylglyceine derivatives acting at mGluRs, British Journal of Pharmacology, 1995, 116:3323-3329.
Byrn et al.: Chapter II: Hydrates and Solvates. Solid-State Chemistry of Drugs, 2nd edition pp. 233-248 (1999).
Golub et al.: Molecular classification of cancer: Class discovery and class prediction by gene expression monitoring. Science, 286:531-537, 1999.
Gross et al.: Design and synthesis of tricyclic corticotropin-releasing factor-1 antagonists, J. Med Chem. 2005, 48:5780-5793.
Homer et al.: Derivate des Chinoxalins als Isostere der Pteridine, Justus Liebigs Annalen der Chemie 1953, 579:212-234.
International Application No. PCT/US2017/052086 International Preliminary Report on Patentability dated Mar. 19, 2019.
International Application No. PCT/US2019/023172 International Search Report and Written Opinion dated Jun. 6, 2019.
Jaworska and Nikolova: SAR applicability domain. Review of methods for assessing the applicability domains of SARS and QSARS. Paper 4: SAR applicability domain. 9 pages, 2004.
Lala and Orucevic: Role of nitric oxide in tumor progression: Lessons from experimental tumors. Cancer and Metastasis Reviews, 17(1):91-106, 1998.
Liew et al.: SVM model for virtual screening of Lck inhibitors, J. Chem. Inf. Model. 2009, 49:877-885.
Maira et al.: Identification and characterization of NVP-BEZ235, a new orally available dual phosphatidylinositol 3-kinase/mammalian target of rapamycin inhibitor with potent in vivo antitumor activity, Mol. Cancer Ther. 2008, 7:1851-1863.
Matsuno et al.: Synthesis and antitumor activity of benzimidazolyl-1,3,5-triazine and benzimidazolylpyrimidine derivatives, Chem. Pharm. Bull. 2000, 48:1778-1781.
PCT/JP2011/068169 International Search Report dated Aug. 26, 2011 (w/English translation).

(56) References Cited

OTHER PUBLICATIONS

PCT/US2012/030653 International Search Report dated Jul. 5, 2012.
PCT/US2012/030664 International Search Report dated Jul. 5, 2012.
PCT/US2013/063067 International Search Report dated Dec. 6, 2013.
PCT/US2018/033936 International Search Report and Written Opinion dated Sep. 17, 2018.
PCT/US2019/046408 International Search Report and Written Opinion dated Oct. 24, 2019.
PCT/US2019/046411 International Search Report and Written Opinion dated Oct. 29, 2019.
Provencal et al.: Development of an efficient and scalable process of a respiratory syncytial virus inhibitor, Org. Proc. Res. Dev. 2004, 8: 903-908.
Pryde et al.: Novel selective inhibitors of neutral endopeptidase for the treatment of female sexual arousal disorder. Synthesis and activity of functionalized glutaramides, J. Med. Chem. 2006, 49:4409-4424.
PUBCHEM-SID: 340590222; pp. 1-4; p. 2; Aug. 23, 2017 (https://pubchem.ncbi.nlm.nih.gov/substance/340590222).
Sabat et al.: The development of 2-benzimidazole substituted pyrimidine based inhibitors of lymphocyte specific kinase (Lck), Bioorg. Med. Che. Lett. 2006, 16:5973-5977.
U.S. Appl. No. 14/729,700 Office Action dated Feb. 7, 2017.
U.S. Appl. No. 14/729,700 Office Action dated Oct. 17, 2017.
U.S. Appl. No. 16/389,371 Notice of Allowance dated Nov. 15, 2019.
Volinia et al.: Molecular cloning, cDNA sequence, and chromosomal localization of the human phosphatidylinositol 3-kinase p110 alpha (PIK3CA) gene, Genomics 1994, 24:472-477.
Voskoglou-Nomikos et al.: Clinical predictive value of the in Vitro cell line, human xenograft, and mouse allograft preclinical cancer models. Clinical Cancer Research, 9:4227-4239, 2003.
Wipf et al.: Synthesis and biological evaluation of synthetic viridins derived from C(20)-heteroalkylation of the steroidal Pl-3-kinase inhibitor wortmannin, Org. Biomol. Chem., 2004, 2:1911-1920.
Zask et al.: Synthesis and structure-activity relationships of ring-opened 17-hydroxywortmannins: potent phosphoinositide 3-kinase inhibitors with improved properties and anticancer efficacy, J. Med. Chem., 2008, 51:1319-1323.
Zhu et al.: Pegylated wortmannin and 17-hydroxywortmannin conjugates as phosphoinositide 3-kinase inhibitors active in human tumor xenograft models, J. Med. Chem., 2006, 49:1373-1378.
De Vos et al.: Combinations of idelalisib with rituximab and/or bendamustine in patients with recurrent indolent non-Hodgkin lymphoma. Blood Advances. 1(2):122-131 (2016).
MEI Pharma et al.: MEI Pharma Presents Updated Clinical Data from the ME-401 Monotherapy and in Combination with Rituximab Phase 1b study in Patients with Follicular Lymphoma at the 2019 American Society of Clinical Oncology (ASCO) Annual Meeting. 2019.
O'Farrell: Preclinical Characterization of PWT143, a Novel Selective and potent Phosphatidylinositol 3-kinase Delta (Pl3K delta) Inhibitor with Ex-Vivo Activity in Hematologic Malignancies. Blood. American Society of Hematoloty. Title; Abstract (2012).
PCT/US2019/046411 International Preliminary Report on Patentability dated Feb. 25, 2021.
Salles et al.: Efficacy and safety of idelalisib in patients with relapsed, rituximab-and alkylating agent-refractory follicular lympohoma: a subgroup analysis of a phase 2 study. Haematologica. 102:3158 (2017).
U.S. Appl. No. 16/334,303 Restriction Requirement dated Dec. 5, 2019.
U.S. Appl. No. 16/789,954 Final Office Action dated Sep. 27, 2021.

\* cited by examiner

COMBINATION THERAPY

CROSS-REFERENCE TO RELATED APPLICATIONS

This application is a national stage entry of PCT/US2018/033936, filed on May 22, 2018, and claims benefit of U.S. patent application Ser. No. 62/510,204, filed on May 23, 2017, and U.S. patent application Ser. No. 62/518,359, filed on Jun. 12, 2017, which are all hereby incorporated by reference in their entirety.

BACKGROUND OF THE INVENTION

Phosphoinositide-3-kinases (PI3Ks) play a variety of roles in normal tissue physiology (Foukas & Shepherd, *Biochem. Soc. Trans.* 2004, 32, 330; Shepherd, *Acta Physiol. Scand.* 2005, 183, 3), with p110α having a specific role in cancer growth, p110β in thrombus formation mediated by integrin $\alpha_{IIb}\beta_3$ (Jackson et al., *Nat. Med.* 2005, 11, 507), and p110γ, in inflammation, rheumatoid arthritis, and other chronic inflammation states (Barber et al., *Nat. Med.* 2005, 11, 933; Camps et al., *Nat. Med.* 2005, 11, 936; Rommel et al., *Nat. Rev.* 2007, 7, 191; and Ito, et al., *J. Pharm. Exp. Therap.* 2007, 321, 1). Inhibitors of PI3Ks have therapeutic potential in the treatment of various proliferative diseases, including cancer.

SUMMARY OF THE DISCLOSURE INVENTION

Disclosed herein is a method for treating or preventing a disease comprising administering:
(i) an effective amount of a compound of Formula (I):

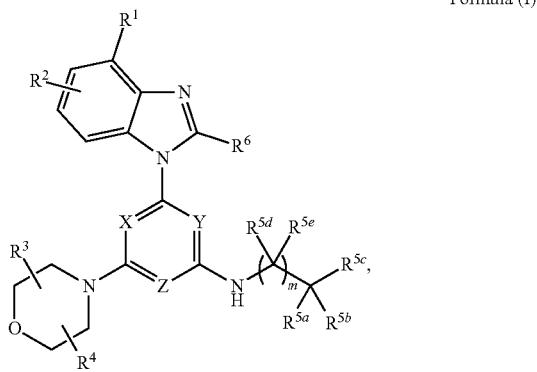

Formula (I)

or an enantiomer, a mixture of enantiomers, a mixture of two or more diastereomers, or an isotopic variant thereof; or a pharmaceutically acceptable salt, solvate, hydrate, or prodrug thereof; wherein:

X, Y, and Z are each independently N or $CR^X$, with the proviso that at least two of X, Y, and Z are nitrogen atoms; where $R^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $—C(O)R^{1a}$, $—C(O)OR^{1a}$, $—C(O)NR^{1b}R^{1c}$, $—C(NR^{1a})NR^{1b}R^{1c}$, $—OC(O)R^{1a}$, $—OC(O)OR^{1a}$, $—OC(O)NR^{1b}R^{1c}$, $—OC(=NR^{1a})NR^{1b}R^{1c}$, $—OS(O)R^{1a}$, $—OS(O)_2R^{1a}$, $—OS(O)NR^{1b}R^{1c}$, $—OS(O)_2NR^{1b}R^{1c}$, $—NR^{1b}R^{1c}$, $—NR^{1a}C(O)R^{1d}$, $—NR^{1a}C(O)OR^{1d}$, $—NR^{1a}C(O)NR^{1b}R^{1c}$, $—NR^{1a}C(=NR^{1d})NR^{1b}R^{1c}$, $—NR^{1a}S(O)R^{1d}$, $—NR^{1a}S(O)_2R^{1d}$, $—NR^{1a}S(O)NR^{1b}R^{1c}$, $—NR^{1a}S(O)_2NR^{1b}R^{1c}$, $—S(O)R^{1a}$, $—S(O)_2R^{1a}$, $—S(O)NR^{1b}R^{1c}$, or $—S(O)_2NR^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $—C(O)R^{1a}$, $—C(O)OR^{1a}$, $—C(O)NR^{1b}R^{1c}$, $—C(NR^{1a})NR^{1b}R^{1c}$, $—OC(O)R^{1a}$, $—OC(O)OR^{1a}$, $—OC(O)NR^{1b}R^{1c}$, $—OC(=NR^{1a})NR^{1b}R^{1c}$, $—OS(O)R^{1a}$, $—OS(O)_2R^{1a}$, $—OS(O)NR^{1b}R^{1c}$, $—OS(O)_2NR^{1b}R^{1c}$, $—NR^{1b}R^{1c}$, $—NR^{1a}C(O)R^{1d}$, $—NR^{1a}C(O)OR^{1d}$, $—NR^{1a}C(O)NR^{1b}R^{1c}$, $—NR^{1a}C(=NR^{1d})NR^{1b}R^{1c}$, $—NR^{1a}S(O)R^{1d}$, $—NR^{1a}S(O)_2R^{1d}$, $—NR^{1a}S(O)NR^{1b}R^{1c}$, $—NR^{1a}S(O)_2NR^{1b}R^{1c}$, $—S(O)R^{1a}$, $—S(O)_2R^{1a}$, $—S(O)NR^{1b}R^{1c}$, or $—S(O)_2NR^{1b}R^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $—C(O)R^{1a}$, $—C(O)OR^{1a}$, $—C(O)NR^{1b}R^{1c}$, $—C(NR^{1a})NR^{1b}R^{1c}$, $—OR^{1a}$, $—OC(O)R^{1a}$, $—OC(O)OR^{1a}$, $—OC(O)NR^{1b}R^{1c}$, $—OC(=NR^{1a})NR^{1b}R^{1c}$, $—OS(O)R^{1a}$, $—OS(O)_2R^{1a}$, $—OS(O)NR^{1b}R^{1c}$, $—OS(O)_2NR^{1b}R^{1c}$, $—NR^{1b}R^{1c}$, $—NR^{1a}C(O)R^{1d}$, $—NR^{1a}C(O)OR^{1d}$, $—NR^{1a}C(O)NR^{1b}R^{1c}$, $—NR^{1a}C(=NR^{1d})NR^{1b}R^{1c}$, $—NR^{1a}S(O)R^{1d}$, $—NR^{1a}S(O)_2R^{1d}$, $—NR^{1a}S(O)NR^{1b}R^{1c}$, $—NR^{1a}S(O)_2NR^{1b}R^{1c}$, $—SR^{1a}$, $—S(O)R^{1a}$, $—S(O)_2R^{1a}$, $—S(O)NR^{1b}R^{1c}$, or $—S(O)_2NR^{1b}R^{1c}$;

$R^{5c}$ is $—(CR^{5f}R^{5g})_n—(C_{6-14}$ aryl) or $—(CR^{5f}R^{5g})_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $—C(O)R^{1a}$, $—C(O)OR^{1a}$, $—C(O)NR^{1b}R^{1c}$, $—C(NR^{1a})NR^{1b}R^{1c}$, $—OC(O)R^{1a}$, $—OC(O)OR^{1a}$, $—OC(O)NR^{1b}R^{1c}$, $—OC(=NR^{1a})NR^{1b}R^{1c}$, $—OS(O)R^{1a}$, $—OS(O)_2R^{1a}$, $—OS(O)NR^{1b}R^{1c}$, $—OS(O)_2NR^{1b}R^{1c}$, $—NR^{1b}R^{1c}$, $—NR^{1a}C(O)R^{1d}$, $—NR^{1a}C(O)OR^{1d}$, $—NR^{1a}C(C)NR^{1b}R^{1c}$, $—NR^{1a}C(=NR^{1d})NR^{1b}R^{1c}$, $—NR^{1a}S(O)R^{1d}$, $—NR^{1a}S(O)_2R^{1d}$, $—NR^{1a}S(C)NR^{1b}R^{1c}$, $—NR^{1a}S(O)_2NR^{1b}R^{1c}$, $—SR^{1a}$, $—S(O)R^{1a}$, $—S(O)_2R^{1a}$, $—S(C)NR^{1b}R^{1c}$, or $—S(O)_2NR^{1b}R^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $—C(O)R^{1a}$, $—C(O)OR^{1a}$, $—C(O)NR^{1b}R^{1c}$, $—C(NR^{1a})NR^{1b}R^{1c}$, $—OC(O)R^{1a}$, $—OC(O)OR^{1a}$, $—OC(O)NR^{1b}R^{1c}$, $—OC(=NR^{1a})NR^{1b}R^{1c}$, $—OS(O)R^{1a}$, $—OS(O)_2R^{1a}$, $—OS(O)NR^{1b}R^{1c}$, $—OS(O)_2NR^{1b}R^{1c}$, $—NR^{1b}R^{1c}$, $—NR^{1a}C(O)R^{1d}$, $—NR^{1a}C(O)OR^{1d}$, $—NR^{1a}C(C)NR^{1b}R^{1c}$, $—NR^{1a}C(=NR^{1d})NR^{1b}R^{1c}$, $—NR^{1a}S(O)R^{1d}$, $—NR^{1a}S(O)_2R^{1d}$, $—NR^{1a}S(O)NR^{1b}R^{1c}$, $—NR^{1a}S(O)_2NR^{1b}R^{1c}$, $—SR^{1a}$, $—S(O)R^{1a}$, $—S(O)_2R^{1a}$, $—S(C)NR^{1b}R^{1c}$; or $—S(O)_2NR^{1b}R^{1c}$; or (d) when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl or heterocyclyl;

$R^6$ is hydrogen, $C_{1-6}$ alkyl, —S—$C_{1-6}$ alkyl, —S(O)—$C_{1-6}$ alkyl, or —SO$_2$—$C_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl in $R^1$, $R^2$, $R^3$, $R^4$, $R^6$, $R^X$, $R^{1a}$, $R^{1b}$, $R^{1c}$, $R^{1d}$, $R^{5a}$, $R^{5b}$, $R^{5c}$, $R^{5d}$, $R^{5e}$, $R^{5f}$, and $R^{5g}$ is optionally substituted with one, two, three, four, or five substituents Q, wherein each substituent Q is independently selected from (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one, two, three, or four substituents $Q^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)N$R^bR^c$, —N$R^a$S(O)$R^d$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is further optionally substituted with one, two, three, or four substituents $Q^a$; or (iii) $R^b$ and $R^c$ together with the N atom to which they are attached form heterocyclyl, which is further optionally substituted with one, two, three, or four substituents $Q^a$;

wherein each $Q^a$ is independently selected from the group consisting of (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl; or wherein two substituents Q that are adjacent to each other optionally form a $C_{3-10}$ cycloalkenyl, $C_{6-14}$ aryl, heteroaryl, or heterocyclyl, each optionally substituted with one, two, three, or four substituents $Q^a$; and (ii) an effective amount of a PD-1 inhibitor or PD-L1 inhibitor to a patient.

In some embodiments, $R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, or heteroaryl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —S(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$.

In some embodiments, $R^{5a}$ and $R^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$.

In some embodiments, $R^{5a}$ and $R^{5b}$ are each methyl, optionally substituted with one, two or three halo(s). In some embodiments, n is 1. In some embodiments, n is 1 and $R^{5f}$ and $R^{5g}$ are each hydrogen. In some embodiments, n is 0. In some embodiments, m is 0.

In some embodiments, the compound of Formula (I) is of Formula (XI):

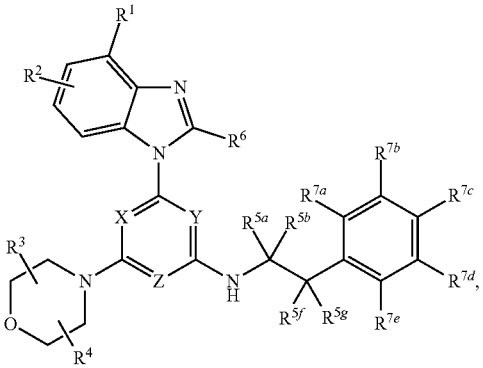

Formula (XI)

or an enantiomer, a mixture of enantiomers, a mixture of two or more diastereomers, or an isotopic variant thereof; or a pharmaceutically acceptable salt, solvate, hydrate, or prodrug thereof; wherein:

$R^{7a}$, $R^{7b}$, $R^{7c}$, $R^{7d}$, and $R^{7e}$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one, two, three, or four substituents $Q^a$; or (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, or —S(O)$_2$N$R^bR^c$; or two of $R^{7a}$, $R^{7b}$, $R^{7c}$, $R^{7d}$, and $R^{7e}$ that are adjacent to each other form a $C_{3-10}$ cycloalkenyl, $C_{6-14}$ aryl, heteroaryl, or heterocyclyl, each optionally substituted with one, two, three, or four substituents $Q^a$.

In some embodiments, the compound of Formula (I) is Compound I:

Compound I

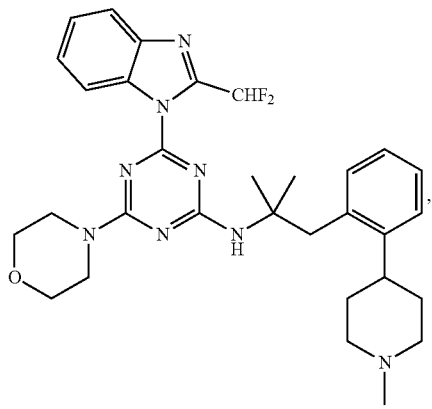

an isotopic variant thereof, a pharmaceutically acceptable salt, solvate, hydrate, or prodrug thereof.

In some embodiments, the compound of Formula (I) is Compound II:

Compound II

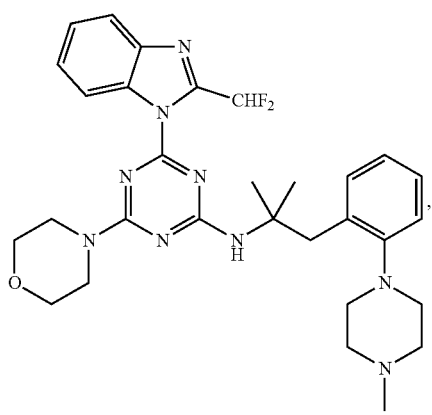

an isotopic variant thereof, a pharmaceutically acceptable salt, solvate, hydrate, or prodrug thereof.

In some embodiments, the compound of Formula (I) is Compound III:

Compound III

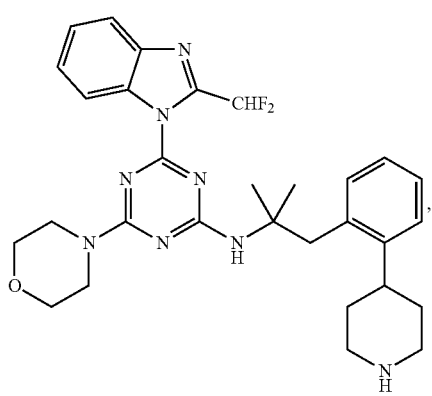

an isotopic variant thereof, a pharmaceutically acceptable salt, solvate, hydrate, or prodrug thereof.

In some embodiments, the compound of Formula (I) is Compound IV:

Compound IV

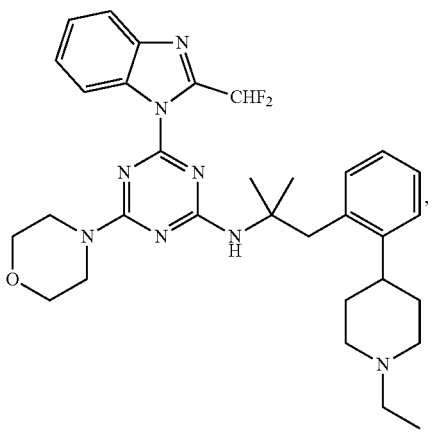

an isotopic variant thereof, a pharmaceutically acceptable salt, solvate, hydrate, or prodrug thereof.

In some embodiments, the compound of Formula (I) is Compound V:

Compound V

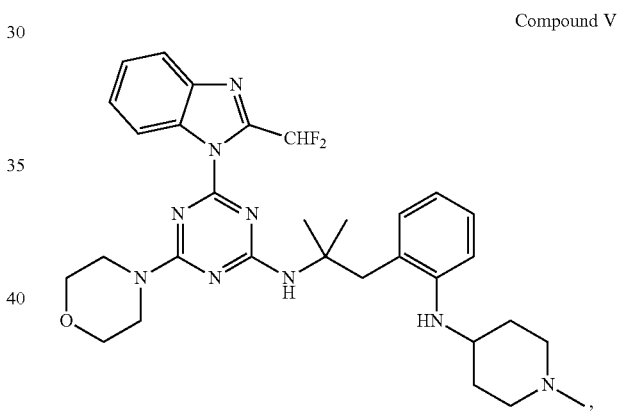

an isotopic variant thereof, a pharmaceutically acceptable salt, solvate, hydrate, or prodrug thereof.

In some embodiments, the PD-1 or PD-L1 inhibitor is pidilizumab, nivolumab, pembrolizumab, atezolizumab, avelumab, BMS-936559, durvalumab or a combination thereof. In some embodiments, the PD-1 or PD-L1 inhibitor is pidilizumab, nivolumab, pembrolizumab, atezolizumab, avelumab, BMS-936559, BGB-A317, PDR001, REGN2810, durvalumab or a combination thereof.

In some embodiments, the disease being treated is cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

DETAILED DESCRIPTION OF THE INVENTION

Figure 1:
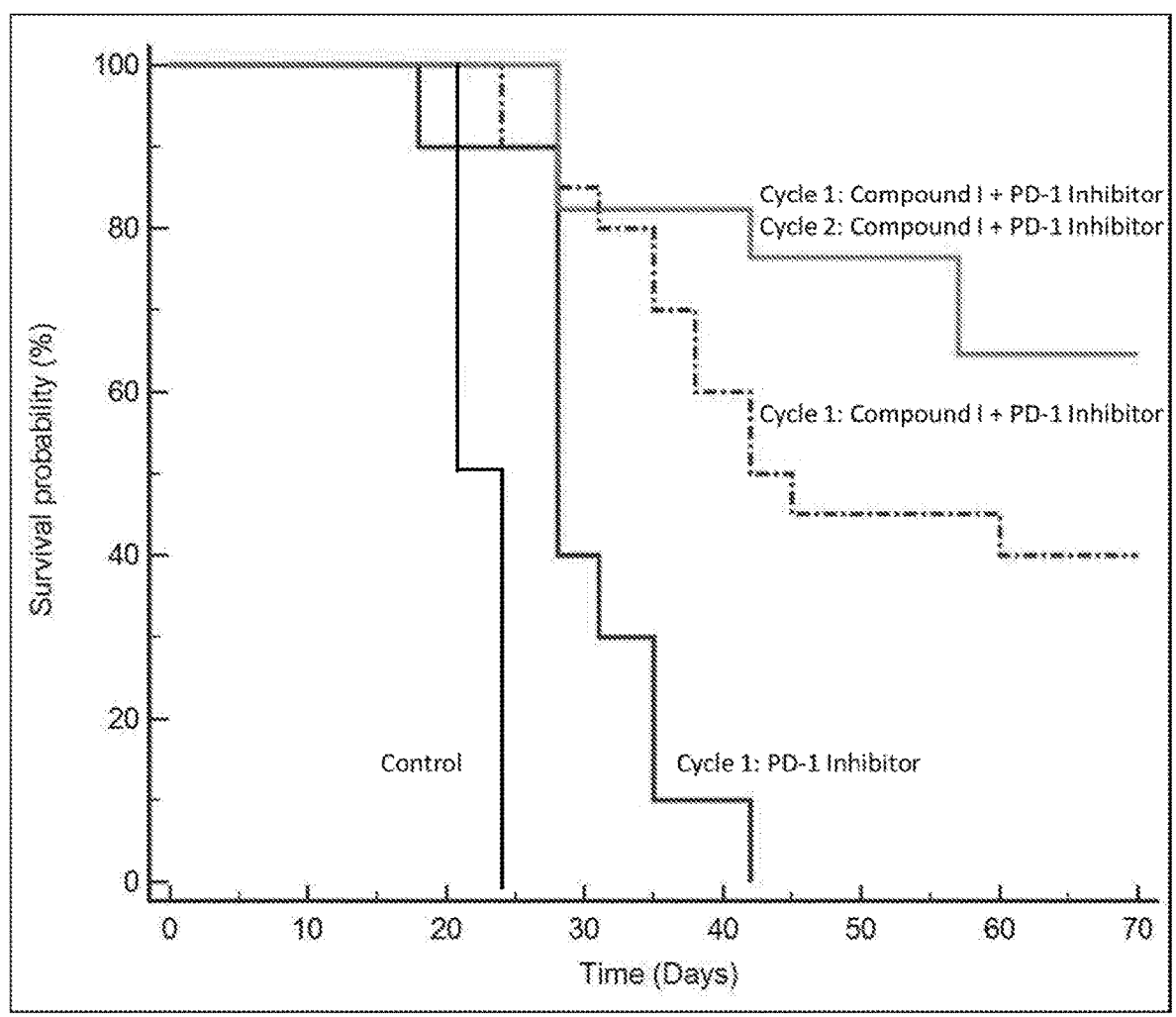
FIG. 1 illustrates the Kaplan-Meier survival curves obtained from Example 2a, wherein a study was performed evaluating the efficacy of a combination treatment of Compound I and a PD-1 inhibitor (RPM1-14), in a MC38 murine adenocarcinoma model. The figure depicts the efficacy of two cycles of the combination treatment in comparison to a single cycle of a combination treatment or a single cycle of the PD-1 inhibitor.

Described herein are pharmaceutical compositions comprising a PI3K inhibitor and a PD-1 or a PD-L1 inhibitor. In some instances, the pharmaceutical compositions described herein may be used for treating diseases or disorders associated with excessive cell proliferation, such as cancer. Also described herein are methods of treating the proliferative diseases and disorders with i) a PI3K inhibitor; and ii) a PD-1 or a PD-L1 inhibitor.

Definitions

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "therapeutically effective amount" and "effective amount" are meant to include the amount of a compound that, when administered, is sufficient to prevent development of, or alleviate to some extent, one or more of the symptoms of the disorder, disease, or condition being treated. The terms "therapeutically effective amount" or "effective amount" also refer to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The terms "pharmaceutically acceptable carrier," "pharmaceutically acceptable excipient," "physiologically acceptable carrier," and "physiologically acceptable excipient" refer to a pharmaceutically-acceptable material, composition, or vehicle, such as a liquid or solid filler, diluent, solvent, or encapsulating material. In one embodiment, each component is "pharmaceutically acceptable" in the sense of being compatible with other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, Fla., 2009.

The terms "about" and "approximately" mean an acceptable error for a particular value as determined by one of ordinary skill in the art, which depends in part on how the value is measured or determined. In certain embodiments, the terms "about" and "approximately" mean within 1, 2, 3, or 4 standard deviations. In certain embodiments, the terms "about" and "approximately" mean within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a disorder, disease, or condition.

The terms "naturally occurring" and "native" when used in connection with biological materials such as nucleic acid molecules, polypeptides, host cells, and the like, refer to materials which are found in nature and are not manipulated by man. Similarly, "non-naturally occurring" or "non-native" refers to a material that is not found in nature or that has been structurally modified or synthesized by man.

The term "PI3K" refers to a phosphoinositide 3-kinase or variant thereof, which is capable of phosphorylating the inositol ring of PI in the D-3 position. The term "PI3K variant" is intended to include proteins substantially homologous to a native PI3K, i.e., proteins having one or more naturally or non-naturally occurring amino acid deletions, insertions, or substitutions (e.g., PI3K derivatives, homologs, and fragments), as compared to the amino acid sequence of a native PI3K. The amino acid sequence of a PI3K variant is at least about 80% identical, at least about 90% identical, or at least about 95% identical to a native PI3K. Examples of PI3K include, but are not limited to, p110α, p110β, p110δ, p110γ, PI3K-C2α, PI3K-C2β, PI3K-C2γ, Vps34, mTOR, ATM, ATR, and DNA-PK. See, Fry, *Biochem. Biophys. Acta* 1994, 1226, 237-268; Vanhaesebroeck and Waterfield, *Exp. Cell. Res.* 1999, 253, 239-254; and Fry, *Breast Cancer Res.* 2001, 3, 304-312. PI3Ks are classified into at least four classes. Class I includes p110α, p110β, p110δ, and p110γ. Class II includes PI3K-C2α, PI3K-C2β, and PI3K-C2γ. Class III includes Vps34. Class IV includes mTOR, ATM, ATR, and DNA-PK. In certain embodiments, the PI3K is a Class I kinase. In certain embodiments, the PI3K is p110α, p110β, p110δ, or p110γ. In certain embodiments, the PI3K is a variant of a Class I kinase. In certain embodiments, the PI3K is a p110α mutant. Examples of p110α mutants include, but are not limited to, R38H, G106V, K111N, K227E, N345K, C420R, P539R, E542K, E545A, E545G, E545K, Q546K, Q546P, E453Q, H710P, I800L, T1025S, M10431, M1043V, H1047L, H1047R, and H1047Y (Ikenoue et al., *Cancer Res.* 2005, 65, 4562-4567; Gymnopoulos et al., *Proc. Natl. Acad Sci.*, 2007, 104, 5569-5574). In certain embodiments, the PI3K is a Class II kinase. In certain embodiments, the PI3K is PI3K-C2α, PI3K-C2β, or PI3K-C2γ. In certain embodiments, the PI3K is a Class III kinase. In certain embodiments, the PI3K is Vps34. In certain embodiments, the PI3K is a Class IV kinase. In certain embodiments, the PI3K is mTOR, ATM, ATR, or DNA-PK.

The term "PD-1" refers to programmed cell death—1 receptor or programmed cell death protein 1, also known as cluster of differentiation 279 (CD279). The PD-1 protein in humans is encoded by the PDCD1 gene. PD-1 is a cell surface receptor that plays an important role in down-regulating the immune system and promoting self tolerance by suppressing T cell inflammatory activity. PD-1 is expressed on the surface of activated T cells and guards against autoimmunity through a dual mechanism of promoting apoptosis (programmed cell death) in antigen specific T-cells in lymph nodes while simultaneously reducing apoptosis in regulatory T cells (anti-inflammatory, suppressive T cells. PD-1 inhibitors activate the immune system to attack tumors and are therefore used to treat some types of cancer.

The term "PD-L1" refers to programmed death-ligand 1 also known as cluster of differentiation 274 (CD274) or B7 homolog 1 (B7-H1). PD-L1 is a protein encoded by the CD274 gene. PD-L1 is a transmembrane protein that plays a major role in suppressing the immune system. PD-L1 binds to its receptor, PD-1 (found on activated T cells, B cells, and myeloid cells) to modulate activation or inhibition of T cell responses. PD-L1, the ligand for PD-1, is highly expressed in several cancers. Inhibition of the interaction between PD-1 and PD-L1 can enhance T-cell responses against cancer cells or tumors, and thus be useful for the treatment of cancer.

The terms "synergy," "synergism," and "synergistic" as used herein refer to a combination of therapies (e.g., use of a PI3K inhibitor of Formula (I) and a PD-1 inhibitor or PD-L1 inhibitor) that is more effective than the expected additive effects of any two or more single therapies. For example, a synergistic effect of a combination of therapies permits the use of lower dosages of one or more of the therapies and/or less frequent administration of said therapies to a subject. The ability to utilize lower dosages of therapies and/or to administer the therapies less frequently reduces the toxicity associated with the administration of the therapies to a subject without reducing the efficacy of said therapies in the prevention, management, treatment, or amelioration of a given disease, such as an autoimmune disease, inflammatory disease, or cancer including, but not limited to, chronic lymphocytic leukemia or non-Hodgkin's lymphoma. In addition, a synergistic effect can result in improved efficacy of therapies in the prevention, management, treatment, or amelioration of a given disease, such an autoimmune disease, inflammatory disease, or cancer including, but not limited to, chronic lymphocytic leukemia or non-Hodgkin's lymphoma. Finally, synergistic effects of a combination of therapies may avoid or reduce adverse or unwanted side effects associated with the use of any single therapy. The "synergy," "synergism," or "synergistic" effect of a combination may be determined herein by the methods of Chou et al., and/or Clarke et al. See Ting-Chao Chou, Theoretical Basis, Experimental Design, and Computerized Simulation of Synergism and Antagonism in Drug Combination Studies, Pharmacol Rev 58:621-681 (2006), and Clarke et al., Issues in experimental design and endpoint analysis in the study of experimental cytotoxic agents in vivo in breast cancer and other models, Breast Cancer Research and Treatment 46:255-278 (1997), which are both incorporated by reference for the methods of determining the "synergy," synergism," or "synergistic" effect of a combination.

The term "isotopic variant" refers to a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I) In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3$H), carbon-11 ($^{11}$C), carbon-14 ($^{14}$C) nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I) iodine-125 ($^{125}$I), iodine-129 ($^{129}$I), and iodine-131 ($^{131}$I). It will be understood that, in a compound as provided herein, any hydrogen can be $^2$H, for example, or any carbon can be $^{13}$C, for example, or any nitrogen can be $^{15}$N, for example, or any oxygen can be $^{18}$O, for example, where feasible according to the judgment of one of skill. In certain embodiments, an "isotopic variant" of a compound contains unnatural proportions of deuterium (D).

The term "alkyl" refers to a linear or branched saturated monovalent hydrocarbon radical, wherein the alkylene may optionally be substituted with one or more substituents Q as described herein. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkylene" refers to a linear or branched saturated divalent hydrocarbon radical, wherein the alkylene may optionally be substituted with one or more substituents Q as described herein. The term "alkylene" encompasses both linear and branched alkylene, unless otherwise specified. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms). For example, $C_{1-6}$ alkylene refers to a linear saturated divalent hydrocarbon radical of 1 to 6 carbon atoms or a branched saturated divalent hydrocarbon radical of 3 to 6 carbon atoms.

The term "heteroalkylene" refers to a linear or branched saturated divalent hydrocarbon radical that contains one or more heteroatoms each independently selected from O, S, and N in the hydrocarbon chain. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkylene groups are also referred as "lower heteroalkylene." Examples of heteroalkylene groups include, but are not limited to, —CH$_2$O—, —CH$_2$OCH$_2$—, —CH$_2$CH$_2$O—, —CH$_2$NH—, —CH$_2$NHCH$_2$—, —CH$_2$CH$_2$NH—, —CH$_2$S—, —CH$_2$SCH$_2$—, and —CH$_2$CH$_2$S—. In certain embodiments, heteroalkylene may also be optionally substituted with one or more substituents Q as described herein.

The term "alkenyl" refers to a linear or branched monovalent hydrocarbon radical, which contains one or more, in one embodiment, one, two, three, four, or five, in another embodiment, one, carbon-carbon double bond(s). The alkenyl may be optionally substituted with one or more substituents Q as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more, in one embodiment, one, two, three, four, or five, in another embodiment, one, carbon-carbon double bond(s). The alkenylene may be optionally substituted with one or more substituents Q as described herein. Similarly, the term "alkenylene" also embraces radicals having "cis" and "trans" configurations, or alternatively, "E" and "Z" configurations. As used herein, the term "alkenylene" encompasses both linear and branched alkenylene, unless otherwise specified. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene.

The term "heteroalkenylene" refers to a linear or branched divalent hydrocarbon radical, which contains one or more, in one embodiment, one, two, three, four, or five, in another embodiment, one, carbon-carbon double bond(s), and which contains one or more heteroatoms each independently selected from O, S, and N in the hydrocarbon chain. The heteroalkenylene may be optionally substituted with one or more substituents Q as described herein. The term "heteroalkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ heteroalkenylene refers to a linear unsaturated divalent hydrocarbon radical of 2 to 6 carbon atoms or a branched unsaturated divalent hydrocarbon radical of 3 to 6 carbon atoms. In certain embodiments, the heteroalkenylene is a linear divalent hydrocarbon radical of 2 to 20 ($C_{2-20}$), 2 to 15

($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of heteroalkenylene groups include, but are not limited to, —CH=CHO—, —CH=CHOCH$_2$—, —CH=CHCH$_2$O—, —CH=CHS—, —CH=CHSCH$_2$—, —CH=CHCH$_2$S—, or —CH=CHCH$_2$NH—.

The term "alkynyl" refers to a linear or branched monovalent hydrocarbon radical, which contains one or more, in one embodiment, one, two, three, four, or five, in another embodiment, one, carbon-carbon triple bond(s). The alkynyl may be optionally substituted with one or more substituents Q as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "cycloalkyl" refers to a cyclic saturated bridged and/or non-bridged monovalent hydrocarbon radical, which may be optionally substituted with one or more substituents Q as described herein. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, bicyclo[2.1.1]hexyl, bicyclo[2.2.1]heptyl, decalinyl, and adamantyl.

The term "cycloalkenyl" refers to a cyclic unsaturated, nonaromatic bridged and/or non-bridged monovalent hydrocarbon radical, which may be optionally substituted with one or more substituents Q as described herein. In certain embodiments, the cycloalkenyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclobutenyl, cyclopentenyl, cyclohexenyl, or cycloheptenyl, The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted with one or more substituents Q as described herein.

The terms "aralkyl" and "arylalkyl" refer to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, the aralkyl are optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms independently selected from O, S, N, and P in the ring. A heteroaryl group is bonded to the rest of a molecule through its aromatic ring. Each ring of a heteroaryl group can contain one or two 0 atoms, one or two S atoms, one to four N atoms, and/or one or two P atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl may also be optionally substituted with one or more substituents Q as described herein as described herein.

The terms "heterocyclyl" and "heterocyclic" refer to a monovalent monocyclic non-aromatic ring system or monovalent polycyclic ring system that contains at least one non-aromatic ring, wherein one or more of the non-aromatic ring atoms are heteroatoms independently selected from O, S, N, and P; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. A heterocyclyl group is bonded to the rest of a molecule through its non-aromatic ring. In certain embodiments, the heterocyclyl is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl may also be optionally substituted with one or more substituents Q as described herein.

The terms "halogen," "halide," and "halo" refer to fluorine, chlorine, bromine, and/or iodine.

The term "optionally substituted" is intended to mean that a group or substituent, such as an alkyl, alkylene, heteroalkylene, alkenyl, alkenylene, heteroalkenylene, alkynyl, cycloalkyl, cycloalkenyl, aryl, aralkyl, heteroaryl, heteroaryl-$C_{1-6}$ alkyl, and heterocyclyl group, may be substituted with one or more substituents Q, each of which is independently selected from, e.g., (a) oxo (=O), halo, cyano (—CN), and nitro (—NO$_2$); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, four, or five, substituents $Q^a$; and (c) —C(O)$R^a$, —C(O)O$R^a$, —C(O)N$R^b R^c$, —C(N$R^a$)N$R^b R^c$, —O$R^a$, —OC(O)$R^a$, —OC(O)O$R^a$, —OC(O)N$R^b R^c$, —OC(=N$R^a$)N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(=N$R^d$)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —P(O)$R^a R^d$, —P(O)(O$R^a$)$R^d$, —P(O)(O$R^a$)(O$R^d$), —S$R^a$, —S(O)$R^a$, —S(O)$_2 R^a$, —S(O)N$R^b R^c$, and —S(O)$_2$N$R^b R^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heteroaryl or heterocyclyl, optionally substituted with one or more, in one embodiment, one, two, three, or four, substituents $Q^a$. As used herein, all groups that can be substituted are "optionally substituted," unless otherwise specified.

In one embodiment, each substituent $Q^a$ is independently selected from the group consisting of (a) oxo, cyano, halo, and nitro; and (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^f R^g$, —C(N$R^e$)N$R^f R^g$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^h$, —N$R^e$C(O)N$R^f R^g$, —N$R^e$C(=N$R^h$)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —P(O)$R^e R^h$, —P(O)(O$R^e$)$R^h$, —P(O)(O$R^e$)(O$R^h$), —S(O)$R^e$, —S(O)$_2 R^e$, —S(O)N$R^f R^g$, and —S(O)$_2$N$R^f R^g$; wherein each $R^e$, $R^f$, $R^g$, and $R^h$ is independently (i) hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (ii) $R^f$ and $R^g$ together with the N atom to which they are attached form heteroaryl or heterocyclyl.

In certain embodiments, "optically active" and "enantiomerically pure" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The phrase "an enantiomer, a mixture of enantiomers, a mixture of two or more diastereomers, or an isotopic variant thereof; or a pharmaceutically acceptable salt, solvate, hydrate, or prodrug thereof" has the same meaning as the phrase "an enantiomer, a mixture of enantiomers, a mixture of two or more diastereomers, or an isotopic variant of the compound referenced therein; or a pharmaceutically acceptable salt, solvate, hydrate, or prodrug of the compound referenced therein; or a pharmaceutically acceptable salt, solvate, hydrate, or prodrug of an enantiomer, a mixture of enantiomers, a mixture of two or more diastereomers, or an isotopic variant of the compound referenced therein."

The term "solvate" refers to a complex or aggregate formed by one or more molecules of a solute, e.g., a compound provided herein, and one or more molecules of a solvent, which present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

Compounds

Disclosed herein are PI3K inhibitors of Formula (I):

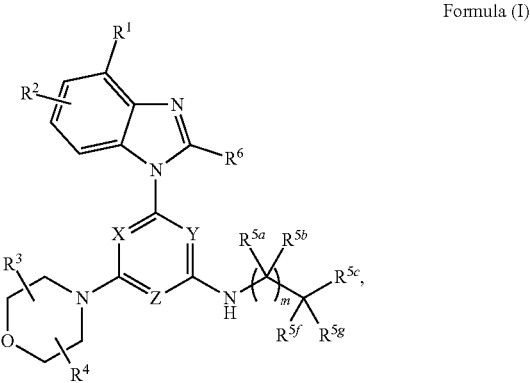

Formula (I)

or an enantiomer, a mixture of enantiomers, a mixture of two or more diastereomers, or an isotopic variant thereof; or a pharmaceutically acceptable salt, solvate, hydrate, or prodrug thereof; wherein:

X, Y, and Z are each independently N or CR$^X$, with the proviso that at least two of X, Y, and Z are nitrogen atoms; where R$^X$ is hydrogen or C$_{1-6}$ alkyl;

R$^1$ and R$^2$ are each independently (a) hydrogen, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1d}$S(O)R$^{1d}$, —NR$^{1a}$S(O)$_2$R$^{1d}$, —NR$^{1d}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(C)NR$^{1b}$R$^{1c}$, or —S(O)$_2$NR$^{1b}$R$^{1c}$, wherein each R$^{1a}$, R$^{1b}$, R$^{1c}$, and R$^{1d}$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^{1b}$ and R$^{1c}$ together with the N atom to which they are attached form heterocyclyl;

R$^3$ and R$^4$ are each independently hydrogen or C$_{1-6}$ alkyl; or R$^3$ and R$^4$ are linked together to form a bond, C$_{1-6}$ alkylene, C$_{1-6}$ heteroalkylene, C$_{2-6}$ alkenylene, or C$_{2-6}$ heteroalkenylene;

R$^{5a}$ is (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(C)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —C(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5b}$ is (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5c}$ is —(CR$^{5f}$R$^{5g}$)$_n$—(C$_{6-14}$ aryl) or —(CR$^{5f}$R$^{5g}$)$_n$-heteroaryl;

R$^{5d}$ and R$^{5e}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(C)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(C)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5f}$ and R$^{5g}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(C)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(C)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$; or —S(O)$_2$NR$^{1b}$R$^{1c}$; or (d) when one occurrence of R$^{5f}$ and one occurrence of R$^{5g}$ are attached to the same carbon atom, the R$^{5f}$ and R$^{5g}$ together with the carbon atom to which they are attached form a C$_{3-10}$ cycloalkyl or heterocyclyl;

R$^6$ is hydrogen, C$_{1-6}$ alkyl, —S—C$_{1-6}$ alkyl, —S(O)—C$_{1-6}$ alkyl, or —SO$_2$—C$_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl in R$^1$, R$^2$, R$^3$, R$^4$, R$^6$, R$^X$, R$^{1a}$, R$^{1b}$, R$^{1c}$, R$^{1d}$, R$^{5a}$, R$^{5b}$, R$^{5c}$, R$^{5d}$, R$^{5e}$, R$^{5f}$ and R$^{5g}$ is optionally substituted with one or more, in one embodiment, one, two, three, four, or five, substituents Q, wherein each substituent Q is independently selected from (a) oxo, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^e$, —OS(O)$_2$NR$^b$R$^e$, —NR$^b$R$^e$, —NR$^a$C(O)R$^d$, —NR$^a$C(O)OR$^d$, —NR$^a$C(O)NR$^b$R$^e$, —NR$^a$C(=NR$^d$)NR$^b$R$^e$, —NR$^a$S(O)R$^d$, —NR$^a$S(O)$_2$R$^d$, —NR$^a$S(O)NR$^b$R$^e$, —NR$^a$S(O)$_2$NR$^b$R$^e$, —SR$^a$, —S(O)R$^a$, —S(O)$_2$R$^a$, —S(O)NR$^b$R$^e$, and —S(O)$_2$NR$^b$R$^e$, wherein each R$^a$, R$^b$, R$^e$, and R$^d$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is further optionally substituted with one or more, in one embodiment, one, two, three, or four, substituents Q$^a$; or (iii) R$^b$ and R$^e$ together with the N atom to which they are attached form heterocyclyl, which is further optionally substituted with one or more, in one embodiment, one, two, three, or four, substituents Q$^a$;

wherein each Q$^a$ is independently selected from the group consisting of (a) oxo, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$) NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl; or wherein two substituents Q that are adjacent to each other optionally form a C$_{3-10}$ cycloalkenyl, C$_{6-14}$ aryl, heteroaryl, or heterocyclyl, each optionally substituted with one, two, three, or four substituents Q$^a$.

In one embodiment of a compound of Formula (I),

X, Y, and Z are each independently N or CR$^X$, with the proviso that at least two of X, Y, and Z are nitrogen atoms; where R$^X$ is hydrogen or C$_{1-6}$ alkyl;

R$^1$ and R$^2$ are each independently (a) hydrogen, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein each R$^{1a}$, R$^{1b}$, R$^{1c}$, and R$^{1d}$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^{1b}$ and R$^{1c}$ together with the N atom to which they are attached form heterocyclyl;

R$^3$ and R$^4$ are each independently hydrogen or C$_{1-6}$ alkyl; or R$^3$ and R$^4$ are linked together to form a bond, C$_{1-6}$ alkylene, C$_{1-6}$ heteroalkylene, C$_{2-6}$ alkenylene, or C$_{2-6}$ heteroalkenylene;

R$^{5a}$ is (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5b}$ is (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5c}$ is —(CR$^{5f}$R$^{5g}$)$_n$—(C$_{6-14}$ aryl) or —(CR$^{5f}$R$^{5g}$)$_n$-heteroaryl;

R$^{5d}$ and R$^{5e}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5f}$ and R$^{5g}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$; or —S(O)$_2$NR$^{1b}$R$^{1c}$; or (d) when one occurrence of R$^{5f}$ and one occurrence of R$^{5g}$ are attached to the same carbon atom, the R$^{5f}$ and R$^{5g}$ together with the carbon atom to which they are attached form a C$_{3-10}$ cycloalkyl or heterocyclyl;

R$^6$ is hydrogen, C$_{1-6}$ alkyl, —S—C$_{1-6}$ alkyl, —S(O)—C$_{1-6}$ alkyl, or —SO$_2$—C$_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more, in one embodiment, one, two, three, four, or five, substituents Q as defined herein.

In another embodiment of a compound of Formula (I), X, Y, and Z are each independently N or CR$^X$, with the proviso that at least two of X, Y, and Z are nitrogen atoms; where R$^X$ is hydrogen or C$_{1-6}$ alkyl;

R$^1$ and R$^2$ are each independently (a) hydrogen, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$; wherein each R$^{1a}$, R$^{1b}$, R$^{1c}$, and R$^{1d}$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^{1b}$ and R$^{1c}$ together with the N atom to which they are attached form heterocyclyl;

R$^3$ and R$^4$ are each independently hydrogen or C$_{1-6}$ alkyl; or R$^3$ and R$^4$ are linked together to form a bond, C$_{1-6}$ alkylene, C$_{1-6}$ heteroalkylene, C$_{2-6}$ alkenylene, or C$_{2-6}$ heteroalkenylene;

R$^{5a}$ is (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^1$)NR$^{1b}$R$^{1c}$, —NR$^{1a}$S(O)R$^{1d}$, —NR$^{1a}$S(O)$_2$R$^{1d}$, —NR$^{1a}$S(C)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5b}$ is (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(C)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5c}$ is —(CR$^{5f}$R$^{5g}$)$_n$—(C$_{6-14}$ aryl) or —(CR$^{5f}$R$^{5g}$)$_n$-heteroaryl;

R$^{5d}$ and R$^{5e}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$ $R^{1c}$, $-NR^{1a}C(=NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-S(O)R^{1a}$, $-S(O)_2R^{1a}$, $-S(O)NR^{1b}R^{1c}$, or $-S(O)_2NR^{1b}R^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(=NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-S(O)R^{1a}$, $-S(O)_2R^{1a}$, $-S(O)NR^{1b}R^{1c}$; or $-S(O)_2NR^{1b}R^{1c}$; or (d) when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl or heterocyclyl;

$R^6$ is hydrogen, $C_{1-6}$ alkyl, $-S-C_{1-6}$ alkyl, $-S(O)-C_{1-6}$ alkyl, or $-SO_2-C_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more, in one embodiment, one, two, three, four, or five, substituents Q as defined herein.

In yet another embodiment of a compound of Formula (I), X, Y, and Z are each independently N or $CR^X$, with the proviso that at least two of X, Y, and Z are nitrogen atoms; where $R^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(=NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-S(O)R^{1a}$, $-S(O)_2R^{1a}$, $-S(O)NR^{1b}R^{1c}$, or $-S(O)_2NR^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(=NR^1)NR^{1b}R^{1c}$, $-NR^{1a}S(O)R^{1d}$, $-NR^{1a}S(O)_2R^{1d}$, $-NR^{1a}S(C)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$, or $-S(O)_2NR^{1b}R^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(=NR^1)NR^{1b}R^{1c}$, $-NR^{1a}S(O)R^{1d}$, $-NR^{1a}S(O)_2R^{1d}$, $-NR^{1a}S(C)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$, or $-S(O)_2NR^{1b}R^{1c}$;

$R^{5c}$ is $-(CR^{5f}R^{5g})_n-(C_{6-14}$ aryl) or $-(CR^{5f}R^{5g})_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(C)NR^{1b}R^{1c}$, $-NR^{1a}C(=NR^{1d})NR^{1b}R^{1c}$, $-NR^{1a}S(O)R^{1d}$, $-NR^{1a}S(O)_2R^{1d}$, $-NR^{1a}S(C)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(C)NR^{1b}R^{1c}$, or $-S(O)_2NR^{1b}R^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1d}$, $-C(O)NR^{1b}R^{1c}$, $-C(NR^{1a})NR^{1b}R^{1c}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(=NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-S(O)R^{1a}$, $-S(O)_2R^{1a}$, $-S(O)NR^{1b}R^{1c}$; or $-S(O)_2NR^{1b}R^{1c}$; or (d) when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl or heterocyclyl;

$R^6$ is hydrogen, $C_{1-6}$ alkyl, $-S-C_{1-6}$ alkyl, $-S(O)-C_{1-6}$ alkyl, or $-SO_2-C_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more, in one embodiment, one, two, three, four, or five, substituents Q as defined herein.

In still another embodiment of a compound of Formula (I),

X, Y, and Z are N;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1d}$, $-C(O)NR^{1b}R^{1c}$, $-C(NR^{1a})NR^{1b}R^{1c}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(=NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-S(O)R^{1a}$, $-S(O)_2R^{1a}$, $-S(O)NR^{1b}R^{1c}$, or $-S(O)_2NR^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1d}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^1$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, or heteroaryl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5c}$ is —(CR$^{5f}$R$^{5g}$)$_n$—(C$_{6-14}$ aryl) or —(CR$^{5f}$R$^{5g}$)$_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5f}$ and $R^eg$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(C)NR$^{1b}$R$^{1c}$, or —S(O)$_2$NR$^{1b}$R$^{1c}$; or (d) when one occurrence of $R^{5f}$ and one occurrence of $R^eg$ are attached to the same carbon atom, the $R^{5f}$ and $R^eg$ together with the carbon atom to which they are attached form a $C_{3-10}$ cycloalkyl or heterocyclyl;

$R^6$ is hydrogen, $C_{1-6}$ alkyl, —S—$C_{1-6}$ alkyl, —S(O)—$C_{1-6}$ alkyl, or —SO$_2$—$C_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more, in one embodiment, one, two, three, four, or five, substituents Q as defined herein.

Synthesis of compounds of Formula (I) is described in U.S. Pat. No. 9,056,852 B2, which is incorporated by reference for such disclosure.

Also provided herein is a compound of Formula (IX):

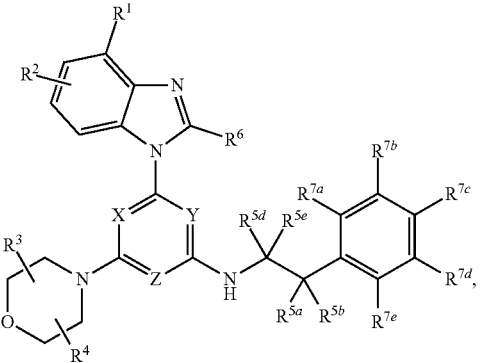

Formula (IX)

or an enantiomer, a mixture of enantiomers, a mixture of two or more diastereomers, or an isotopic variant thereof; or a pharmaceutically acceptable salt, solvate, hydrate, or prodrug thereof; wherein:

$R^{7a}$, $R^{7b}$, $R^{7c}$, $R^{7d}$, and $R^{7e}$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one, two, three, or four substituents $Q^a$; or (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, or —S(O)$_2$NR$^b$R$^c$; or two of $R^{7a}$, $R^{7b}$, $R^{7c}$, $R^{7d}$, and $R^{7e}$ that are adjacent to each other form $C_{3-10}$ cycloalkenyl, $C_{6-14}$ aryl, heteroaryl, or heterocyclyl, each optionally substituted with one, two, three, or four substituents $Q^a$; and $R^1$, $R^2$, $R^3$, $R^4$, $R^6$, $R^{1a}$, $R^{1b}$, $R^{1c}$, $R^{1d}$, $R^{5a}$, $R^{5b}$, $R^{5d}$, $R^{5e}$, X, Y, and Z are each as defined herein.

Synthesis of compounds of Formula (IX) is described in U.S. Pat. No. 9,056,852 B2, which is incorporated by reference for such disclosure.

In one embodiment, the compound of Formula (IX) has the structure of Formula (IXa):

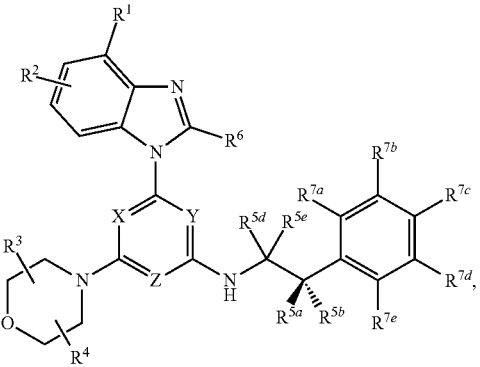

Formula (IXa)

or an isotopic variant thereof; or a pharmaceutically acceptable salt, solvate, hydrate, or prodrug thereof;

wherein $R^1$, $R^2$, $R^3$, $R^4$, $R^6$, $R^{5a}$, $R^{5b}$, $R^{5d}$, $R^{5e}$, $R^{7a}$, $R^{7b}$, $R^{7c}$, $R^{7d}$, $R^{7e}$, X, Y, and Z are each as defined herein.

Synthesis of compounds of Formula (IXa) is described in U.S. Pat. No. 9,056,852 B2, which is incorporated by reference for such disclosure.

In another embodiment, the compound of Formula (IX) has the structure of Formula (IXb):

Formula (IXb)

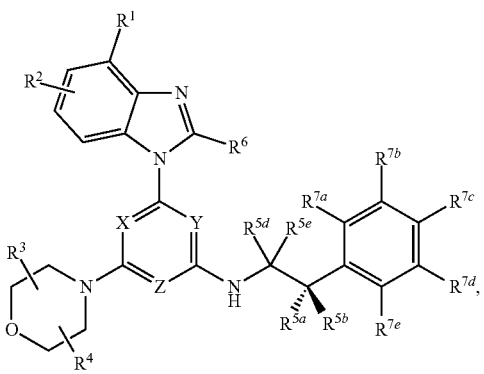

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5d}$, $R^{5e}$, $R^{7a}$, $R^{7b}$, $R^{7c}$, $R^{7d}$, $R^{7e}$, X, Y, and Z are each as defined herein.

Synthesis of compounds of Formula (IXb) is described in U.S. Pat. No. 9,056,852 B2, which is incorporated by reference for such disclosure.

In certain embodiments of compounds of Formulae (IX), (IXa), or (IXb), one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one, two, three, or four substituents $Q^a$; in certain embodiments, one of $R^{7a}$, $R^{7b}$, $R^{7c}$, $R^{7d}$, and $R^{7e}$ is $C_{6-14}$ aryl, e.g., phenyl, optionally substituted with one, two, three, or four substituents $Q^a$; in certain embodiments, one of $R^{7a}$, $R^{7b}$, $R^{7c}$, $R^{7d}$, and $R^{7e}$ is heteroaryl, e.g., 5-membered or 6-membered heteroaryl, optionally substituted with one, two, three, or four substituents $Q^a$; in certain embodiments, one of $R^{7a}$, $R^{7b}$, $R^{7c}$, $R^{7d}$, and $R^{7e}$ is heterocyclyl, e.g., 5-membered or 6-membered heterocyclyl, optionally substituted with one, two, three, or four substituents $Q^a$; in certain embodiments, one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one, two, three, or four substituents $Q^a$; in certain embodiments, one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-fluorophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments of compounds of Formulae (IX), (IXa), or (IXb), $R^{7a}$ is $C_{6-14}$ aryl, heteroaryl, or heterocyclyl, each of which is optionally substituted with one, two, three, or four substituents $Q^a$; in certain embodiments, $R^{7a}$ is $C_{6-14}$ aryl, e.g., phenyl, optionally substituted with one, two, three, or four substituents $Q^a$; in certain embodiments, $R^{7a}$ is heteroaryl, e.g., 5-membered or 6-membered heteroaryl, optionally substituted with one, two, three, or four substituents $Q^a$; in certain embodiments, $R^{7a}$ is heterocyclyl, e.g., 5-membered or 6-membered heterocyclyl, optionally substituted with one, two, three, or four substituents $Q^a$; in certain embodiments, $R^{7a}$ is phenyl, imidazolyl, pyrozolyl, pyridinyl, piperidinyl, or piperazinyl, each optionally substituted with one, two, three, or four substituents $Q^a$; in certain embodiments, $R^{7a}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; in certain embodiments, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-fluorophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments of compounds of Formulae (IX), (IXa), or (IXb), $R^1$ is hydrogen or $-OR^{1a}$, where $R^{1a}$ is $C_{1-6}$ alkyl, optionally substituted with one, two, three, four, or five substituents Q;

$R^2$ is hydrogen;

$R^3$ and $R^4$ are hydrogen;

$R^6$ is $C_{1-6}$ alkyl, optionally substituted with one, two, three, four, or five substituents Q;

$R^{5a}$ and $R^{5b}$ are each independently hydrogen, halo, $C_{1-6}$ alkyl, optionally substituted with one, two, three, four, or five substituents Q;

$R^{5d}$ and $R^{5e}$ are each independently $C_{1-6}$ alkyl, optionally substituted with one, two, three, four, or five substituents Q;

$R^{7a}$ is $C_{6-14}$ aryl, heteroaryl, or heterocyclyl, each of which is optionally substituted with one, two, three, or four substituents $Q^a$;

$R^{7c}$, $R^{7d}$, and $R^{7e}$ are hydrogen; and

X, Y, and Z are each independently N or $CR^x$, with the proviso that at least two of X, Y, and Z are N; where $R^x$ is a hydrogen or $C_{1-6}$ alkyl, optionally substituted with one, two, three, or four substituents $Q^a$.

In certain embodiments of compounds of Formulae (IX), (IXa), or (IXb), $R^1$ is hydrogen or methoxy;
$R^2$ is hydrogen;
$R^3$ and $R^4$ are hydrogen;
$R^6$ is $C_{1-6}$ alkyl, optionally substituted with one or more halo;
$R^{5a}$ and $R^{5b}$ are hydrogen;
$R^{5d}$ and $R^{5e}$ are each independently $C_{1-6}$ alkyl;
$R^{7a}$ is $C_{6-14}$ aryl, heteroaryl, or heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In certain embodiments of compounds of Formulae (IX), (IXa), or (IXb), $R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is $C_{6-14}$ aryl, monocyclic heteroaryl, or monocyclic heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In certain embodiments of compounds of Formulae (IX), (IXa), or (IXb), $R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is phenyl, 5- or 6-membered heteroaryl, or 5- or 6-membered heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In certain embodiments of compounds of Formulae (IX), (IXa), or (IXb), $R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is phenyl, imidazolyl, pyrozolyl, pyridinyl, pyrimidinyl, pyrrolidinyl, piperidinyl, or piperazinyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In certain embodiments of compounds of Formulae (IX), (IXa), or (IXb), $R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is phenyl, imidazolyl, pyrozolyl, pyridinyl, piperidinyl, or piperazinyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

Also provided herein is a compound of Formula (X):

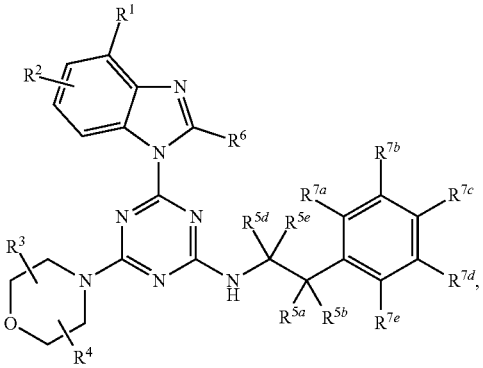

Formula (X)

or an enantiomer, a mixture of enantiomers, a mixture of two or more diastereomers, or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5d}$, $R^{5e}$, $R^{7a}$, $R^{7b}$, $R^{7c}$, $R^{7d}$, and $R^{7e}$ are each as defined herein.

Synthesis of compounds of Formula (X) is described in U.S. Pat. No. 9,056,852 B2, which is incorporated by reference for such disclosure.

In one embodiment, the compound of Formula (X) has the structure of Formula (Xa):

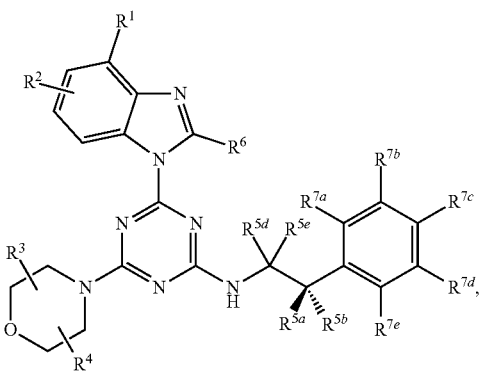

Formula (Xa)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5d}$, $R^{5e}$, $R^{7a}$, $R^{7b}$, $R^{7c}$, $R^{7d}$, and $R^{7e}$ are each as defined herein.

Synthesis of compounds of Formula (Xa) is described in U.S. Pat. No. 9,056,852 B2, which is incorporated by reference for such disclosure.

In another embodiment, the compound of Formula (X) has the structure of Formula (Xb):

Formula (Xb)

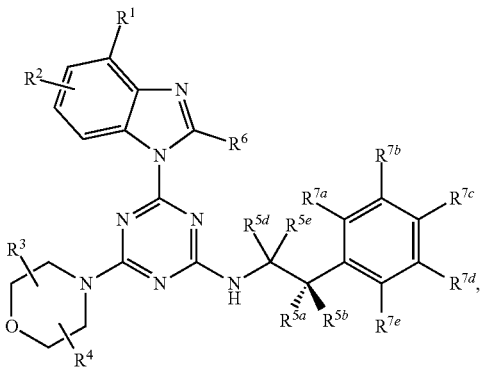

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5d}$, $R^{5e}$, $R^{7a}$, $R^{7b}$, $R^{7c}$, $R^{7d}$, and $R^{7e}$ are each as defined herein.

Synthesis of compounds of Formula (Xb) is described in U.S. Pat. No. 9,056,852 B2, which is incorporated by reference for such disclosure.

In certain embodiments of compounds of Formulae (X), (Xa), or (Xb), one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one, two, three, or four substituents $Q^a$; in certain embodiments, one of $R^{7a}$, $R^{7b}$, $R^{7c}$, $R^{7d}$, and $R^{7e}$ is $C_{6-14}$ aryl, e.g., phenyl, optionally substituted with one, two, three, or four substituents $Q^a$; in certain embodiments, one of $R^{7a}$, $R^{7b}$, $R^{7c}$, $R^{7d}$, and $R^{7e}$ is heteroaryl, e.g., 5-membered or 6-membered heteroaryl, optionally substituted with one, two, three, or four substituents $Q^a$; in certain embodiments, one of $R^{7a}$, $R^{7b}$, $R^{7c}$, $R^{7d}$, and $R^{7e}$ is heterocyclyl, e.g., 5-membered or 6-membered heterocyclyl, optionally substituted with one, two, three, or four substituents $Q^a$; in certain embodiments, one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one, two, three, or four substituents $Q^a$; in certain embodiments, one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-fluorophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments of compounds of Formulae (X), (Xa), or (Xb), $R^{7a}$ is $C_{6-14}$ aryl, heteroaryl, or heterocyclyl, each of which is optionally substituted with one, two, three, or four substituents $Q^a$; in certain embodiments, $R^{7a}$ is $C_{6-14}$ aryl, e.g., phenyl, optionally substituted with one, two, three, or four substituents $Q^a$; in certain embodiments, $R^{7a}$ is heteroaryl, e.g., 5-membered or 6-membered heteroaryl, optionally substituted with one, two, three, or four substituents $Q^a$; in certain embodiments, $R^{7a}$ is heterocyclyl, e.g., 5-membered or 6-membered heterocyclyl, optionally substituted with one, two, three, or four substituents $Q^a$; in certain embodiments, $R^{7a}$ is phenyl, imidazolyl, pyrozolyl, pyridinyl, piperidinyl, or piperazinyl, each optionally substituted with one, two, three, or four substituents $Q^a$; in certain embodiments, $R^{7a}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; in certain embodiments, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-fluorophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments of compounds of Formulae (X), (Xa), or (Xb), $R^1$ is hydrogen or $-OR^{1a}$, where $R^{1a}$ is $C_{1-6}$ alkyl, optionally substituted with one, two, three, four, or five substituents Q;

$R^2$ is hydrogen;

$R^3$ and $R^4$ are hydrogen;

$R^6$ is $C_{1-6}$ alkyl, optionally substituted with one, two, three, four, or five substituents Q;

$R^{5a}$ and $R^{5b}$ are each independently hydrogen, halo, $C_{1-6}$ alkyl, optionally substituted with one, two, three, four, or five substituents Q;

$R^{5d}$ and $R^{5e}$ are each independently $C_{1-6}$ alkyl, optionally substituted with one, two, three, four, or five substituents Q;

$R^{7a}$ is $C_{6-14}$ aryl, heteroaryl, or heterocyclyl, each of which is optionally substituted with one, two, three, or four substituents $Q^a$; and $R^{7b}$, $R^{7c}$, $R^{7d}$, and $R^{7e}$ are hydrogen.

In certain embodiments of compounds of Formulae (X), (Xa), or (Xb), $R^1$ is hydrogen or methoxy;

$R^2$ is hydrogen;

$R^3$ and $R^4$ are hydrogen;

R⁶ is C₁₋₆ alkyl, optionally substituted with one or more halo;

R⁵ᵃ and R⁵ᵇ are hydrogen;

R⁵ᵈ and R⁵ᵉ are each independently C₁₋₆ alkyl;

R⁷ᵃ is C₆₋₁₄ aryl, heteroaryl, or heterocyclyl, each of which is optionally substituted with one, two, three, or four substituents Qᵃ; and R⁷ᵇ, R⁷ᶜ, R⁷ᵈ, and R⁷ᵉ are hydrogen.

In certain embodiments of compounds of Formulae (X), (Xa), or (Xb),

R¹ is hydrogen or methoxy;

R² is hydrogen;

R³ and R⁴ are hydrogen;

R⁶ is difluoromethyl;

R⁵ᵃ and R⁵ᵇ are hydrogen;

R⁵ᵈ and R⁵ᵉ are methyl;

R⁷ᵃ is C₆₋₁₄ aryl, monocyclic heteroaryl, or monocyclic heterocyclyl, each of which is optionally substituted with one, two, three, or four substituents Qᵃ; and R⁷ᵇ, R⁷ᶜ, R⁷ᵈ, and R⁷ᵉ are hydrogen.

In certain embodiments of compounds of Formulae (X), (Xa), or (Xb),

R¹ is hydrogen or methoxy;

R² is hydrogen;

R³ and R⁴ are hydrogen;

R⁶ is difluoromethyl;

R⁵ᵃ and R⁵ᵇ are hydrogen;

R⁵ᵈ and R⁵ᵉ are methyl;

R⁷ᵃ is phenyl, 5- or 6-membered heteroaryl, or 5- or 6-membered heterocyclyl, each of which is optionally substituted with one, two, three, or four substituents Qᵃ; and R⁷ᵇ, R⁷ᶜ, R⁷ᵈ, and R⁷ᵉ are hydrogen.

In certain embodiments of compounds of Formulae (X), (Xa), or (Xb),

R¹ is hydrogen or methoxy;

R² is hydrogen;

R³ and R⁴ are hydrogen;

R⁶ is difluoromethyl;

R⁵ᵃ and R⁵ᵇ are hydrogen;

R⁵ᵈ and R⁵ᵉ are methyl;

R⁷ᵃ is phenyl, imidazolyl, pyrozolyl, pyridinyl, pyrimidinyl, pyrrolidinyl, piperidinyl, or piperazinyl, each of which is optionally substituted with one, two, three, or four substituents Qᵃ; and R⁷ᵇ, R⁷ᶜ, R⁷ᵈ, and R⁷ᵉ are hydrogen.

In certain embodiments of compounds of Formulae (X), (Xa), or (Xb),

R¹ is hydrogen or methoxy;

R² is hydrogen;

R³ and R⁴ are hydrogen;

R⁶ is difluoromethyl;

R⁵ᵃ and R⁵ᵇ are hydrogen;

R⁵ᵈ and R⁵ᵉ are methyl;

R⁷ᵃ is phenyl, imidazolyl, pyrozolyl, pyridinyl, piperidinyl, or piperazinyl, each of which is optionally substituted with one, two, three, or four substituents Qᵃ; and R⁷ᵇ, R⁷ᶜ, R⁷ᵈ, and R⁷ᵉ are hydrogen.

Also provided herein is a compound of Formula (XI):

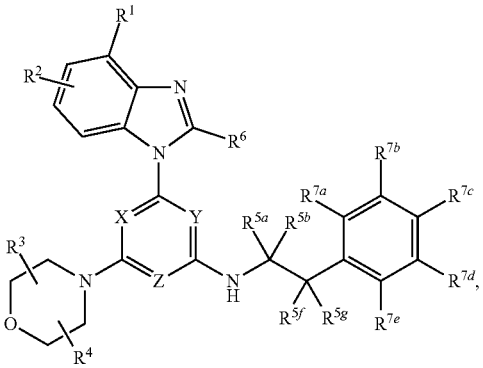

Formula (XI)

or an enantiomer, a mixture of enantiomers, a mixture of two or more diastereomers, or an isotopic variant thereof; or a pharmaceutically acceptable salt, solvate, hydrate, or prodrug thereof; wherein:

R⁷ᵃ, R⁷ᵇ, R⁷ᶜ, R⁷ᵈ, and R⁷ᵉ are each independently (a) hydrogen, cyano, halo, or nitro; (b) C₁₋₆ alkyl, C₂₋₆ alkenyl, C₂₋₆ alkynyl, C₃₋₁₀ cycloalkyl, C₆₋₁₄ aryl, C₇₋₁₅ aralkyl, heteroaryl, or heterocyclyl, each of which is optionally substituted with one, two, three, or four substituents Qᵃ; or (c) —C(O)Rᵃ, —C(O)ORᵃ, —C(O)NRᵇRᶜ, —C(NRᵃ)NRᵇRᶜ, —ORᵃ, —OC(O)Rᵃ, —OC(O)ORᵃ, —OC(O)NRᵇRᶜ, —OC(=NRᵃ)NRᵇRᶜ, —OS(O)Rᵃ, —OS(O)₂Rᵃ, —OS(O)NRᵇRᶜ, —OS(O)₂NRᵇRᶜ, —NRᵇRᶜ, —NRᵃC(O)Rᵈ, —NRᵃC(O)ORᵈ, —NRᵃC(O)NRᵇRᶜ, —NRᵃC(=NRᵈ)NRᵇRᶜ, —NRᵃS(O)Rᵈ, —NRᵃS(O)₂Rᵈ, —NRᵃS(O)NRᵇRᶜ, —NRᵃS(O)₂NRᵇRᶜ, —SRᵃ, —S(O)Rᵃ, —S(O)₂Rᵃ, —S(O)NRᵇRᶜ, or —S(O)₂NRᵇRᶜ; or two of R⁷ᵃ, R⁷ᵇ, R⁷ᶜ, R⁷ᵈ, and R⁷ᵉ that are adjacent to each other form C₃₋₁₀ cycloalkenyl, C₆₋₁₄ aryl, heteroaryl, or heterocyclyl, each optionally substituted with one, two, three, or four substituents Qᵃ; and R¹, R², R³, R⁴, R⁶, R¹ᵃ, R¹ᵇ, R¹ᶜ, R¹ᵈ, R⁵ᵃ, R⁵ᵇ, R⁵ᶠ, R⁵ᵍ, X, Y, and Z are each as defined herein.

Synthesis of compounds of Formula (XI) is described in U.S. Pat. No. 9,056,852 B2, which is incorporated by reference for such disclosure.

In one embodiment, the compound of Formula (XI) has the structure of Formula (XIa):

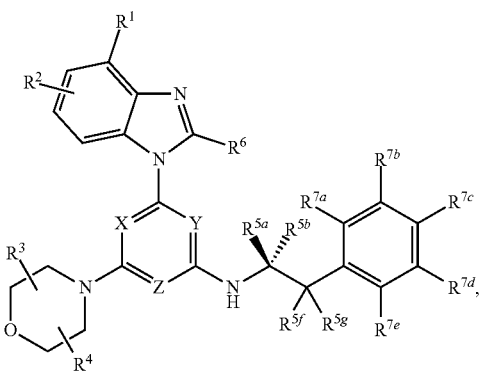

Formula (XIa)

or an isotopic variant thereof; or a pharmaceutically acceptable salt, solvate, hydrate, or prodrug thereof; wherein R¹, $R^2$, $R^3$, $R^4$, $R^6$, $R^{5a}$, $R^{5b}$, $R^{5f}$, $R^{5g}$, $R^{7a}$, $R^{7b}$, $R^{7c}$, $R^{7d}$, $R^{7e}$, X, Y, and Z are each as defined herein.

Synthesis of compounds of Formula (XIa) is described in U.S. Pat. No. 9,056,852 B2, which is incorporated by reference for such disclosure.

In another embodiment, the compound of Formula (XI) has the structure of Formula (XIb):

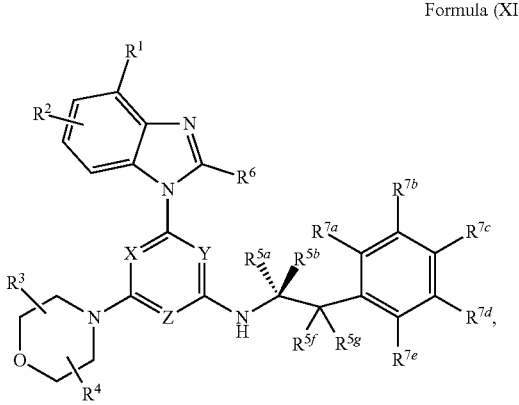

Formula (XIb)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5f}$, $R^{5g}$, $R^{7a}$, $R^{7b}$, $R^{7c}$, $R^{7d}$, $R^{7e}$, X, Y, and Z are each as defined herein.

Synthesis of compounds of Formula (XIb) is described in U.S. Pat. No. 9,056,852 B2, which is incorporated by reference for such disclosure.

In certain embodiments of compounds of Formulae (XI), (XIa), or (XIb), $R^{5a}$ and $R^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; and $R^1$, $R^2$, $R^3$, $R^4$, $R^{5f}$, $R^{5g}$, $R^6$, $R^{7a}$, $R^{7b}$, $R^{7c}$, $R^{7d}$, $R^{7e}$, X, Y, Z, $R^{1a}$, $R^{1b}$, $R^{1c}$, and $R^{1d}$ are defined herein elsewhere.

In certain embodiments of compounds of Formulae (XI), (XIa), or (XIb), one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one, two, three, or four substituents $Q^a$; in certain embodiments, one of $R^{7a}$, $R^{7b}$, $R^{7c}$, $R^{7d}$, and $R^{7e}$ is $C_{6-14}$ aryl, e.g., phenyl, optionally substituted with one, two, three, or four substituents $Q^a$; in certain embodiments, one of $R^{7a}$, $R^{7b}$, $R^{7c}$, $R^{7d}$, and $R^{7e}$ is heteroaryl, e.g., 5-membered or 6-membered heteroaryl, optionally substituted with one, two, three, or four substituents $Q^a$; in certain embodiments, one of $R^{7a}$, $R^{7b}$, $R^{7c}$, $R^{7d}$, and $R^{7e}$ is heterocyclyl, e.g., 5-membered or 6-membered heterocyclyl, optionally substituted with one, two, three, or four substituents $Q^a$; in certain embodiments, one of lea, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; in certain embodiments, one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one, two, three, or four substituents $Q^a$; in certain embodiments, one of lea, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-fluorophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments of compounds of Formulae (XI), (XIa), or (XIb), $R^{7a}$ is $C_{6-14}$ aryl, heteroaryl, or heterocyclyl, each of which is optionally substituted with one, two, three, or four substituents $Q^a$; in certain embodiments, $R^{7a}$ is $C_{6-14}$ aryl, e.g., phenyl, optionally substituted with one, two, three, or four substituents $Q^a$; in certain embodiments, $R^{7a}$ is heteroaryl, e.g., 5-membered or 6-membered heteroaryl, optionally substituted with one, two, three, or four substituents $Q^a$; in certain embodiments, $R^{7a}$ is heterocyclyl, e.g., 5-membered or 6-membered heterocyclyl, optionally substituted with one, two, three, or four substituents $Q^a$; in certain embodiments, $R^{7a}$ is phenyl, imidazolyl, pyrozolyl, pyridinyl, piperidinyl, or piperazinyl, each optionally substituted with one, two, three, or four substituents $Q^a$; in certain embodiments, $R^{7a}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; in certain embodiments, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-fluorophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments of compounds of Formulae (XI), (XIa), or (XIb), $R^1$ is hydrogen or $-OR^{1a}$, where $R^{1a}$ is $C_{1-6}$ alkyl, optionally substituted with one, two, three, four, or five substituents Q;

$R^2$ is hydrogen;

$R^3$ and $R^4$ are hydrogen;

$R^6$ is $C_{1-6}$ alkyl, optionally substituted with one, two, three, four, or five substituents Q;

$R^{5a}$ and $R^{5b}$ are each independently $C_{1-6}$ alkyl, optionally substituted with one, two, three, four, or five substituents Q;

$R^{5f}$ and $R^{5g}$ are each independently hydrogen, halo, $C_{1-6}$ alkyl, optionally substituted with one, two, three, four, or five substituents Q; or $R^{5f}$ and $R^{5g}$ together with the carbon atom to which they are attached form $C_{1-10}$ cycloalkyl or heterocyclyl, each of which is optionally substituted with one, two, three, four, or five substituents Q;

$R^{7a}$ is $C_{6-14}$ aryl, heteroaryl, or heterocyclyl, each of which is optionally substituted with one, two, three, or four substituents $Q^a$;

$R^{7b}$, $R^{7c}$, $R^{7d}$, and $R^{7e}$ are hydrogen; and

X, Y, and Z are each independently N or $CR^x$, with the proviso that at least two of X, Y, and Z are N; where $R^x$ is a hydrogen or $C_{1-6}$ alkyl, optionally substituted with one, two, three, or four substituents $Q^a$.

In certain embodiments of compounds of Formulae (XI), (XIa), or (XIb), $R^1$ is hydrogen or methoxy;

$R^2$ is hydrogen;

$R^3$ and $R^4$ are hydrogen;

$R^6$ is $C_{1-6}$ alkyl, optionally substituted with one or more halo;

$R^{5a}$ and $R^{5b}$ are each independently $C_{1-6}$ alkyl;

$R^{5f}$ and $R^{5g}$ are each independently hydrogen or $C_{1-6}$ alkyl; or $R^{5f}$ and $R^{5g}$ together with the carbon atom to which they are attached form $C_{1-10}$ cycloalkyl;

$R^{7a}$ is $C_{6-14}$ aryl, heteroaryl, or heterocyclyl, each of which is optionally substituted with one, two, three, or four substituents $Q^a$;

$R^{7b}$, $R^{7c}$, $R^{7d}$, and $R^{7e}$ are hydrogen; and

X, Y, and Z are each independently N or CH.

In certain embodiments of compounds of Formulae (XI), (XIa), or (XIb), $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are methyl;

$R^{5f}$ and $R^{5g}$ are hydrogen; or $R^{5f}$ and $R^{5g}$ together with the carbon atom to which they are attached form cyclopropyl, cyclobutyl, cyclopentyl, or cyclohexyl;

$R^{7a}$ is $C_{6-14}$ aryl, monocyclic heteroaryl, or monocyclic heterocyclyl, each of which is optionally substituted with one, two, three, or four substituents $Q^a$;

$R^{7b}$, $R^{7c}$, $R^{7d}$, and $R^{7e}$ are hydrogen; and

X, Y, and Z are each independently N or CH.

In certain embodiments of compounds of Formulae (XI), (XIa), or (XIb), $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are methyl;

$R^{5f}$ and $R^{5g}$ are hydrogen; or $R^{5f}$ and $R^{5g}$ together with the carbon atom to which they are attached form cyclopropyl, cyclobutyl, cyclopentyl, or cyclohexyl;

$R^{7a}$ is phenyl, 5- or 6-membered heteroaryl, or 5- or 6-membered heterocyclyl, each of which is optionally substituted with one, two, three, or four substituents $Q^a$;

$R^{7b}$, $R^{7c}$, $R^{7d}$, and $R^{7e}$ are hydrogen; and

X, Y, and Z are each independently N or CH.

In certain embodiments of compounds of Formulae (XI), (XIa), or (XIb), $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are methyl;

$R^{5f}$ and $R^{5g}$ are hydrogen; or $R^{5f}$ and $R^{5g}$ together with the carbon atom to which they are attached form cyclopropyl, cyclobutyl, cyclopentyl, or cyclohexyl;

$R^{7a}$ is phenyl, imidazolyl, pyrozolyl, pyridinyl, pyrimidinyl, pyrrolidinyl, piperidinyl, or piperazinyl, each of which is optionally substituted with one, two, three, or four substituents $Q^a$;

$R^{7b}$, $R^{7c}$, $R^{7d}$, and $R^{7e}$ are hydrogen; and

X, Y, and Z are each independently N or CH.

In certain embodiments of compounds of Formulae (XI), (XIa), or (XIb), $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are methyl;

$R^{5f}$ and $R^{5g}$ are hydrogen; or $R^{5f}$ and $R^{5g}$ together with the carbon atom to which they are attached form cyclopropyl, cyclobutyl, cyclopentyl, or cyclohexyl;

$R^{7a}$ is phenyl, imidazolyl, pyrozolyl, pyridinyl, piperidinyl, or piperazinyl, each of which is optionally substituted with one, two, three, or four substituents $Q^a$;

$R^{7b}$, $R^{7c}$, $R^{7d}$, and $R^{7e}$ are hydrogen; and

X, Y, and Z are each independently N or CH.

Also provided herein is a compound of Formula (XVI):

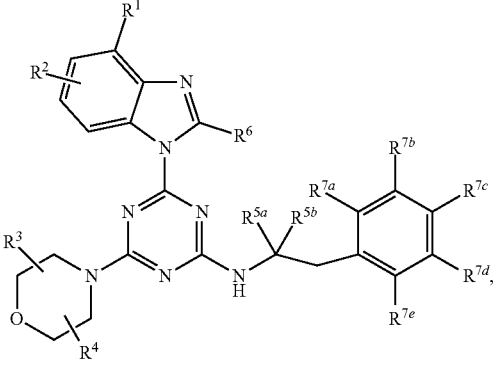

Formula (XVI)

or an enantiomer, a mixture of enantiomers, a mixture of two or more diastereomers, or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{7a}$, $R^{7b}$, $R^{7c}$, and $R^{7e}$ are each as defined herein.

Synthesis of compounds of Formula (XVI) is described in U.S. Pat. No. 9,056,852 B2, which is incorporated by reference for such disclosure.

In one embodiment of a compound of Formula (XVI), one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In another embodiment of a compound of Formula (XVI), one of $R^{7a}$, $R^{7b}$, $R^{7c}$, $R^{7d}$, and $R^{7e}$ is $C_{6-14}$ aryl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is heteroaryl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is 5-membered or 6-membered heteroaryl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is heterocyclyl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is 5-membered or 6-membered heterocyclyl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment of a compound of Formula (XVI), one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-fluorophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment of a compound of Formula (XVI), $R^{7a}$ is $C_{6-14}$ aryl, heteroaryl, or heterocyclyl, each of which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In another embodiment of a compound of Formula (XVI), $R^{7a}$ is $C_{6-14}$ aryl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment of a compound of Formula (XVI), $R^{7a}$ is heteroaryl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment of a compound of Formula (XVI), $R^{7a}$ is 5-membered or 6-membered heteroaryl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment of a compound of Formula (XVI), $R^{7a}$ is heterocyclyl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment of a compound of Formula (XVI), $R^{7a}$ is 5-membered or 6-membered heterocyclyl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7e}$, X, Y, and Z are each as defined herein.

In yet another embodiment of a compound of Formula (XVI), $R^{7a}$ is phenyl, imidazolyl, pyrozolyl, pyridinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment of a compound of Formula (XVI), $R^{7a}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; and $R^1$, $R^2$, $R^3$, $R^4$, $R^5$, $R^6$, $R^{5a}$, $R^{5b}$, $R^{7b}$, $R^{7c}$, $R^{7d}$, $R^{7e}$, X, Y, and Z are each as defined herein.

In yet another embodiment of a compound of Formula (XVI), $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In yet another embodiment of a compound of Formula (XVI), $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-fluorophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, $R^{7b}$, $R^{7c}$, $R^{7e}$, X, Y, and Z are each as defined herein.

In one embodiment of a compound of Formula (XVI),
$R^1$ is hydrogen or —$OR^{1a}$, where $R^{1a}$ is $C_{1-6}$ alkyl, optionally substituted with one, two, three, four, or five substituents Q;
$R^2$ is hydrogen;
$R^3$ and $R^4$ are hydrogen;
$R^6$ is $C_{1-6}$ alkyl, optionally substituted with one, two, three, four, or five substituents Q;
$R^{5a}$ and $R^{5b}$ are each independently $C_{1-6}$ alkyl, optionally substituted with one, two, three, four, or five substituents Q;
$R^{7a}$ is $C_{6-14}$ aryl, heteroaryl, or heterocyclyl, each of which is optionally substituted with one, two, three, or four substituents $Q^a$; and
$R^{7b}$, $R^{7c}$, $R^{7d}$, and $R^{7e}$ are hydrogen.

In one embodiment of a compound of Formula (XVI),
$R^1$ is hydrogen or methoxy;
$R^2$ is hydrogen;
$R^3$ and $R^4$ are hydrogen;
$R^6$ is $C_{1-6}$ alkyl, optionally substituted with one or more halo;
$R^{5a}$ and $R^{5b}$ are each independently $C_{1-6}$ alkyl;
$R^{7a}$ is $C_{6-14}$ aryl, heteroaryl, or heterocyclyl, each of which is optionally substituted with one, two, three, or four substituents $Q^a$; and
$R^{7b}$, $R^{7c}$, $R^{7d}$, and $R^{7e}$ are hydrogen.

In one embodiment of a compound of Formula (XVI),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{7a}$ is $C_{6-14}$ aryl, monocyclic heteroaryl, or monocyclic heterocyclyl, each of which is optionally substituted with one, two, three, or four substituents $Q^a$; and
$R^{7b}$, $R^{7c}$, $R^{7d}$, and $R^{7e}$ are hydrogen.

In one embodiment of a compound of Formula (XVI),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{7a}$ is phenyl, 5- or 6-membered heteroaryl, or 5- or 6-membered heterocyclyl, each of which is optionally substituted with one, two, three, or four substituents $Q^a$; and
$R^{7b}$, $R^{7c}$, $R^{7d}$, and $R^{7e}$ are hydrogen.

In one embodiment of a compound of Formula (XVI),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{7a}$ is phenyl, imidazolyl, pyrozolyl, pyridinyl, pyrimidinyl, pyrrolidinyl, piperidinyl, or piperazinyl, each of which is optionally substituted with one, two, three, four, or five substituents Q; and
$R^{7b}$, $R^{7c}$, $R^{7d}$, and $R^{7e}$ are hydrogen.

In one embodiment of a compound of Formula (XVI),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{7a}$ is phenyl, imidazolyl, pyrozolyl, pyridinyl, piperidinyl, or piperazinyl, each of which is optionally substituted with one, two, three, or four substituents $Q^a$; and
$R^{7b}$, $R^{7c}$, $R^{7d}$, and $R^{7e}$ are hydrogen.

In one embodiment, the compound of Formula (XVI) has the structure of Formula (XVIa):

Formula (XVIa)

or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{7a}$, $R^{7b}$, $R^{7c}$, and $R^{7e}$ are each as defined herein.

Synthesis of compounds of Formula (XVIa) is described in U.S. Pat. No. 9,056,852 B2, which is incorporated by reference for such disclosure.

In one embodiment of a compound of Formula (XVIa), one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment of a compound of Formula (XVIa), one of $R^{7a}$, $R^{7b}$, $R^{7c}$, $R^{7d}$, and $R^{7e}$ is $C_{6-14}$ aryl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment of a compound of Formula (XVIa), one of $R^{7a}$, $R^{7b}$, $R^{7c}$, $R^{7d}$, and $R^{7e}$ is heteroaryl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment of a compound of Formula (XVIa), one of $R^{7a}$, $R^{7b}$, $R^{7c}$, $R^{7d}$, and $R^{7e}$ is 5-membered or 6-membered heteroaryl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment of a compound of Formula (XVIa), one of $R^{7a}$, $R^{7b}$, $R^{7c}$, $R^{7d}$, and $R^{7e}$ is heterocyclyl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment of a compound of Formula (XVIa), one of $R^{7a}$, $R^{7b}$, $R^{7c}$, $R^{7d}$, and $R^{7e}$ is 5-membered or 6-membered heterocyclyl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment of a compound of Formula (XVIa), one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment of a compound of Formula (XVIa), one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment of a compound of Formula (XVIa), one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In one embodiment of a compound of Formula (XVIa), one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-fluorophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment of a compound of Formula (XVIa), $R^{7a}$ is $C_{6-14}$ aryl, heteroaryl, or heterocyclyl, each of which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIa), $R^{7a}$ is $C_{6-14}$ aryl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIa), $R^{7a}$ is heteroaryl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIa), $R^{7a}$ is 5-membered or 6-membered heteroaryl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIa), $R^{7a}$ is heterocyclyl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIa), $R^{7a}$ is 5-membered or 6-membered heterocyclyl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIa), $R^{7a}$ is phenyl, imidazolyl, pyrozolyl, pyridinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIa), $R^{7a}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIa), $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In one embodiment of a compound of Formula (XVIa), $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-fluorophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIa), $R^1$ is hydrogen or $-OR^{1a}$, where $R^{1a}$ is $C_{1-6}$ alkyl, optionally substituted with one, two, three, four, or five substituents Q;

$R^2$ is hydrogen;

$R^3$ and $R^4$ are hydrogen;

$R^6$ is $C_{1-6}$ alkyl, optionally substituted with one, two, three, four, or five substituents Q;

$R^{5a}$ and $R^{5b}$ are each independently hydrogen or $C_{1-6}$ alkyl, optionally substituted with one, two, three, four, or five substituents Q;

$R^{7a}$ is $C_{6-14}$ aryl, heteroaryl, or heterocyclyl, each of which is optionally substituted with one, two, three, or four substituents $Q^a$; and $R^{7b}$, $R^{7c}$, $R^{7d}$, and $R^{7e}$ are hydrogen.

In one embodiment of a compound of Formula (XVIa),
R$^1$ is hydrogen or methoxy;
R$^2$ is hydrogen;
R$^3$ and R$^4$ are hydrogen;
R$^6$ is C$_{1-6}$ alkyl, optionally substituted with one or more halo;
R$^{5a}$ and R$^{5b}$ are each independently hydrogen or C$_{1-6}$ alkyl;
R$^{7a}$ is C$_{6-14}$ aryl, heteroaryl, or heterocyclyl, each of which is optionally substituted with one, two, three, or four substituents Q$^a$; and
R$^{7b}$, R$^{7c}$, R$^{7d}$, and R$^{7e}$ are hydrogen.

In one embodiment of a compound of Formula (XVIa),
R$^1$ is hydrogen or methoxy;
R$^2$ is hydrogen;
R$^3$ and R$^4$ are hydrogen;
R$^6$ is difluoromethyl;
R$^{5a}$ and R$^{5b}$ are each independently hydrogen or C$_{1-6}$ alkyl;
R$^{7a}$ is C$_{6-14}$ aryl, monocyclic heteroaryl, or monocyclic heterocyclyl, each of which is optionally substituted with one, two, three, or four substituents Q$^a$; and
R$^{7b}$, R$^{7c}$, R$^{7d}$, and R$^{7e}$ are hydrogen.

In one embodiment of a compound of Formula (XVIa),
R$^1$ is hydrogen or methoxy;
R$^2$ is hydrogen;
R$^3$ and R$^4$ are hydrogen;
R$^6$ is difluoromethyl;
R$^{5a}$ and R$^{5b}$ are each independently hydrogen or C$_{1-6}$ alkyl;
R$^{7a}$ is phenyl, 5- or 6-membered heteroaryl, or 5- or 6-membered heterocyclyl, each of which is optionally substituted with one, two, three, or four substituents Q$^a$; and
R$^{7b}$, R$^{7c}$, R$^{7d}$, and R$^{7e}$ are hydrogen.

In one embodiment of a compound of Formula (XVIa),
R$^1$ is hydrogen or methoxy;
R$^2$ is hydrogen;
R$^3$ and R$^4$ are hydrogen;
R$^6$ is difluoromethyl;
R$^{5a}$ and R$^{5b}$ are each independently hydrogen or C$_{1-6}$ alkyl;
R$^{7a}$ is phenyl, imidazolyl, pyrozolyl, pyridinyl, pyrrolidinyl, piperidinyl, piperidinyl, or piperazinyl, each of which is optionally substituted with one, two, three, or four substituents Q$^a$; and
R$^{7b}$, R$^{7c}$, R$^{7d}$, and R$^{7e}$ are hydrogen.

In one embodiment of a compound of Formula (XVIa),
R$^1$ is hydrogen or methoxy;
R$^2$ is hydrogen;
R$^3$ and R$^4$ are hydrogen;
R$^6$ is difluoromethyl;
R$^{5a}$ and R$^{5b}$ are each independently hydrogen or C$_{1-6}$ alkyl;
R$^{7a}$ is phenyl, imidazolyl, pyrozolyl, pyridinyl, piperidinyl, or piperazinyl, each of which is optionally substituted with one, two, three, or four substituents Q$^a$; and
R$^{7b}$, R$^{7c}$, R$^{7d}$, and R$^{7e}$ are hydrogen.

In another embodiment, the compound of Formula (XVI) has the structure of Formula (XVIb):

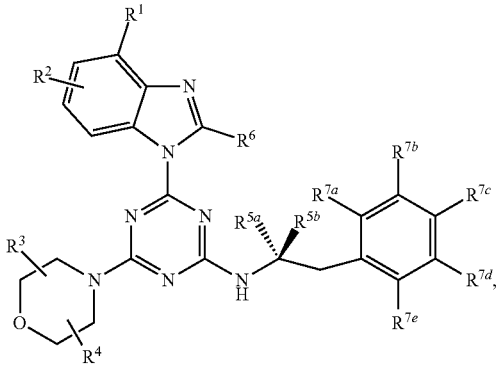

Formula (XVIb)

or an isotopic variant thereof; or a pharmaceutically acceptable salt, solvate, hydrate, or prodrug thereof; wherein R$^1$, R$^2$, R$^3$, R$^4$, R$^6$, R$^{5a}$, R$^{5b}$, R$^{7a}$, R$^{7b}$, R$^{7c}$, R$^{7d}$ and R$^{7e}$ are each as defined herein.

In one embodiment of a compound of Formula (XVIb), one of R$^{7a}$, R$^{7b}$, R$^{7c}$, R$^{7d}$, and R$^{7e}$ is C$_{6-14}$ aryl, heteroaryl, or heterocyclyl, each of which is optionally substituted with one, two, three, or four substituents Q$^a$; and R$^1$, R$^2$, R$^3$, R$^4$, R$^6$, R$^{5a}$, R$^{5b}$, the remaining of R$^{7a}$, R$^{7b}$, R$^{7c}$, R$^{7d}$, and R$^{7e}$, X, Y, and Z are each as defined herein.

In one embodiment of a compound of Formula (XVIb), one of R$^{7a}$, R$^{7b}$, R$^{7c}$, R$^{7d}$, and R$^{7e}$ is C$_{6-14}$ aryl, which is optionally substituted with one, two, three, or four substituents Q$^a$; and R$^1$, R$^2$, R$^3$, R$^4$, R$^6$, R$^{5a}$, R$^{5b}$, the remaining of R$^{7a}$, R$^{7b}$, R$^{7c}$, R$^{7d}$, and R$^{7e}$, X, Y, and Z are each as defined herein.

In one embodiment of a compound of Formula (XVIb), one of R$^{7a}$, R$^{7b}$, R$^{7c}$, R$^{7d}$, and R$^{7e}$ is heteroaryl, which is optionally substituted with one, two, three, or four substituents Q$^a$; and R$^1$, R$^2$, R$^3$, R$^4$, R$^6$, R$^{5a}$, R$^{5b}$, the remaining of R$^{7a}$, R$^{7b}$, R$^{7c}$, R$^{7d}$, and R$^{7e}$, X, Y, and Z are each as defined herein.

In one embodiment of a compound of Formula (XVIb), one of R$^{7a}$, R$^{7b}$, R$^{7c}$, R$^{7d}$, and R$^{7e}$ is 5-membered or 6-membered heteroaryl, which is optionally substituted with one, two, three, or four substituents Q$^a$; and R$^1$, R$^2$, R$^3$, R$^4$, R$^6$, R$^{5a}$, R$^{5b}$, the remaining of R$^{7a}$, R$^{7b}$, R$^{7c}$, R$^{7d}$, and R$^{7e}$, X, Y, and Z are each as defined herein.

In one embodiment of a compound of Formula (XVIb), one of R$^{7a}$, R$^{7b}$, R$^{7c}$, R$^{7d}$, and R$^{7e}$ is heterocyclyl, which is optionally substituted with one, two, three, or four substituents Q$^a$; and R$^1$, R$^2$, R$^3$, R$^4$, R$^6$, R$^{5a}$, R$^{5b}$, the remaining of R$^{7a}$, R$^{7b}$, R$^{7c}$, R$^{7d}$, and R$^{7e}$, X, Y, and Z are each as defined herein.

In one embodiment of a compound of Formula (XVIb), one of R$^{7a}$, R$^{7b}$, R$^{7c}$, R$^{7d}$, and R$^{7e}$ is 5-membered or 6-membered heterocyclyl, which is optionally substituted with one, two, three, or four substituents Q$^a$; and R$^1$, R$^2$, R$^3$, R$^4$, R$^6$, R$^{5a}$, R$^{5b}$, the remaining of R$^{7a}$, R$^{7b}$, R$^{7c}$, R$^{7d}$, and R$^{7e}$, X, Y, and Z are each as defined herein.

In one embodiment of a compound of Formula (XVIb), one of R$^{7a}$, R$^{7b}$, R$^{7c}$, R$^{7d}$, and R$^{7e}$ is phenyl, imidazolyl, pyrozolyl, pyridinyl, piperidinyl, or piperazinyl, each optionally substituted with one, two, three, or four substituents Q$^a$; and R$^1$, R$^2$, R$^3$, R$^4$, R$^6$, R$^{5a}$, R$^{5b}$, the remaining of R$^{7a}$, R$^{7b}$, R$^{7c}$, R$^{7d}$, and R$^{7e}$, X, Y, and Z are each as defined herein.

In one embodiment of a compound of Formula (XVIb), one of R$^{7a}$, R$^{7b}$, R$^{7c}$, R$^{7d}$, and R$^{7e}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment of a compound of Formula (XVIb), one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In one embodiment of a compound of Formula (XVIb), one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-fluorophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment of a compound of Formula (XVIb), $R^{7a}$ is $C_{6-14}$ aryl, heteroaryl, or heterocyclyl, each of which is optionally substituted with one, two, three, four, or five substituents Q; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIb), $R^{7a}$ is $C_{6-14}$ aryl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIb), $R^{7a}$ is heteroaryl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIb), $R^{7a}$ is 5-membered or 6-membered heteroaryl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7e}$, X, Y, and Z are each as defined herein.

In one embodiment of a compound of Formula (XVIb), $R^{7a}$ is heterocyclyl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIb), $R^{7a}$ is 5-membered or 6-membered heterocyclyl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIb), $R^{7a}$ is phenyl, imidazolyl, pyrozolyl, pyridinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIb), $R^{7a}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIb), $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In one embodiment of a compound of Formula (XVIb), $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-fluorophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVIb),
$R^1$ is hydrogen or $-OR^{1a}$, where $R^{1a}$ is $C_{1-6}$ alkyl, optionally substituted with one, two, three, four, or five substituents Q;
$R^2$ is hydrogen;
$R^3$ and $R^4$ are hydrogen;
$R^6$ is $C_{1-6}$ alkyl, optionally substituted with one, two, three, four, or five substituents Q;
$R^{5a}$ and $R^{5b}$ are each independently hydrogen or $C_{1-6}$ alkyl, optionally substituted with one, two, three, four, or five substituents Q;
$R^{7a}$ is $C_{6-14}$ aryl, heteroaryl, or heterocyclyl, each of which is optionally substituted with one, two, three, or four substituents $Q^a$; and
$R^{7b}$, $R^{7c}$, $R^{7d}$, and $R^{7e}$ are hydrogen.

In one embodiment of a compound of Formula (XVIb),
$R^1$ is hydrogen or methoxy;
$R^2$ is hydrogen;
$R^3$ and $R^4$ are hydrogen;
$R^6$ is $C_{1-6}$ alkyl, optionally substituted with one or more halo;
$R^{5a}$ and $R^{5b}$ are each independently hydrogen or $C_{1-6}$ alkyl;
$R^{7a}$ is $C_{6-14}$ aryl, heteroaryl, or heterocyclyl, each of which is optionally substituted with one, two, three, or four substituents $Q^a$; and
$R^{7b}$, $R^{7c}$, $R^{7d}$, and $R^{7e}$ are hydrogen.

In one embodiment of a compound of Formula (XVIb),
$R^1$ is hydrogen or methoxy;
$R^2$ is hydrogen;
$R^3$ and $R^4$ are hydrogen;
$R^6$ is difluoromethyl;

$R^{5a}$ and $R^{5b}$ are each independently hydrogen or $C_{1-6}$ alkyl;

$R^{7a}$ is $C_{6-14}$ aryl, monocyclic heteroaryl, or monocyclic heterocyclyl, each of which is optionally substituted with one, two, three, or four substituents $Q^a$; and $R^{7b}$, $R^{7c}$, $R^{7d}$, and $R^{7e}$ are hydrogen.

In one embodiment of a compound of Formula (XVIb),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{1-6}$ alkyl;
$R^{7a}$ is phenyl, 5- or 6-membered heteroaryl, or 5- or 6-membered heterocyclyl, each of which is optionally substituted with one, two, three, or four substituents $Q^a$; and
$R^{7b}$, $R^{7c}$, $R^{7d}$, and $R^{7e}$ are hydrogen.

In one embodiment of a compound of Formula (XVIb),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{1-6}$ alkyl;
$R^{7a}$ is phenyl, imidazolyl, pyrozolyl, pyridinyl, pyrimidinyl, pyrrolidinyl, piperidinyl, or piperazinyl, each of which is optionally substituted with one, two, three, or four substituents $Q^a$; and
$R^{7b}$, $R^{7c}$, $R^{7d}$, and $R^{7e}$ are hydrogen.

In one embodiment of a compound of Formula (XVIb),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{1-6}$ alkyl;
$R^{7a}$ is phenyl, imidazolyl, pyrozolyl, pyridinyl, piperidinyl, or piperazinyl, each of which is optionally substituted with one, two, three, or four substituents $Q^a$; and
$R^{7b}$, $R^{7c}$, $R^{7d}$, and $R^{7e}$ are hydrogen.

In one embodiment of compounds of Formulae (XVI), (XVIa), or (XVIb), $R^{5a}$ and $R^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2$$R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^1$)N$R^{1b}R^{1c}$, —N$R^{1a}$S(O)$R^{1d}$, —N$R^{1a}$S(O)$_2$$R^{1d}$, —N$R^{1a}$S(C)N$R^{1b}R^{1c}$, —N$R^{1a}$S(O)$_2$N$R^{1b}R^{1c}$, —S$R^{1a}$, —S(O)$R^{1a}$, —S(O)$_2$$R^{1a}$, —S(C)N$R^{1b}R^{1c}$, or —S(O)$_2$N$R^{1b}R^{1c}$; and $R^1$, $R^2$, $R^3$, $R^4$, $R^6$, $R^{7a}$, $R^{7b}$, $R^{7c}$, $R^{7d}$, $R^{7e}$, $R^{1a}$, $R^{1b}$, $R^{1c}$, and $R^{1d}$ are defined herein elsewhere.

In one embodiment of a compound of any of the formulae provided herein,
$R^1$ is hydrogen or —O$R^{1a}$, where $R^{1a}$ is $C_{1-6}$ alkyl, optionally substituted with one, two, three, four, or five substituents Q;
$R^2$ is hydrogen;
$R^3$ and $R^4$ are hydrogen;
$R^6$ is $C_{1-6}$ alkyl, optionally substituted with one, two, three, four, or five substituents Q;
$R^{5a}$ and $R^{5b}$ are each independently hydrogen or $C_{1-6}$ alkyl optionally substituted with one, two, three, four, or five substituents Q;

$R^{7a}$ is $C_{6-14}$ aryl, heteroaryl, or heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or C$R^x$, with the proviso that at least two of X, Y, and Z are N; where $R^x$ is a hydrogen or $C_{1-6}$ alkyl, optionally substituted with one, two, three, or four substituents $Q^a$;

In one embodiment of a compound of any of the formulae provided herein,
$R^1$ is hydrogen or methoxy;
$R^2$ is hydrogen;
$R^3$ and $R^4$ are hydrogen;
$R^6$ is $C_{1-6}$ alkyl, optionally substituted with one or more halo;
$R^{5a}$ and $R^{5b}$ are each independently hydrogen or $C_{1-6}$ alkyl;
$R^{7a}$ is $C_{6-14}$ aryl, heteroaryl, or heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In one embodiment of a compound of any of the formulae provided herein,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{1-6}$ alkyl;
$R^{7a}$ is $C_{6-14}$ aryl, monocyclic heteroaryl, or monocyclic heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In one embodiment of a compound of any of the formulae provided herein,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{1-6}$ alkyl;
$R^{7a}$ is phenyl, 5- or 6-membered heteroaryl, or 5- or 6-membered heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In one embodiment of a compound of any of the formulae provided herein,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{1-6}$ alkyl;
$R^{7a}$ is phenyl, imidazolyl, pyrozolyl, pyridinyl, pyrimidinyl, pyrrolidinyl, piperidinyl, or piperazinyl, each of which is optionally substituted with one, two, three, or four substituents $Q^a$;
$R^{7b}$, $R^{7c}$, $R^{7d}$, and $R^7$ are hydrogen; and
X, Y, and Z are each independently N or CH.

In one embodiment of a compound of any of the formulae provided herein,
$R^1$ is hydrogen or methoxy;
$R^2$ is hydrogen;
$R^3$ and $R^4$ are hydrogen;
$R^6$ is difluoromethyl;

$R^{5a}$ and $R^{5b}$ are each independently hydrogen or $C_{1-6}$ alkyl;

$R^{7a}$ is phenyl, imidazolyl, pyrozolyl, pyridinyl, piperidinyl, or piperazinyl, each of which is optionally substituted with one, two, three, or four substituents $Q^a$;

$R^{7b}$, $R^{7c}$, $R^{7d}$, and $R^{7e}$ are hydrogen; and

X, Y, and Z are each independently N or CH.

The groups or variables, $R^1$, $R^2$, $R^3$, $R^4$, $R^6$, $R^{5a}$, $R^{5b}$, $R^{5c}$, $R^{5d}$, $R^{5e}$, $R^{5f}$, $R^{5g}$, $R^{7a}$, $R^{7b}$, $R^{7c}$, $R^{7d}$, $R^{7e}$, m, n, X, Y, and Z in any of the Formulae provided herein, e.g., Formulae (I), (IX), (X), (XI), (XVI), (IXa), (Xa), (XIa), (XVIa), (IXb), (Xb), (XIb), (XVIb), are further defined in the embodiments described herein. All combinations of the embodiments provided herein for such groups and/or variables are within the scope of this disclosure.

In certain embodiments, $R^1$ is hydrogen. In certain embodiments, $R^1$ is cyano. In certain embodiments, $R^1$ is halo. In certain embodiments, $R^1$ is fluoro, chloro, bromo, or iodo. In certain embodiments, $R^1$ is nitro. In certain embodiments, $R^1$ is $C_{1-6}$ alkyl, optionally substituted with one, two, three, four, or five substituents Q as described herein. In certain embodiments, $R^1$ is $C_{2-6}$ alkenyl, optionally substituted with one, two, three, four, or five substituents Q as described herein. In certain embodiments, $R^1$ is $C_{2-6}$ alkynyl, optionally substituted with one, two, three, four, or five substituents Q as described herein. In certain embodiments, $R^1$ is $C_{3-10}$ cycloalkyl, optionally substituted with one, two, three, four, or five substituents Q as described herein. In certain embodiments, $R^1$ is $C_{6-14}$ aryl, optionally substituted with one, two, three, four, or five substituents Q as described herein. In certain embodiments, $R^1$ is $C_{7-15}$ aralkyl, optionally substituted with one, two, three, four, or five substituents Q as described herein. In certain embodiments, $R^1$ is heteroaryl, optionally substituted with one, two, three, four, or five substituents Q as described herein. In certain embodiments, $R^1$ is heterocyclyl, optionally substituted with one, two, three, four, or five substituents Q as described herein.

In certain embodiments, $R^1$ is —C(O)$R^{1a}$, wherein $R^{1a}$ is as defined herein. In certain embodiments, $R^1$ is —C(O)OR$^{1a}$, wherein $R^{1a}$ is as defined herein. In certain embodiments, $R^1$ is —C(O)NR$^{1b}$R$^{1c}$, wherein $R^{1b}$ and $R^{1c}$ are each as defined herein. In certain embodiments, $R^1$ is —C(NR$^{1a}$)NR$^{1b}$R$^{1c}$, wherein $R^{1a}$, $R^{1b}$, and $R^{1c}$ are each as defined herein. In certain embodiments, $R^1$ is —OR$^{1a}$, wherein $R^{1a}$ is as defined herein. In certain embodiments, $R^1$ is —O—$C_{1-6}$ alkyl, wherein the alkyl is optionally substituted with one, two, three, four, or five substituents Q as described herein. In certain embodiments, $R^1$ is methoxy, ethoxy, propoxy, isopropoxy, or 3-dimethylaminopropoxy. In certain embodiments, $R^1$ is —OC(O)R$^{1d}$, wherein $R^{1a}$ is as defined herein. In certain embodiments, $R^1$ is —OC(O)OR$^{1d}$, wherein $R^{1a}$ is as defined herein. In certain embodiments, $R^1$ is —OC(O)NR$^{1b}$R$^{1c}$, wherein $R^{1b}$ and $R^{1c}$ are each as defined herein. In certain embodiments, $R^1$ is —OC(=NR$^{1a}$)NR$^{1b}$R$^{1c}$, wherein $R^{1a}$, $R^{1b}$, and $R^{1c}$ are each as defined herein. In certain embodiments, $R^1$ is —OS(O)R$^{1a}$, wherein $R^{1a}$ is as defined herein. In certain embodiments, $R^1$ is —OS(O)$_2$R$^{1a}$, wherein $R^{1a}$ is as defined herein. In certain embodiments, $R^1$ is —OS(O)NR$^{1b}$R$^{1c}$, wherein $R^{1b}$ and $R^{1c}$ are each as defined herein. In certain embodiments, $R^1$ is —OS(O)$_2$NR$^{1b}$R$^{1c}$, wherein $R^{1b}$ and $R^{1c}$ are each as defined herein. In certain embodiments, $R^1$ is —NR$^{1b}$R$^{1c}$, wherein $R^{1b}$ and $R^{1c}$ are each as defined herein. In certain embodiments, $R^1$ is —NR$^{1d}$C(O)R$^{1d}$, wherein $R^{1a}$ and $R^{1d}$ are each as defined herein. In certain embodiments, $R^1$ is —NR$^{1a}$C(O)OR$^{1d}$, wherein $R^{1a}$ and $R^{1d}$ are each as defined herein. In certain embodiments, $R^1$ is —NR$^{1a}$C(O)NR$^{1b}$R$^{1c}$, wherein $R^{1a}$, $R^{1b}$, and $R^{1c}$ are each as defined herein. In certain embodiments, $R^1$ is —NR$^{1a}$C(=NR$^{1d}$)NR$^{1b}$R$^{1c}$, wherein $R^{1d}$, $R^{1b}$, $R^{1c}$, and $R^{1d}$ are each as defined herein. In certain embodiments, $R^1$ is —NR$^{1d}$S(O)R$^{1d}$, wherein $R^{1a}$ and $R^{1d}$ are each as defined herein. In certain embodiments, $R^1$ is —NR$^{1d}$S(O)$_2$R$^{1d}$, wherein $R^{1a}$ and $R^{1d}$ are each as defined herein. In certain embodiments, $R^1$ is —NR$^{1d}$S(O)NR$^{1b}$R$^{1c}$, wherein $R^{1a}$, $R^{1b}$, and $R^{1c}$ are each as defined herein. In certain embodiments, $R^1$ is —NR$^{1d}$S(O)$_2$NR$^{1b}$R$^{1c}$, wherein $R^{1a}$, $R^{1b}$, and $R^{1c}$ are each as defined herein. In certain embodiments, $R^1$ is —SR$^{1a}$, wherein $R^{1a}$ is as defined herein. In certain embodiments, $R^1$ is —S(O)R$^{1a}$, wherein $R^{1a}$ is as defined herein. In certain embodiments, $R^1$ is —S(O)$_2$R$^{1a}$, wherein $R^{1a}$ is as defined herein. In certain embodiments, $R^1$ is —S(O)NR$^{1b}$R$^{1c}$, wherein $R^{1b}$ and $R^{1c}$ are each as defined herein. In certain embodiments, $R^1$ is —S(O)$_2$NR$^{1b}$R$^{1c}$; wherein $R^{1b}$ and $R^{1c}$ are each as defined herein.

In certain embodiments, $R^2$ is hydrogen. In certain embodiments, $R^2$ is cyano. In certain embodiments, $R^2$ is halo. In certain embodiments, $R^2$ is fluoro, chloro, bromo, or iodo. In certain embodiments, $R^2$ is nitro. In certain embodiments, $R^2$ is $C_{1-6}$ alkyl, optionally substituted with one, two, three, four, or five substituents Q as described herein. In certain embodiments, $R^2$ is $C_{2-6}$ alkenyl, optionally substituted with one, two, three, four, or five substituents Q as described herein. In certain embodiments, $R^2$ is $C_{2-6}$ alkynyl, optionally substituted with one, two, three, four, or five substituents Q as described herein. In certain embodiments, $R^2$ is $C_{3-10}$ cycloalkyl, optionally substituted with one, two, three, four, or five substituents Q as described herein. In certain embodiments, $R^2$ is $C_{3-7}$ cycloalkyl, optionally substituted with one, two, three, four, or five substituents Q as described herein. In certain embodiments, $R^2$ is $C_{6-14}$ aryl, optionally substituted with one, two, three, four, or five substituents Q as described herein. In certain embodiments, $R^2$ is $C_{7-15}$ aralkyl, optionally substituted with one, two, three, four, or five substituents Q as described herein. In certain embodiments, $R^2$ is heteroaryl, optionally substituted with one, two, three, four, or five substituents Q as described herein. In certain embodiments, $R^2$ is heterocyclyl, optionally substituted with one, two, three, four, or five substituents Q as described herein.

In certain embodiments, $R^2$ is —C(O)R$^{1a}$, wherein $R^{1a}$ is as defined herein. In certain embodiments, $R^2$ is —C(O)OR$^{1a}$, wherein $R^{1a}$ is as defined herein. In certain embodiments, $R^2$ is —C(O)NR$^{1b}$R$^{1c}$, wherein $R^{1b}$ and $R^{1c}$ are each as defined herein. In certain embodiments, $R^2$ is —C(NR$^{1a}$)NR$^{1b}$R$^{1c}$, wherein $R^{1a}$, $R^{1b}$, and $R^{1c}$ are each as defined herein. In certain embodiments, $R^2$ is —OR$^{1a}$, wherein $R^{1a}$ is as defined herein. In certain embodiments, $R^1$ is —O—$C_{1-6}$ alkyl, wherein the alkyl is optionally substituted with one, two, three, four, or five substituents Q as described herein. In certain embodiments, $R^1$ is methoxy, ethoxy, propoxy, isopropoxy, or 3-dimethylaminopropoxy. In certain embodiments, $R^2$ is —OC(O)R$^{1a}$, wherein $R^{1a}$ is as defined herein. In certain embodiments, $R^2$ is —OC(O)OR$^{1a}$, wherein $R^{1a}$ is as defined herein. In certain embodiments, $R^2$ is —OC(O)NR$^{1b}$R$^{1c}$, wherein $R^{1b}$ and $R^{1c}$ are each as defined herein. In certain embodiments, $R^2$ is —OC(=NR$^{1a}$)NR$^{1b}$R$^{1c}$, wherein $R^{1a}$, $R^{1b}$, and $R^{1c}$ are each as defined herein. In certain embodiments, $R^2$ is —OS(O)R$^{1a}$, wherein $R^{1a}$ is as defined herein. In certain embodiments, $R^2$ is —OS(O)$_2$R$^{1a}$, wherein $R^{1a}$ is as defined herein. In certain embodiments, $R^2$ is —OS(O)NR$^{1b}$R$^{1c}$, wherein $R^{1b}$ and $R^{1c}$ are each as defined herein. In certain embodiments, $R^2$ is —OS(O)$_2$NR$^{1b}$R$^{1c}$, wherein R$^{1b}$ and R$^{1c}$ are each as defined herein. In certain embodiments, R$^2$ is —NR$^{1b}$R$^{1c}$, wherein R$^{1b}$ and R$^{1c}$ are each as defined herein. In certain embodiments, R$^2$ is amino (—NH$_2$). In certain embodiments, R$^2$ is —NR$^{1a}$C(O)R$^{1d}$, wherein R$^{1a}$ and R$^{1d}$ are each as defined herein. In certain embodiments, R$^2$ is —NR$^{1a}$C(O)OR$^{1d}$, wherein R$^{1a}$ and R$^{1d}$ are each as defined herein. In certain embodiments, R$^2$ is —NR$^{1a}$C(O)NR$^{1b}$R$^{1c}$, wherein R$^{1a}$, R$^{1b}$, and R$^{1c}$ are each as defined herein. In certain embodiments, R$^2$ is —NR$^{1a}$C(=NR$^{1d}$)NR$^{1b}$R$^{1c}$, wherein R$^{1a}$, R$^{1b}$, R$^{1c}$, and R$^{1d}$ are each as defined herein. In certain embodiments, R$^2$ is —NR$^{1a}$S(O)R$^{1d}$, wherein R$^{1a}$ and R$^{1d}$ are each as defined herein. In certain embodiments, R$^2$ is —NR$^{1a}$S(O)$_2$R$^{1d}$, wherein R$^{1a}$ and R$^{1d}$ are each as defined herein. In certain embodiments, R$^2$ is —NR$^{1a}$S(O)NR$^{1b}$R$^{1c}$, wherein R$^{1a}$, R$^{1b}$, and R$^{1c}$ are each as defined herein. In certain embodiments, R$^2$ is —NR$^{1a}$S(O)$_2$NR$^{1b}$R$^{1c}$, wherein R$^{1a}$, R$^{1b}$ and R$^{1c}$ are each as defined herein. In certain embodiments, R$^2$ is —SR$^{1a}$, wherein R$^{1a}$ is as defined herein. In certain embodiments, R$^2$ is —S(O)R$^{1a}$, wherein R$^{1a}$ is as defined herein. In certain embodiments, R$^2$ is —S(O)$_2$R$^{1a}$, wherein R$^{1a}$ is as defined herein. In certain embodiments, R$^2$ is —S(O)NR$^{1b}$R$^{1c}$, wherein R$^{1b}$ and R$^{1c}$ are each as defined herein. In certain embodiments, R$^2$ is —S(O)$_2$NR$^{1b}$R$^{1c}$; wherein R$^{1b}$ and R$^{1c}$ are each as defined herein.

In certain embodiments, R$^3$ is hydrogen. In certain embodiments, R$^3$ is C$_{1-6}$ alkyl, optionally substituted with one, two, three, four, or five substituents Q as described herein. In certain embodiments, R$^3$ is hydrogen, methyl, ethyl, or propyl (e.g., n-propyl, isopropyl, or 2-isopropyl).

In certain embodiments, R$^4$ is hydrogen. In certain embodiments, R$^4$ is C$_{1-6}$ alkyl, optionally substituted with one, two, three, four, or five substituents Q as described herein. In certain embodiments, R$^4$ is hydrogen, methyl, ethyl, or propyl (e.g., n-propyl, isopropyl, or 2-isopropyl).

In certain embodiments, R$^3$ and R$^4$ are linked together to form a bond. In certain embodiments, R$^3$ and R$^4$ are linked together to form C$_{1-6}$ alkylene, optionally substituted with one, two, three, four, or five substituents Q as described herein. In certain embodiments, R$^3$ and R$^4$ are linked together to form methylene, ethylene, or propylene, each optionally substituted with one, two, three, four, or five substituents Q as described herein. In certain embodiments, R$^3$ and R$^4$ are linked together to form C$_{1-6}$ heteroalkylene, optionally substituted with one, two, three, four, or five substituents Q as described herein. In certain embodiments, R$^3$ and R$^4$ are linked together to form C$_{2-6}$ alkenylene, optionally substituted with one, two, three, four, or five substituents Q as described herein. In certain embodiments, R$^3$ and R$^4$ are linked together to form C$_{2-6}$ heteroalkenylene, optionally substituted with one, two, three, four, or five substituents Q as described herein.

In certain embodiments, R$^6$ is hydrogen. In certain embodiments, R$^6$ is C$_{1-6}$ alkyl, optionally substituted with one, two, three, four, or five substituents Q as described herein. In certain embodiments, R$^6$ is C$_{1-6}$ alkyl, optionally substituted with one or more, in one embodiment, one, two, or three, halo. In certain embodiments, R$^6$ is C$_{1-6}$ alkyl, optionally substituted with one or more, in one embodiment, one, two, or three, fluoro. In certain embodiments, R$^6$ is methyl, fluoromethyl, difluoromethyl, or trifluoromethyl. In certain embodiments, R$^6$ is difluoromethyl. In certain embodiments, R$^6$ is —S—C$_{1-6}$ alkyl, wherein the alkyl is optionally substituted with one, two, three, four, or five substituents Q as described herein. In certain embodiments, R$^6$ is —S(O)—C$_{1-6}$ alkyl, wherein the alkyl is optionally substituted with one, two, three, four, or five substituents Q as described herein. In certain embodiments, R$^6$ is —SO$_2$—C$_{1-6}$ alkyl, wherein the alkyl is optionally substituted with one, two, three, four, or five substituents Q as described herein.

In certain embodiments, R$^{5a}$ is hydrogen. In certain embodiments, R$^{5a}$ is not hydrogen. In certain embodiments, R$^{5a}$ is halo. In certain embodiments, R$^{5a}$ is fluoro, chloro, bromo, or iodo. In certain embodiments, R$^{5a}$ is C$_{1-6}$ alkyl, optionally substituted with one, two, three, four, or five substituents Q as described herein. In certain embodiments, R$^{5a}$ is methyl, ethyl, propyl, or butyl, each optionally substituted with one, two, three, four, or five substituents Q as described herein. In certain embodiments, R$^{5a}$ is methyl, ethyl, n-propyl, isopropyl, n-butyl, isobutyl, or t-butyl. In certain embodiments, R$^{5a}$ is methyl. In certain embodiments, R$^{5a}$ is C$_{2-6}$ alkenyl, optionally substituted with one, two, three, four, or five substituents Q as described herein. In certain embodiments, R$^{5a}$ is C$_{2-6}$ alkynyl, optionally substituted with one, two, three, four, or five substituents Q as described herein. In certain embodiments, R$^{5a}$ is C$_{3-10}$ cycloalkyl, optionally substituted with one, two, three, four, or five substituents Q as described herein. In certain embodiments, R$^{5a}$ is C$_{3-7}$ cycloalkyl, optionally substituted with one, two, three, four, or five substituents Q as described herein. In certain embodiments, R$^{5a}$ is C$_{6-14}$ aryl, optionally substituted with one, two, three, four, or five substituents Q as described herein. In certain embodiments, R$^{5a}$ is C$_{7-15}$ aralkyl, optionally substituted with one, two, three, four, or five substituents Q as described herein. In certain embodiments, R$^{5a}$ is heteroaryl, optionally substituted with one, two, three, four, or five substituents Q as described herein. In certain embodiments, R$^{5a}$ is heterocyclyl, optionally substituted with one, two, three, four, or five substituents Q as described herein.

In certain embodiments, R$^{5a}$ is —C(O)R$^{1a}$, wherein R$^{1a}$ is as defined herein. In certain embodiments, R$^{5a}$ is —C(O)OR$^{1a}$, wherein R$^{1a}$ is as defined herein. In certain embodiments, R$^{5a}$ is C(O)OR$^{1a}$, wherein R$^{1a}$ is C$_{1-6}$ alkyl, optionally substituted with one, two, three, four, or five substituents Q as described herein. In certain embodiments, R$^{5a}$ is —C(O)OCH$_3$. In certain embodiments, R$^{5a}$ is —C(O)NR$^{1b}$R$^{1c}$, wherein R$^{1b}$ and R$^{1c}$ are each as defined herein. In certain embodiments, R$^{5a}$ is —C(NR$^{1a}$)NR$^{1b}$R$^{1c}$, wherein R$^{1a}$, R$^{1b}$, and R$^{1c}$ are each as defined herein. In certain embodiments, R$^{5a}$ is —OR$^{1a}$, wherein R$^{1a}$ is as defined herein. In certain embodiments, R$^{5a}$ is —OC(O)R$^{1a}$, wherein R$^{1a}$ is as defined herein. In certain embodiments, R$^{5a}$ is —OC(O)OR$^{1a}$, wherein R$^{1a}$ is as defined herein. In certain embodiments, R$^{5a}$ is —OC(C)NR$^{1b}$R$^{1c}$, wherein R$^{1b}$ and R$^{1c}$ are each as defined herein. In certain embodiments, R$^{5a}$ is —OC(=NR$^{1a}$)NR$^{1b}$R$^{1c}$, wherein R$^{1a}$, R$^{1b}$, and R$^{1c}$ are each as defined herein. In certain embodiments, R$^{5a}$ is —OS(O)R$^{1a}$, wherein R$^{1a}$ is as defined herein. In certain embodiments, R$^{5a}$ is —OS(O)$_2$R$^{1a}$, wherein R$^{1a}$ is as defined herein. In certain embodiments, R$^{5a}$ is —OS(O)NR$^{1b}$R$^{1c}$, wherein R$^{1b}$ and R$^{1c}$ are each as defined herein. In certain embodiments, R$^{5a}$ is —OS(O)$_2$NR$^{1b}$R$^{1c}$, wherein R$^{1b}$ and R$^{1c}$ are each as defined herein. In certain embodiments, R$^{5a}$ is —NR$^{1b}$R$^{1c}$, wherein R$^{1b}$ and R$^{1c}$ are each as defined herein. In certain embodiments, R$^{5a}$ is amino (—NH$_2$). In certain embodiments, R$^{5a}$ is —NR$^{1a}$C(O)R$^{1d}$, wherein R$^{1a}$ and R$^{1d}$ are each as defined herein. In certain embodiments, R$^{5a}$ is —NR$^{1a}$C(O)OR$^{1d}$, wherein R$^{1a}$ and R$^{1d}$ are each as defined herein. In certain embodiments, R$^{5a}$ is —NR$^{1a}$C(O)NR$^{1b}$R$^{1c}$, wherein R$^{1a}$, R$^{1b}$, and R$^{1c}$ are each as defined herein. In certain embodiments, R$^{5a}$ is —NR$^{1a}$C(=NR$^1$)NR$^{1b}$R$^{1c}$, wherein R$^{1a}$, R$^{1b}$, R$^{1c}$, and R$^{1d}$ are each as defined herein. In certain embodiments, $R^{5a}$ is —$NR^{1a}S(O)R^{1d}$, wherein $R^{1a}$ and $R^{1d}$ are each as defined herein. In certain embodiments, $R^{5a}$ is —$NR^{1a}S(O)_2R^{1d}$, wherein $R^{1a}$ and $R^{1d}$ are each as defined herein. In certain embodiments, $R^{5a}$ is —$NR^{1a}S(C)NR^{1b}R^{1c}$, wherein $R^{1a}$, $R^{1b}$, and $R^{1c}$ are each as defined herein. In certain embodiments, $R^{5a}$ is —$NR^{1a}S(O)_2NR^{1b}R^{1c}$, wherein $R^{1a}$, $R^{1b}$, and $R^{1c}$ are each as defined herein. In certain embodiments, $R^{5a}$ is —$SR^{1a}$, wherein $R^{1a}$ is as defined herein. In certain embodiments, $R^{5a}$ is —$S(O)R^{1a}$, wherein $R^{1a}$ is as defined herein. In certain embodiments, $R^{5a}$ is —$S(O)_2R^{1a}$, wherein $R^{1a}$ is as defined herein. In certain embodiments, $R^{5a}$ is —$S(C)NR^{1b}R^{1c}$, wherein $R^{1b}$ and $R^{1c}$ are each as defined herein. In certain embodiments, $R^{5a}$ is —$S(O)_2NR^{1b}R^{1c}$; wherein $R^{1b}$ and $R^{1c}$ are each as defined herein.

In certain embodiments, $R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, or heteroaryl, each of which is optionally substituted with one, two, three, four, or five substituents Q; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$. In certain embodiments, $R^{5a}$ is (a) hydrogen or halo; or (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, or heteroaryl, each of which is optionally substituted with one, two, three, four, or five substituents Q.

In certain embodiments, $R^{5b}$ is halo. In certain embodiments, $R^{5b}$ is fluoro, chloro, bromo, or iodo. In certain embodiments, $R^{5b}$ is $C_{1-6}$ alkyl, optionally substituted with one, two, three, four, or five substituents Q as described herein. In certain embodiments, $R^{5b}$ is methyl, ethyl, propyl, or butyl, each optionally substituted with one, two, three, four, or five substituents Q as described herein. In certain embodiments, $R^{5b}$ is methyl, ethyl, n-propyl, isopropyl, n-butyl, isobutyl, or t-butyl. In certain embodiments, $R^{5b}$ is methyl. In certain embodiments, $R^{5b}$ is $C_{2-6}$ alkenyl, optionally substituted with one, two, three, four, or five substituents Q as described herein. In certain embodiments, $R^{5b}$ is $C_{2-6}$ alkynyl, optionally substituted with one, two, three, four, or five substituents Q as described herein. In certain embodiments, $R^{5b}$ is $C_{3-10}$ cycloalkyl, optionally substituted with one, two, three, four, or five substituents Q as described herein. In certain embodiments, $R^{5b}$ is $C_{3-7}$ cycloalkyl, optionally substituted with one, two, three, four, or five substituents Q as described herein. In certain embodiments, $R^{5b}$ is $C_{6-14}$ aryl, optionally substituted with one, two, three, four, or five substituents Q as described herein. In certain embodiments, $R^{5b}$ is $C_{7-15}$ aralkyl, optionally substituted with one, two, three, four, or five substituents Q as described herein. In certain embodiments, $R^{5b}$ is heteroaryl, optionally substituted with one, two, three, four, or five substituents Q as described herein. In certain embodiments, $R^{5b}$ is heterocyclyl, optionally substituted with one, two, three, four, or five substituents Q as described herein. In certain embodiments, $R^{5b}$ is not heterocyclyl.

In certain embodiments, $R^{5b}$ is —$C(O)R^{1a}$, wherein $R^{1a}$ is as defined herein. In certain embodiments, $R^{5b}$ is —$C(O)OR^{1a}$, wherein $R^{1a}$ is as defined herein. In certain embodiments, $R^{5b}$ is $C(O)OR^{1a}$, wherein $R^{1a}$ is $C_{1-6}$ alkyl, optionally substituted with one, two, three, four, or five substituents Q as described herein. In certain embodiments, $R^{5b}$ is —$C(O)OCH_3$. In certain embodiments, $R^{5b}$ is $C(O)NR^{1b}R^{1c}$, wherein $R^{1b}$ and $R^{1c}$ are each as defined herein. In certain embodiments, $R^{5b}$ is —$C(NR^{1a})NR^{1b}R^{1c}$, wherein $R^{1a}$, $R^{1b}$, and $R^{1c}$ are each as defined herein. In certain embodiments, $R^{5b}$ is —$OR^{1a}$, wherein $R^{1a}$ is as defined herein. In certain embodiments, $R^{5b}$ is —$OC(O)R^{1a}$, wherein $R^{1a}$ is as defined herein. In certain embodiments, $R^{5b}$ is —$OC(O)OR^{1a}$, wherein $R^{1a}$ is as defined herein. In certain embodiments, $R^{5b}$ is —$OC(O)NR^{1b}R^{1c}$, wherein $R^{1b}$ and $R^{1c}$ are each as defined herein. In certain embodiments, $R^{5b}$ is —$OC(=NR^{1a})NR^{1b}R^{1c}$, wherein $R^{1a}$, $R^{1b}$, and $R^{1c}$ are each as defined herein. In certain embodiments, $R^{5b}$ is —$OS(O)R^{1a}$, wherein $R^{1a}$ is as defined herein. In certain embodiments, $R^{5b}$ is —$OS(O)_2R^{1a}$, wherein $R^{1a}$ is as defined herein. In certain embodiments, $R^{5b}$ is —$OS(O)NR^{1b}R^{1c}$, wherein $R^{1b}$ and $R^{1c}$ are each as defined herein. In certain embodiments, $R^{5b}$ is —$OS(O)_2NR^{1b}R^{1c}$, wherein $R^{1b}$ and $R^{1c}$ are each as defined herein. In certain embodiments, $R^{5b}$ is —$NR^{1b}R^{1c}$, wherein $R^{1b}$ and $R^{1c}$ are each as defined herein. In certain embodiments, $R^{5b}$ is amino (—$NH_2$). In certain embodiments, $R^{5b}$ is —$NR^{1a}C(O)R^{1d}$, wherein $R^{1a}$ and $R^{1d}$ are each as defined herein. In certain embodiments, $R^{5b}$ is —$NR^{1a}C(O)OR^{1d}$, wherein $R^{1a}$ and $R^{1d}$ are each as defined herein. In certain embodiments, $R^{5b}$ is —$NR^{1a}C(O)NR^{1b}R^{1c}$, wherein $R^{1a}$, $R^{1b}$, and $R^{1c}$ are each as defined herein. In certain embodiments, $R^{5b}$ is —$NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^{5b}$ is —$NR^{1a}S(O)R^{1d}$, wherein $R^{1a}$ and $R^{1d}$ are each as defined herein. In certain embodiments, $R^{5b}$ is —$NR^{1a}S(O)_2R^{1d}$, wherein $R^{1a}$ and $R^{1d}$ are each as defined herein. In certain embodiments, $R^{5b}$ is —$NR^{1a}S(O)NR^{1b}R^{1c}$, wherein $R^{1a}$, $R^{1b}$, and $R^{1c}$ are each as defined herein. In certain embodiments, $R^{5b}$ is —$NR^{1a}S(O)_2NR^{1b}R^{1c}$, wherein $R^{1a}$, $R^{1b}$ and $R^{1c}$ are each as defined herein. In certain embodiments, $R^{5b}$ is —$SR^{1a}$, wherein $R^{1a}$ is as defined herein. In certain embodiments, $R^{5b}$ is —$S(O)R^{1a}$, wherein $R^{1a}$ is as defined herein. In certain embodiments, $R^{5b}$ is —$S(O)_2R^{1a}$, wherein $R^{1a}$ is as defined herein. In certain embodiments, $R^{5b}$ is —$S(O)NR^{1b}R^{1c}$, wherein $R^{1b}$ and $R^{1c}$ are each as defined herein. In certain embodiments, $R^{5b}$ is —$S(O)_2NR^{1b}R^{1c}$; wherein $R^{1b}$ and $R^{1c}$ are each as defined herein.

In certain embodiments, $R^{5a}$ and $R^{5b}$ are each independently methyl, ethyl, n-propyl, isopropyl, n-butyl, isobutyl, or t-butyl, each optionally substituted with one, two, three, four, or five substituents Q as described herein. In certain embodiments, $R^{5a}$ and $R^{5b}$ are each independently methyl, ethyl, n-propyl, isopropyl, n-butyl, isobutyl, or t-butyl, each optionally substituted with one or more halo. In certain embodiments, $R^{5a}$ and $R^{5b}$ are each independently methyl, ethyl, n-propyl, isopropyl, n-butyl, isobutyl, or t-butyl. In certain embodiments, $R^{5a}$ and $R^{5b}$ are each methyl.

In certain embodiments, $R^{5c}$ is $C_{6-14}$ aryl, optionally substituted with one, two, three, four, or five substituents Q as described herein. In certain embodiments, $R^{5b}$ is $C_{6-14}$ aryl substituted at the 2-position with one substituent Q as described herein. In certain embodiments, $R^{5c}$ is phenyl or naphthyl, each optionally substituted with one, two, three, four, or five substituents Q as described herein. In certain embodiments, $R^{5c}$ is phenyl, naphtha-1-yl, or naphtha-2-yl, each optionally substituted with one, two, three, four, or five substituents Q as described herein. In certain embodiments, $R^{5c}$ is phenyl, 4-chlorophenyl, 4-methoxyphenyl, or naphtha-2-yl. In certain embodiments, $R^{5c}$ is heteroaryl, optionally substituted with one or more substituents as described herein. In certain embodiments, $R^{5c}$ is monocyclic heteroaryl, optionally substituted with one or more substituents as described herein. In certain embodiments, $R^{5c}$ is 5- or 6-membered heteroaryl, optionally substituted with one or more substituents as described herein. In certain embodiments, $R^{5c}$ is bicyclic heteroaryl, optionally substituted with one or more substituents as described herein.

In certain embodiments, $R^{5c}$ is $(CR^{5f}R^{5g})_n$—$(C_{6-14}$ aryl), wherein the $C_{6-14}$ aryl is optionally substituted with one, two, three, four, or five substituents Q as described herein. In certain embodiments, $R^{5c}$ is benzyl, 2-phenethyl, 3-phenylpropyl, or 4-phenylbutyl, wherein each of the phenyl moiety is optionally substituted with one, two, three, four, or five substituents Q as described herein. In certain embodiments, $R^{5c}$ is benzyl, 2-phenethyl, 3-phenylpropyl, or 4-phenylbutyl. In certain embodiments, $R^{5c}$ is benzyl, fluorobenzyl, chlorobenzyl, bromobenzyl, cyanobenzyl, methylbenzyl, or methoxybenzyl. In certain embodiments, $R^{5c}$ is (naphthalen-1-yl)methyl, (naphthalen-2-yl)methyl 2-(naphthalen-1-yl)ethyl, 2-(naphthalen-2-yl)ethyl, 3-(naphthalen-1-yl)propyl, 3-(naphthalen-2-yl)propyl, 4-(naphthalen-1-yl)butyl, or 4-(naphthalen-2-yl)butyl, wherein each of the naphthyl moiety is optionally substituted with one, two, three, four, or five substituents Q as described herein. In certain embodiments, n is 0 or 1. In one embodiment, n is 1. In one embodiment, n is 1, 2, 3, or 4. In certain embodiments, $R^{5c}$ is —$CH_2(C_{6-14}$ aryl), wherein the $C_{6-14}$ aryl is optionally substituted with one, two, three, four, or five substituents Q as described herein. In certain embodiments, $R^{5c}$ is $C(CH_3)_2(C_{6-14}$ aryl), wherein the $C_{6-14}$ aryl is optionally substituted with one, two, three, four, or five substituents Q as described herein. In certain embodiments, $R^{5c}$ is —$CH_2$-phenyl or —$CH_2$-naphthyl, wherein the phenyl or naphthyl is each optionally substituted with one, two, three, four, or five substituents Q as described herein, such as, e.g., optionally substituted with one or more F, Cl, Br, I, —CN, —$CH_3$, —$CF_3$, —$OCH_3$, or —$OCF_3$. In certain embodiments, $R^{5c}$ is —$CH_2$-phenyl, —$CH_2$-naphtha-1-yl, or —$CH_2$-naphtha-2-yl, wherein the phenyl or naphthyl is each optionally substituted with one, two, three, four, or five substituents Q as described herein, such as, e.g., optionally substituted with one or more F, Cl, Br, I, —CN, —$CH_3$, —$CF_3$, —$OCH_3$, or —$OCF_3$. In certain embodiments, $R^{5c}$ is —$CH_2$-phenyl, —$CH_2$-naphtha-1-yl, or —$CH_2$-naphtha-2-yl, wherein the phenyl or naphthyl is each optionally substituted with one or more F, Cl, Br, I, —CN, —$CH_3$, —$CF_3$, —$OCH_3$, —$OCF_3$. In other embodiments, $R^{5c}$ is —$CH_2$-phenyl, —$CH_2$-naphtha-1-yl, or —$CH_2$-naphtha-2-yl, wherein the phenyl or naphthyl is each optionally substituted with one or more F, Cl, Br, I, —CN, —$CH_3$, —$CF_3$, —$OCH_3$, —$OCF_3$, —O—($C_{1-4}$ alkylene)-N—($C_{1-4}$ alkyl)$_2$ (e.g., —O—$CH_2CH_2$—$N(CH_3)_2$), —O-heterocyclyl (e.g., —O—(N-methylpiperidinyl) or —O-piperidinyl), —O-heteroaryl (e.g., —O-pyridyl), —NH-heterocyclyl (e.g., —NH—(N-methylpiperidinyl), —NH—(N-methylpyrrolidinyl), —NH-piperidinyl, or —NH-pyrrolidinyl), —NH-heteroaryl (e.g., —NH-pyridyl), —$NCH_3$-heterocyclyl (e.g., —$NCH_3$—(N-methylpiperidinyl), —$NCH_3$—(N-methylpyrrolidinyl), —$NCH_3$-piperidinyl, or —$NCH_3$-pyrrolidinyl), —$NCH_3$-heteroaryl (e.g., —$NCH_3$-pyridyl), heterocyclyl (e.g., piperidinyl, piperazinyl, N-methylpiperidinyl, or N-methylpiperazinyl), or heteroaryl (e.g., pyridyl or imidazolyl). In certain embodiments, $R^{5c}$ is —$CH_2$-phenyl, —$C(CH_3)_2$-phenyl, —$CH_2$-(2-methylphenyl), —$CH_2$-(2-methoxylphenyl), —$CH_2$-(2-fluorophenyl), —$CH_2$-(2-chlorophenyl), —$CH_2$-(2-bromophenyl), —$CH_2$-(3-methylphenyl), —$CH_2$-(3-methoxylphenyl), —$CH_2$-(3-fluorophenyl), —$CH_2$-(3-chlorophenyl), —$CH_2$-(3-bromophenyl), —$CH_2$-(4-methylphenyl), —$CH_2$-(4-methoxylphenyl), —$CH_2$-(4-fluorophenyl), —$CH_2$-(4-chlorophenyl), —$CH_2$-(4-bromophenyl), —$CH_2$-naphtha-1-yl, or —$CH_2$-naphtha-2-yl.

In certain embodiments, $R^{5c}$ is —$(CR^{5f}R^{5g})$—$(C_{6-14}$ aryl), wherein the $C_{6-14}$ aryl is optionally substituted with one, two, three, four, or five substituents Q as described herein, and wherein $R^{5f}$ and $R^{5g}$ together with the carbon atom to which they are attached form a 3- to 6-membered cycloalkyl or heterocyclyl. In one embodiment, $R^{5c}$ is -cyclopropyl-phenyl. In one embodiment, $R^{5c}$ is -cyclobutyl-phenyl. In one embodiment, $R^{5c}$ is -cyclopentyl-phenyl. In one embodiment, $R^{5c}$ is -cyclohexyl-phenyl.

In certain embodiments, $R^{5c}$ is —$(CR^{5f}R^{5g})_n$-heteroaryl, wherein the heteroaryl is optionally substituted with one, two, three, four, or five substituents Q as described herein, wherein n is defined herein elsewhere. In certain embodiments, $R^{5c}$ is —$CH_2$-(monocyclic heteroaryl), wherein the heteroaryl is optionally substituted with one or more substituents as described herein. In certain embodiments, $R^{5c}$ is —$CH_2$-(5- or 6-membered heteroaryl), wherein the heteroaryl is optionally substituted with one or more substituents as described herein. In certain embodiments, $R^{5c}$ is —$CH_2$-(bicyclic heteroaryl), wherein the heteroaryl is optionally substituted with one or more substituents as described herein.

In certain embodiments, $R^{5d}$ is hydrogen. In certain embodiments, $R^{5d}$ is halo. In certain embodiments, $R^{5d}$ is fluoro, chloro, bromo, or iodo. In certain embodiments, $R^{5d}$ is $C_{1-6}$ alkyl, optionally substituted with one, two, three, four, or five substituents Q as described herein. In certain embodiments, $R^{5d}$ is methyl, optionally substituted with one, two, three, four, or five substituents Q as described herein. In certain embodiments, $R^{5d}$ is methyl. In certain embodiments, $R^{5d}$ is methyl, ethyl, propyl, or butyl, each optionally substituted with one, two, three, four, or five substituents Q as described herein. In certain embodiments, $R^{5d}$ is methyl, ethyl, n-propyl, isopropyl, n-butyl, isobutyl, or t-butyl. In certain embodiments, $R^{5d}$ is $C_{2-6}$ alkenyl, optionally substituted with one, two, three, four, or five substituents Q as described herein. In certain embodiments, $R^{5d}$ is $C_{2-6}$ alkynyl, optionally substituted with one, two, three, four, or five substituents Q as described herein. In certain embodiments, $R^{5d}$ is $C_{3-10}$ cycloalkyl, optionally substituted with one, two, three, four, or five substituents Q as described herein. In certain embodiments, $R^{5d}$ is $C_{6-14}$ aryl, optionally substituted with one, two, three, four, or five substituents Q as described herein. In certain embodiments, $R^{5d}$ is $C_{7-15}$ aralkyl, optionally substituted with one, two, three, four, or five substituents Q as described herein. In certain embodiments, $R^{5d}$ is heteroaryl, optionally substituted with one, two, three, four, or five substituents Q as described herein. In certain embodiments, $R^{5d}$ is heterocyclyl, optionally substituted with one, two, three, four, or five substituents Q as described herein.

In certain embodiments, $R^{5d}$ is —$C(O)R^{1a}$, wherein $R^{1a}$ is as defined herein. In certain embodiments, $R^{5d}$ is —$C(O)$ $OR^{1a}$, wherein $R^{1a}$ is as defined herein. In certain embodiments, $R^{5d}$ is $C(O)OR^{1a}$, wherein $R^{1a}$ is $C_{1-6}$ alkyl, optionally substituted with one, two, three, four, or five substituents Q as described herein. In certain embodiments, $R^{5d}$ is —$C(O)OCH_3$. In certain embodiments, $R^{5d}$ is $C(O)$ $NR^{1b}R^{1c}$, wherein $R^{1b}$ and $R^{1c}$ are each as defined herein. In certain embodiments, $R^{5d}$ is —$C(NR^{1a})NR^{1b}R^{1c}$, wherein $R^{1a}$, $R^{1b}$, and $R^{1c}$ are each as defined herein. In certain embodiments, $R^{5d}$ is $OR^{1a}$, wherein $R^{1a}$ is as defined herein. In certain embodiments, $R^{5d}$ is —$OC(O)R^{1a}$, wherein $R^{1a}$ is as defined herein. In certain embodiments, $R^{5d}$ is —$OC(O)$ $OR^{1a}$, wherein $R^{1a}$ is as defined herein. In certain embodiments, $R^{5d}$ is —OC(O)NR$^{1b}$R$^{1c}$, wherein R$^{1b}$ and R$^{1c}$ are each as defined herein. In certain embodiments, $R^{5d}$ is —OC(=NR$^{1a}$)NR$^{1b}$R$^{1c}$, wherein R$^{1a}$, R$^{1b}$, and R$^{1c}$ are each as defined herein. In certain embodiments, $R^{5d}$ is —OS(O)R$^{1a}$, wherein R$^{1a}$ is as defined herein. In certain embodiments, $R^{5d}$ is —OS(O)$_2$R$^{1a}$, wherein R$^{1a}$ is as defined herein. In certain embodiments, $R^{5d}$ is —OS(O)NR$^{1b}$R$^{1c}$, wherein R$^{1b}$ and R$^{1c}$ are each as defined herein. In certain embodiments, $R^{5d}$ is —OS(O)$_2$NR$^{1b}$R$^{1c}$, wherein R$^{1b}$ and R$^{1c}$ are each as defined herein. In certain embodiments, $R^{5d}$ is —NR$^{1b}$R$^{1c}$, wherein R$^{1b}$ and R$^{1c}$ are each as defined herein. In certain embodiments, $R^{5d}$ is amino (—NH$_2$). In certain embodiments, $R^{5d}$ is —NR$^{1a}$C(O)R$^{1d}$, wherein R$^{1a}$ and R$^{1d}$ are each as defined herein. In certain embodiments, $R^{5d}$ is —NR$^{1a}$C(O)OR$^{1d}$, wherein R$^{1a}$ and R$^{1d}$ are each as defined herein. In certain embodiments, $R^{5d}$ is —NR$^{1a}$C(O)NR$^{1b}$R$^{1c}$, wherein R$^{1a}$, R$^{1b}$, and R$^{1c}$ are each as defined herein. In certain embodiments, $R^{5d}$ is —NR$^{1a}$C(=NR$^{1d}$)NR$^{1b}$R$^{1c}$, wherein R$^{1a}$, R$^{1b}$, R$^{1c}$, and R$^{1d}$ are each as defined herein. In certain embodiments, $R^{5d}$ is —NR$^{1a}$S(O)R$^{1d}$, wherein R$^{1a}$ and R$^{1d}$ are each as defined herein. In certain embodiments, $R^{5d}$ is —NR$^{1a}$S(O)$_2$R$^{1d}$, wherein R$^{1a}$ and R$^{1d}$ are each as defined herein. In certain embodiments, $R^{5d}$ is —NR$^{1a}$S(O)NR$^{1b}$R$^{1c}$, wherein R$^{1a}$, R$^{1b}$, and R$^{1c}$ are each as defined herein. In certain embodiments, $R^{5d}$ is —NR$^{1a}$S(O)$_2$NR$^{1b}$R$^{1c}$, wherein R$^{1a}$, R$^{1b}$, and R$^{1c}$ are each as defined herein. In certain embodiments, $R^{5d}$ is —SR$^{1a}$, wherein R$^{1a}$ is as defined herein. In certain embodiments, $R^{5d}$ is —S(O)R$^{1a}$, wherein R$^{1a}$ is as defined herein. In certain embodiments, $R^{5d}$ is —S(O)$_2$R$^{1a}$, wherein R$^{1a}$ is as defined herein. In certain embodiments, $R^{5d}$ is —S(O)NR$^{1b}$R$^{1c}$, wherein R$^{1b}$ and R$^{1c}$ are each as defined herein. In certain embodiments, $R^{5d}$ is —S(O)$_2$NR$^{1b}$R$^{1c}$; wherein R$^{1b}$ and R$^{1c}$ are each as defined herein.

In certain embodiments, $R^{5e}$ is hydrogen. In certain embodiments, $R^{5e}$ is halo. In certain embodiments, $R^{5e}$ is fluoro, chloro, bromo, or iodo. In certain embodiments, $R^{5e}$ is C$_{1-6}$ alkyl, optionally substituted with one, two, three, four, or five substituents Q as described herein. In certain embodiments, $R^{5e}$ is methyl, optionally substituted with one, two, three, four, or five substituents Q as described herein. In certain embodiments, $R^{5e}$ is methyl. In certain embodiments, $R^{5e}$ is methyl, ethyl, propyl, or butyl, each optionally substituted with one, two, three, four, or five substituents Q as described herein. In certain embodiments, $R^{5e}$ is methyl, ethyl, n-propyl, isopropyl, n-butyl, isobutyl, or t-butyl. In certain embodiments, $R^{5e}$ is C$_{2-6}$ alkenyl, optionally substituted with one, two, three, four, or five substituents Q as described herein. In certain embodiments, $R^{5e}$ is C$_{2-6}$ alkynyl, optionally substituted with one, two, three, four, or five substituents Q as described herein. In certain embodiments, $R^{5e}$ is C$_{3-10}$ cycloalkyl, optionally substituted with one, two, three, four, or five substituents Q as described herein. In certain embodiments, $R^{5e}$ is C$_{6-14}$ aryl, optionally substituted with one, two, three, four, or five substituents Q as described herein. In certain embodiments, $R^{5e}$ is C$_{7-15}$ aralkyl, optionally substituted with one, two, three, four, or five substituents Q as described herein. In certain embodiments, $R^{5e}$ is heteroaryl, optionally substituted with one, two, three, four, or five substituents Q as described herein. In certain embodiments, $R^{5e}$ is heterocyclyl, optionally substituted with one, two, three, four, or five substituents Q as described herein.

In certain embodiments, $R^{5e}$ is —C(O)R$^{1a}$, wherein R$^{1a}$ is as defined herein. In certain embodiments, $R^{5e}$ is —C(O)OR$^{1a}$, wherein R$^{1a}$ is as defined herein. In certain embodiments, $R^{5e}$ is C(O)OR$^{1a}$, wherein R$^{1a}$ is C$_{1-6}$ alkyl, optionally substituted with one, two, three, four, or five substituents Q as described herein. In certain embodiments, $R^{5e}$ is —C(O)OCH$_3$. In certain embodiments, $R^{5e}$ is C(O)NR$^{1b}$R$^{1c}$ wherein R$^{1b}$ and R$^{1c}$ are each as defined herein. In certain embodiments, $R^{5e}$ is C(NR$^{1a}$)NR$^{1b}$R$^{1c}$, wherein R$^{1a}$, R$^{1b}$, and R$^{1c}$ are each as defined herein. In certain embodiments, $R^{5e}$ is —OR$^{1a}$, wherein R$^{1a}$ is as defined herein. In certain embodiments, $R^{5e}$ is —OC(O)R$^{1a}$, wherein R$^{1a}$ is as defined herein. In certain embodiments, $R^{5e}$ is —OC(O)OR$^{1a}$, wherein R$^{1a}$ is as defined herein. In certain embodiments, $R^{5e}$ is —OC(O)NR$^{1b}$R$^{1c}$, wherein R$^{1b}$ and R$^{1c}$ are each as defined herein. In certain embodiments, $R^{5e}$ is —OC(=NR$^{1a}$)NR$^{1b}$R$^{1c}$, wherein R$^{1a}$, R$^{1b}$, and R$^{1c}$ are each as defined herein. In certain embodiments, $R^{5e}$ is —OS(O)R$^{1a}$, wherein R$^{1a}$ is as defined herein. In certain embodiments, $R^{5e}$ is —OS(O)$_2$R$^{1a}$, wherein R$^{1a}$ is as defined herein. In certain embodiments, $R^{5e}$ is —OS(O)NR$^{1b}$R$^{1c}$, wherein R$^{1b}$ and R$^{1c}$ are each as defined herein. In certain embodiments, $R^{5e}$ is —OS(O)$_2$NR$^{1b}$R$^{1c}$, wherein R$^{1b}$ and R$^{1c}$ are each as defined herein. In certain embodiments, $R^{5e}$ is —NR$^{1b}$R$^{1c}$, wherein R$^{1b}$ and R$^{1c}$ are each as defined herein. In certain embodiments, $R^{5e}$ is amino (—NH$_2$). In certain embodiments, $R^{5e}$ is —NR$^{1a}$C(O)R$^{1d}$, wherein R$^{1a}$ and R$^{1d}$ are each as defined herein. In certain embodiments, $R^{5e}$ is —NR$^{1a}$C(O)OR$^{1d}$, wherein R$^{1a}$ and R$^{1d}$ are each as defined herein. In certain embodiments, $R^{5e}$ is —NR$^{1a}$C(O)NR$^{1b}$R$^{1c}$, wherein R$^{1a}$, R$^{1b}$, and R$^{1c}$ are each as defined herein. In certain embodiments, $R^{5e}$ is —NR$^{1a}$C(=NR$^{1d}$)NR$^{1b}$R$^{1c}$, wherein R$^{1a}$, R$^{1b}$, R$^{1c}$, and R$^{1d}$ are each as defined herein. In certain embodiments, $R^{5e}$ is NR$^{1a}$S(O)R$^{1d}$, wherein R$^{1a}$ and R$^{1d}$ are each as defined herein. In certain embodiments, $R^{5e}$ is —NR$^{1a}$S(O)$_2$R$^{1d}$, wherein R$^{1a}$ and R$^{1d}$ are each as defined herein. In certain embodiments, $R^{5e}$ is —NR$^{1a}$S(O)NR$^{1b}$R$^{1c}$, wherein R$^{1a}$, R$^{1b}$, and R$^{1c}$ are each as defined herein. In certain embodiments, $R^{5e}$ is —NR$^{1a}$S(O)$_2$NR$^{1b}$R$^{1c}$, wherein R$^{1a}$, R$^{1b}$, and R$^{1c}$ are each as defined herein. In certain embodiments, $R^{5e}$ is SR$^{1a}$, wherein R$^{1a}$ is as defined herein. In certain embodiments, $R^{5e}$ is —S(O)R$^{1a}$, wherein R$^{1a}$ is as defined herein. In certain embodiments, $R^{5e}$ is —S(O)$_2$R$^{1a}$, wherein R$^{1a}$ is as defined herein. In certain embodiments, $R^{5e}$ is —S(O)NR$^{1b}$R$^{1c}$, wherein R$^{1b}$ and R$^{1c}$ are each as defined herein. In certain embodiments, $R^{5e}$ is —S(O)$_2$NR$^{1b}$R$^{1c}$; wherein R$^{1b}$ and R$^{1c}$ are each as defined herein.

In certain embodiments, $R^{5f}$ is hydrogen. In certain embodiments, $R^{5f}$ is halo. In certain embodiments, $R^{5f}$ is fluoro, chloro, bromo, or iodo. In certain embodiments, $R^{5f}$ is C$_{1-6}$ alkyl, optionally substituted with one, two, three, four, or five substituents Q as described herein. In certain embodiments, $R^{5f}$ is methyl, optionally substituted with one, two, three, four, or five substituents Q as described herein. In certain embodiments, $R^{5f}$ is methyl. In certain embodiments, $R^{5f}$ is methyl, ethyl, propyl, or butyl, each optionally substituted with one, two, three, four, or five substituents Q as described herein. In certain embodiments, $R^{5f}$ is methyl, ethyl, n-propyl, isopropyl, n-butyl, isobutyl, or t-butyl. In certain embodiments, $R^{5f}$ is C$_{2-6}$ alkenyl, optionally substituted with one, two, three, four, or five substituents Q as described herein. In certain embodiments, $R^{5f}$ is C$_{2-6}$ alkynyl, optionally substituted with one, two, three, four, or five substituents Q as described herein. In certain embodiments, $R^{5f}$ is C$_{3-10}$ cycloalkyl, optionally substituted with one, two, three, four, or five substituents Q as described herein. In certain embodiments, $R^{5f}$ is C$_{6-14}$ aryl, optionally substituted with one, two, three, four, or five substituents Q as described herein. In certain embodiments, $R^{5f}$ is C$_{7-15}$ aralkyl, optionally substituted with one, two, three, four, or five substituents Q as described herein. In certain embodiments, $R^{5f}$ is heteroaryl, optionally substituted with one, two, three, four, or five substituents Q as described herein. In certain embodiments, $R^{5f}$ is heterocyclyl, optionally substituted with one, two, three, four, or five substituents Q as described herein.

In certain embodiments, $R^{5f}$ is —C(O)$R^{1a}$, wherein $R^{1a}$ is as defined herein. In certain embodiments, $R^{5f}$ is —C(O)OR$^{1a}$, wherein $R^{1a}$ is as defined herein. In certain embodiments, $R^{5f}$ is C(O)OR$^{1a}$, wherein $R^{1a}$ is $C_{1-6}$ alkyl, optionally substituted with one, two, three, four, or five substituents Q as described herein. In certain embodiments, $R^{5f}$ is —C(O)OCH$_3$. In certain embodiments, $R^{5f}$ is —C(O)NR wherein $R^{1b}$ and $R^{1c}$ are each as defined herein. In certain embodiments, $R^{5f}$ is —C(NR$^{1a}$)NR$^{1b}$R$^{1c}$, wherein $R^{1a}$, $R^{1b}$, and $R^{1c}$ are each as defined herein. In certain embodiments, $R^{5f}$ is —OR$^{1a}$, wherein $R^{1a}$ is as defined herein. In certain embodiments, $R^{5f}$ is —OC(O)R$^{1a}$, wherein $R^{1a}$ is as defined herein. In certain embodiments, $R^{5f}$ is —OC(O)OR$^{1a}$, wherein $R^{1a}$ is as defined herein. In certain embodiments, $R^{5f}$ is —OC(O)NR$^{1b}$R$^{1c}$, wherein $R^{1b}$ and $R^{1c}$ are each as defined herein. In certain embodiments, $R^{5f}$ is —OC(=NR$^{1a}$)NR$^{1b}$R$^{1c}$, wherein $R^{1a}$, $R^{1b}$, and $R^{1c}$ are each as defined herein. In certain embodiments, $R^{5f}$ is —OS(O)R$^{1a}$, wherein $R^{1a}$ is as defined herein. In certain embodiments, $R^{5f}$ is —OS(O)$_2$R$^{1a}$, wherein $R^{1a}$ is as defined herein. In certain embodiments, $R^{5f}$ is —OS(O)NR$^{1b}$R$^{1c}$, wherein $R^{1b}$ and $R^{1c}$ are each as defined herein. In certain embodiments, $R^{5f}$ is —OS(O)$_2$NR$^{1b}$R$^{1c}$, wherein $R^{1b}$ and $R^{1c}$ are each as defined herein. In certain embodiments, $R^{5f}$ is —NR$^{1b}$R$^{1c}$, wherein $R^{1b}$ and $R^{1c}$ are each as defined herein. In certain embodiments, $R^{5f}$ is amino (—NH$_2$). In certain embodiments, $R^{5f}$ is —NR$^{1a}$C(O)R$^{1d}$, wherein $R^{1a}$ and $R^{1d}$ are each as defined herein. In certain embodiments, $R^{5f}$ is —NR$^{1a}$C(O)OR$^{1d}$, wherein $R^{1a}$ and $R^{1d}$ are each as defined herein. In certain embodiments, $R^{5f}$ is —NR$^{1a}$C(O)NR$^{1b}$R$^{1c}$, wherein $R^{1a}$, $R^{1b}$, and $R^{1c}$ are each as defined herein. In certain embodiments, $R^{5f}$ is —NR$^{1a}$C(=NR$^{1d}$)NR$^{1b}$R$^{1c}$, wherein $R^{1a}$, $R^{1b}$, $R^{1c}$, and $R^{1d}$ are each as defined herein. In certain embodiments, $R^{5f}$ is —NR$^{1a}$S(O)R$^{1d}$, wherein $R^{1a}$ and $R^{1d}$ are each as defined herein. In certain embodiments, $R^{5f}$ is —NR$^{1a}$S(O)$_2$R$^{1d}$, wherein $R^{1a}$ and $R^{1d}$ are each as defined herein. In certain embodiments, $R^{5f}$ is —NR$^{1a}$S(O)NR$^{1b}$R$^{1c}$, wherein $R^{1a}$, $R^{1b}$, and $R^{1c}$ are each as defined herein. In certain embodiments, $R^{5f}$ is —NR$^{1a}$S(O)$_2$NR$^{1b}$R$^{1c}$, wherein $R^{1a}$, $R^{1b}$, and $R^{1c}$ are each as defined herein. In certain embodiments, $R^{5f}$ is —SR$^{1a}$, wherein $R^{1a}$ is as defined herein. In certain embodiments, $R^{5f}$ is —S(O)R$^{1a}$, wherein $R^{1a}$ is as defined herein. In certain embodiments, $R^{5f}$ is —S(O)$_2$R$^{1a}$, wherein $R^{1a}$ is as defined herein. In certain embodiments, $R^{5f}$ is —S(O)NR$^{1b}$R$^{1c}$, wherein $R^{1b}$ and $R^{1c}$ are each as defined herein. In certain embodiments, $R^{5f}$ is —S(O)$_2$NR$^{1b}$R$^{1c}$; wherein $R^{1b}$ and $R^{1c}$ are each as defined herein.

In certain embodiments, $R^{5g}$ is hydrogen. In certain embodiments, $R^{5g}$ is halo. In certain embodiments, $R^{5g}$ is fluoro, chloro, bromo, or iodo. In certain embodiments, $R^{5g}$ is $C_{1-6}$ alkyl, optionally substituted with one, two, three, four, or five substituents Q as described herein. In certain embodiments, $R^{5g}$ is methyl, optionally substituted with one, two, three, four, or five substituents Q as described herein. In certain embodiments, $R^{5g}$ is methyl. In certain embodiments, $R^{5g}$ is methyl, ethyl, propyl, or butyl, each optionally substituted with one, two, three, four, or five substituents Q as described herein. In certain embodiments, $R^{5g}$ is methyl, ethyl, n-propyl, isopropyl, n-butyl, isobutyl, or t-butyl. In certain embodiments, $R^{5g}$ is $C_{2-6}$ alkenyl, optionally substituted with one, two, three, four, or five substituents Q as described herein. In certain embodiments, $R^{5g}$ is $C_{2-6}$ alkynyl, optionally substituted with one, two, three, four, or five substituents Q as described herein. In certain embodiments, $R^{5g}$ is $C_{3-10}$ cycloalkyl, optionally substituted with one, two, three, four, or five substituents Q as described herein. In certain embodiments, $R^{5g}$ is $C_{6-14}$ aryl, optionally substituted with one, two, three, four, or five substituents Q as described herein. In certain embodiments, $R^{5g}$ is $C_{7-15}$ aralkyl, optionally substituted with one, two, three, four, or five substituents Q as described herein. In certain embodiments, $R^{5g}$ is heteroaryl, optionally substituted with one, two, three, four, or five substituents Q as described herein. In certain embodiments, $R^{5g}$ is heterocyclyl, optionally substituted with one, two, three, four, or five substituents Q as described herein.

In certain embodiments, $R^{5g}$ is —C(O)R$^{1a}$, wherein $R^{1a}$ is as defined herein. In certain embodiments, $R^{5g}$ is —C(O)OR$^{1a}$, wherein $R^{1a}$ is as defined herein. In certain embodiments, $R^{5g}$ is C(O)OR$^{1a}$, wherein $R^{1a}$ is $C_{1-6}$ alkyl, optionally substituted with one, two, three, four, or five substituents Q as described herein. In certain embodiments, $R^{5g}$ is —C(O)OCH$_3$. In certain embodiments, $R^{5g}$ is —C(O)NR wherein $R^{1b}$ and $R^{1c}$ are each as defined herein. In certain embodiments, $R^{5g}$ is —C(NR$^{1a}$)NR$^{1b}$R$^{1c}$, wherein $R^{1a}$, $R^{1b}$, and $R^{1c}$ are each as defined herein. In certain embodiments, $R^{5g}$ is —OR$^{1a}$, wherein $R^{1a}$ is as defined herein. In certain embodiments, $R^{5g}$ is —OC(O)R$^{1a}$, wherein $R^{1a}$ is as defined herein. In certain embodiments, $R^{5g}$ is —OC(O)OR$^{1a}$, wherein $R^{1a}$ is as defined herein. In certain embodiments, $R^{5g}$ is —OC(O)NR$^{1b}$R$^{1c}$, wherein $R^{1b}$ and $R^{1c}$ are each as defined herein. In certain embodiments, $R^{5g}$ is —OC(=NR$^{1a}$)NR$^{1b}$R$^{1c}$, wherein $R^{1a}$, $R^{1b}$, and $R^{1c}$ are each as defined herein. In certain embodiments, $R^{5g}$ is —OS(O)R$^{1a}$, wherein $R^{1a}$ is as defined herein. In certain embodiments, $R^{5g}$ is —OS(O)$_2$R$^{1a}$, wherein $R^{1a}$ is as defined herein. In certain embodiments, $R^{5g}$ is —OS(O)NR$^{1b}$R$^{1c}$, wherein $R^{1b}$ and $R^{1c}$ are each as defined herein. In certain embodiments, $R^{5g}$ is —OS(O)$_2$NR$^{1b}$R$^{1c}$, wherein $R^{1b}$ and $R^{1c}$ are each as defined herein. In certain embodiments, $R^{5g}$ is NR$^{1b}$R$^{1c}$, wherein $R^{1b}$ and $R^{1c}$ are each as defined herein. In certain embodiments, $R^{5g}$ is amino (—NH$_2$). In certain embodiments, $R^{5g}$ is —NR$^{1a}$C(O)R$^{1d}$, wherein $R^{1a}$ and $R^{1d}$ are each as defined herein. In certain embodiments, $R^{5g}$ is —NR$^{1a}$C(O)OR$^{1d}$, wherein $R^{1a}$ and $R^{1d}$ are each as defined herein. In certain embodiments, $R^{5g}$ is —NR$^{1a}$C(O)NR$^{1b}$R$^{1c}$, wherein $R^{1a}$, $R^{1b}$, and $R^{1c}$ are each as defined herein. In certain embodiments, $R^{5g}$ is —NR$^{1a}$C(=NR$^{1d}$)NR$^{1b}$R$^{1c}$, wherein $R^{1a}$, $R^{1b}$, $R^{1c}$, and $R^{1d}$ are each as defined herein. In certain embodiments, $R^{5g}$ is NR$^{1a}$S(O)R$^{1d}$, wherein $R^{1a}$ and $R^{1d}$ are each as defined herein. In certain embodiments, $R^{5g}$ is —NR$^{1a}$S(O)$_2$R$^{1d}$, wherein $R^{1a}$ and $R^{1d}$ are each as defined herein. In certain embodiments, $R^{5g}$ is —NR$^{1a}$S(O)NR$^{1b}$R$^{1c}$, wherein $R^{1a}$, $R^{1b}$, and $R^{1c}$ are each as defined herein. In certain embodiments, $R^{5g}$ is —NR$^{1a}$S(O)$_2$NR$^{1b}$R$^{1c}$, wherein $R^{1a}$, $R^{1b}$ and $R^{1c}$ are each as defined herein. In certain embodiments, $R^{5g}$ is —SR$^{1a}$, wherein $R^{1a}$ is as defined herein. In certain embodiments, $R^{5g}$ is —S(O)R$^{1a}$, wherein $R^{1a}$ is as defined herein. In certain embodiments, $R^{5g}$ is —S(O)$_2$R$^{1a}$, wherein $R^{1a}$ is as defined herein. In certain embodiments, $R^{5g}$ is —S(O)NR$^{1b}$R$^{1c}$, wherein $R^{1b}$ and $R^{1c}$ are each as defined herein. In certain embodiments, $R^{5g}$ is —S(O)$_2$NR$^{1b}$R$^{1c}$; wherein $R^{1b}$ and $R^{1c}$ are each as defined herein.

In certain embodiments, when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a $C_{3-7}$ cycloalkyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclopropyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclobutyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclopentyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclohexyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cycloheptyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclopropyl.

In certain embodiments, when one occurrence of $R^{5f}$ and one occurrence of $R^{5g}$ are attached to the same carbon atom, the $R^{5f}$ and $R^{5g}$ together with the carbon atom to which they are attached form a heterocyclyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a 3-membered heterocyclyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a 4-membered heterocyclyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a 5-membered heterocyclyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a 6-membered heterocyclyl, optionally substituted with one, two, three, four, or five substituents Q as described herein.

In certain embodiments, $R^{7a}$ is hydrogen. In certain embodiments, $R^{7a}$ is cyano. In certain embodiments, $R^{7a}$ is halo. In certain embodiments, $R^{7a}$ is fluoro, chloro, bromo, or iodo. In certain embodiments, $R^{7a}$ is nitro. In certain embodiments, $R^{7a}$ is $C_{1-6}$ alkyl, optionally substituted with one, two, three, or four substituents $Q^a$ as described herein. In certain embodiments, $R^{7a}$ is $C_{2-6}$ alkenyl, optionally substituted with one, two, three, or four substituents $Q^a$ as described herein. In certain embodiments, $R^{7a}$ is $C_{2-6}$ alkynyl, optionally substituted with one, two, three, or four substituents $Q^a$ as described herein. In certain embodiments, $R^{7a}$ is $C_{3-7}$ cycloalkyl, optionally substituted with one, two, three, or four substituents $Q^a$ as described herein. In certain embodiments, $R^{7a}$ is $C_{3-10}$ cycloalkyl, optionally substituted with one, two, three, or four substituents $Q^a$ as described herein. In certain embodiments, $R^{7a}$ is $C_{6-14}$ aryl, optionally substituted with one, two, three, or four substituents $Q^a$ as described herein. In certain embodiments, $R^{7a}$ is phenyl, optionally substituted with one, two, three, or four substituents $Q^a$ as described herein. In certain embodiments, $R^{7a}$ is phenyl, optionally substituted with one or more substituents, each of which is selected independently from the group consisting of fluoro, chloro, bromo, methyl, and methoxy. In certain embodiments, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-fluorophenyl, 4-chlorophenyl, 4-bromophenyl, 4-methoxyphenyl. In certain embodiments, $R^{7a}$ is $C_{7-15}$ aralkyl, optionally substituted with one, two, three, or four substituents $Q^a$ as described herein. In certain embodiments, $R^{7a}$ is heteroaryl, optionally substituted with one, two, three, or four substituents $Q^a$ as described herein. In certain embodiments, $R^{7a}$ is monocyclic heteroaryl, optionally substituted with one, two, three, or four substituents $Q^a$ as described herein. In certain embodiments, $R^{7a}$ is 5-membered heteroaryl, optionally substituted with one, two, three, or four substituents $Q^a$ as described herein. In certain embodiments, $R^{7a}$ is imidazolyl or pyrozolyl, optionally substituted with one, two, three, or four substituents $Q^a$ as described herein. In certain embodiments, $R^{7a}$ is imidazol-1-yl, pyrozol-4-yl, 1-methyl-pyrozol-4-yl, or 2-methylpyrozol-3-yl. In certain embodiments, $R^{7a}$ is 6-membered heteroaryl, optionally substituted with one, two, three, or four substituents $Q^a$ as described herein. In certain embodiments, $R^{7a}$ is pyridinyl, optionally substituted with one, two, three, or four substituents $Q^a$ as described herein. In certain embodiments, $R^{7a}$ is pyridin-2-yl, pyridin-3-yl, pyridin-4-yl, 2-methylpyridin-4-yl, or 2-methoxypyridin-4-yl. In certain embodiments, $R^{7a}$ is heterocyclyl, optionally substituted with one, two, three, or four substituents $Q^a$ as described herein. In certain embodiments, $R^{7a}$ is monocyclic heterocyclyl, optionally substituted with one, two, three, or four substituents $Q^a$ as described herein. In certain embodiments, $R^{7a}$ is 5-membered heterocyclyl, optionally substituted with one, two, three, or four substituents $Q^a$ as described herein. In certain embodiments, $R^{7a}$ is 6-membered heterocyclyl, optionally substituted with one, two, three, or four substituents $Q^a$ as described herein. In certain embodiments, $R^{7a}$ is piperidinyl or piperazinyl, optionally substituted with one, two, three, or four substituents $Q^a$ as described herein. In certain embodiments, $R^{7a}$ is 1-methylpiperidin-4-yl, or 4-methylpiperazin-1-yl.

In certain embodiments, $R^{7a}$ is —C(O)$R^a$, wherein $R^a$ is as defined herein. In certain embodiments, $R^{7a}$ is —C(O)O$R^a$, wherein $R^a$ is as defined herein. In certain embodiments, $R^{7a}$ is —C(O)N$R^bR^c$, wherein $R^b$ and $R^c$ are each as defined herein. In certain embodiments, $R^{7a}$ is —C(N$R^a$)N$R^bR^c$, wherein $R^a$, $R^b$, and $R^c$ are each as defined herein. In certain embodiments, $R^{7a}$ is —O$R^a$, wherein $R^a$ is as defined herein. In certain embodiments, $R^a$ is —O—$C_{1-6}$ alkyl, wherein the alkyl is optionally substituted with one, two, three, or four substituents $Q^a$ as described herein. In certain embodiments, $R^a$ is methoxy, ethoxy, propoxy, isopropoxy, or 3-dimethylaminopropoxy. In certain embodiments, $R^{7a}$ is —OC(O)$R^a$, wherein $R^a$ is as defined herein. In certain embodiments, $R^{7a}$ is —OC(O)O$R^a$, wherein $R^a$ is as defined herein. In certain embodiments, $R^{7a}$ is —OC(O)N$R^bR^c$, wherein $R^b$ and $R^c$ are each as defined herein. In certain embodiments, $R^{7a}$ is —OC(=N$R^a$)N$R^bR^c$, wherein $R^a$, $R^b$, and $R^c$ are each as defined herein. In certain embodiments, $R^{7a}$ is —OS(O)$R^a$, wherein $R^a$ is as defined herein. In certain embodiments, $R^{7a}$ is —OS(O)$_2R^a$, wherein $R^a$ is as defined herein. In certain embodiments, $R^{7a}$ is —OS(O)N$R^bR^c$, wherein $R^b$ and $R^c$ are each as defined herein. In certain embodiments, $R^{7a}$ is —OS(O)$_2$N$R^bR^c$, wherein $R^b$ and $R^c$ are each as defined herein. In certain embodiments, $R^{7a}$ is —N$R^bR^c$, wherein $R^b$ and $R^c$ are each as defined herein. In certain embodiments, $R^{7a}$ is amino (—NH$_2$). In certain embodiments, $R^{7a}$ is —N$R^a$C(O)$R^d$, wherein $R^a$ and $R^d$ are each as defined herein. In certain embodiments, $R^{7a}$ is —N$R^a$C(O)O$R^d$, wherein $R^a$ and $R^d$ are each as defined herein. In certain embodiments, $R^{7a}$ is —N$R^a$C(O)N$R^bR^c$, wherein $R^a$, $R^b$, and $R^c$ are each as defined herein. In certain embodiments, $R^{7a}$ is —N$R^a$C(=N$R^d$)N$R^bR^c$, wherein $R^a$, $R^b$, $R^c$, and $R^d$ are each as defined herein. In certain embodiments, $R^{7a}$ is —N$R^a$S(O)$R^d$, wherein $R^a$ and $R^d$ are each as defined herein. In certain embodiments, $R^{7a}$ is —N$R^a$S(O)$_2R^d$, wherein $R^a$ and $R^d$ are each as defined herein. In certain embodiments, $R^{7a}$ is —N$R^a$S(O)N$R^bR^c$, wherein $R^a$, $R^b$, and $R^c$ are each as defined herein. In certain embodiments, $R^{7a}$ is —N$R^a$S(O)$_2$N$R^bR^c$, wherein $R^a$, $R^b$, and $R^c$ are each as defined herein. In certain embodiments, $R^{7a}$ is —S$R^a$, wherein $R^a$ is as defined herein. In certain embodiments, $R^{7a}$ is —S(O)$R^a$, wherein $R^a$ is as defined herein. In certain embodiments, $R^{7a}$ is —S(O)$_2R^a$, wherein $R^a$ is as defined herein. In certain embodiments, $R^{7a}$ is —S(O)N$R^bR^c$, wherein $R^b$ and $R^c$ are each as defined herein. In certain embodiments, $R^{7a}$ is —S(O)$_2$N$R^bR^c$; wherein $R^b$ and $R^c$ are each as defined herein.

In certain embodiments, $R^{7a}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$. In certain embodiments, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, $R^{7b}$ is hydrogen. In certain embodiments, $R^{7a}$ is cyano. In certain embodiments, $R^{7b}$ is halo. In certain embodiments, $R^{7b}$ is fluoro, chloro, bromo, or iodo. In certain embodiments, $R^{7b}$ is nitro. In certain embodiments, $R^{7b}$ is $C_{1-6}$ alkyl, optionally substituted with one, two, three, or four substituents $Q^a$ as described herein. In certain embodiments, $R^{7b}$ is $C_{2-6}$ alkenyl, optionally substituted with one, two, three, or four substituents $Q^a$ as described herein. In certain embodiments, $R^{7b}$ is $C_{2-6}$ alkynyl, optionally substituted with one, two, three, or four substituents $Q^a$ as described herein. In certain embodiments, $R^{7a}$ is $C_{3-10}$ cycloalkyl, optionally substituted with one, two, three, or four substituents $Q^a$ as described herein. In certain embodiments, $R^{7b}$ is $C_{3-7}$ cycloalkyl, optionally substituted with one, two, three, or four substituents $Q^a$ as described herein. In certain embodiments, $R^{7b}$ is $C_{6-14}$ aryl, optionally substituted with one, two, three, or four substituents $Q^a$ as described herein. In certain embodiments, $R^{7b}$ is $C_{7-15}$ aralkyl, optionally substituted with one, two, three, or four substituents $Q^a$ as described herein. In certain embodiments, $R^{7a}$ is heteroaryl, optionally substituted with one, two, three, or four substituents $Q^a$ as described herein. In certain embodiments, $R^{7b}$ is heterocyclyl, optionally substituted with one, two, three, or four substituents $Q^a$ as described herein.

In certain embodiments, $R^{7b}$ is —C(O)$R^a$, wherein $R^a$ is as defined herein. In certain embodiments, $R^{7b}$ is —C(O)O$R^a$, wherein $R^a$ is as defined herein. In certain embodiments, $R^{7b}$ is —C(O)N$R^bR^c$, wherein $R^b$ and $R^c$ are each as defined herein. In certain embodiments, $R^{7b}$ is —C(N$R^a$)N$R^bR^c$, wherein $R^a$, $R^b$, and $R^c$ are each as defined herein. In certain embodiments, $R^{7b}$ is —O$R^a$, wherein $R^a$ is as defined herein. In certain embodiments, $R^a$ is —O—$C_{1-6}$ alkyl, wherein the alkyl is optionally substituted with one, two, three, or four substituents $Q^a$ as described herein. In certain embodiments, $R^a$ is methoxy, ethoxy, propoxy, isopropoxy, or 3-dimethylaminopropoxy. In certain embodiments, $R^{7b}$ is —OC(O)$R^a$, wherein $R^a$ is as defined herein. In certain embodiments, $R^{7b}$ is —OC(O)O$R^a$, wherein $R^a$ is as defined herein. In certain embodiments, $R^{7b}$ is —OC(O)N$R^bR^c$, wherein $R^b$ and are each as defined herein. In certain embodiments, $R^{7b}$ is —OC(=N$R^a$)N$R^bR^c$, wherein $R^a$, $R^b$, and $R^c$ are each as defined herein. In certain embodiments, $R^{7b}$ is —OS(O)$R^a$, wherein $R^a$ is as defined herein. In certain embodiments, $R^{7b}$ is —OS(O)$_2R^a$, wherein $R^a$ is as defined herein. In certain embodiments, $R^{7b}$ is —OS(O)N$R^bR^c$, wherein $R^b$ and are each as defined herein. In certain embodiments, $R^{7b}$ is —OS(O)$_2$N$R^bR^c$, wherein $R^b$ and are each as defined herein. In certain embodiments, $R^{7b}$ is —N$R^bR^c$, wherein $R^b$ and $R^c$ are each as defined herein. In certain embodiments, $R^{7b}$ is amino (—NH$_2$). In certain embodiments, $R^{7b}$ is —N$R^a$C(O)$R^d$, wherein $R^a$ and $R^d$ are each as defined herein. In certain embodiments, $R^{7b}$ is —N$R^a$C(O)O$R^d$, wherein $R^a$ and $R^d$ are each as defined herein. In certain embodiments, $R^{7b}$ is —N$R^a$C(O)N$R^bR^c$, wherein $R^a$, $R^b$, and $R^c$ are each as defined herein. In certain embodiments, $R^{7b}$ is —N$R^a$C(=N$R^d$)N$R^bR^c$, wherein $R^a$, $R^b$, $R^c$, and $R^d$ are each as defined herein. In certain embodiments, $R^{7b}$ is —N$R^a$S(O)$R^d$, wherein $R^a$ and $R^d$ are each as defined herein. In certain embodiments, $R^{7b}$ is —N$R^a$S(O)$_2R^d$, wherein $R^a$ and $R^d$ are each as defined herein. In certain embodiments, $R^{7b}$ is —N$R^a$S(O)N$R^bR^c$, wherein $R^a$, $R^b$, and $R^c$ are each as defined herein. In certain embodiments, $R^{7b}$ is —N$R^a$S(O)$_2$N$R^bR^c$, wherein $R^a$, $R^b$, and $R^c$ are each as defined herein. In certain embodiments, $R^{7b}$ is —S$R^a$, wherein $R^a$ is as defined herein. In certain embodiments, $R^{7b}$ is —S(O)$R^a$, wherein $R^a$ is as defined herein. In certain embodiments, $R^{7b}$ is —S(O)$_2R^a$, wherein $R^a$ is as defined herein. In certain embodiments, $R^{7b}$ is —S(O)N$R^bR^c$, wherein $R^b$ and $R^c$ are each as defined herein. In certain embodiments, $R^{7b}$ is —S(O)$_2$N$R^bR^c$; wherein $R^b$ and $R^c$ are each as defined herein.

In certain embodiments, $R^{7b}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$. In certain embodiments, $R^{7b}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, $R^{7c}$ is hydrogen. In certain embodiments, $R^{7c}$ is cyano. In certain embodiments, $R^{7c}$ is halo. In certain embodiments, $R^{7c}$ is fluoro, chloro, bromo, or iodo. In certain embodiments, $R^{7c}$ is nitro. In certain embodiments, $R^{7c}$ is $C_{1-6}$ alkyl, optionally substituted with one, two, three, or four substituents $Q^a$ as described herein. In certain embodiments, $R^{7c}$ is $C_{2-6}$ alkenyl, optionally substituted with one, two, three, or four substituents $Q^a$ as described herein. In certain embodiments, $R^{7c}$ is $C_{2-6}$ alkynyl, optionally substituted with one, two, three, or four substituents $Q^a$ as described herein. In certain embodiments, $R^{7c}$ is $C_{3-10}$ cycloalkyl, optionally substituted with one, two, three, or four substituents $Q^a$ as described herein. In certain embodiments, $R^{7c}$ is $C_{3-7}$ cycloalkyl, optionally substituted with one, two, three, or four substituents $Q^a$ as described herein. In certain embodiments, $R^{7c}$ is $C_{6-14}$ aryl, optionally substituted with one, two, three, or four substituents $Q^a$ as described herein. In certain embodiments, $R^{7c}$ is $C_{7-15}$ aralkyl, optionally substituted with one, two, three, or four substituents $Q^a$ as described herein. In certain embodiments, $R^{7c}$ is heteroaryl, optionally substituted with one, two, three, or four substituents $Q^a$ as described herein. In certain embodiments, $R^{7c}$ is heterocyclyl, optionally substituted with one, two, three, or four substituents $Q^a$ as described herein.

In certain embodiments, $R^{7c}$ is —C(O)$R^a$, wherein $R^a$ is as defined herein. In certain embodiments, $R^{7c}$ is —C(O)OR$^a$, wherein $R^a$ is as defined herein. In certain embodiments, $R^{7c}$ is —C(O)NR$^b$R$^c$, wherein $R^b$ and $R^c$ are each as defined herein. In certain embodiments, $R^{7c}$ is —C(NR$^a$)NR$^b$R$^c$, wherein $R^a$, $R^b$, and $R^c$ are each as defined herein. In certain embodiments, $R^{7c}$ is —OR$^a$, wherein $R^a$ is as defined herein. In certain embodiments, $R^a$ is —O—$C_{1-6}$ alkyl, wherein the alkyl is optionally substituted with one, two, three, or four substituents $Q^a$ as described herein. In certain embodiments, $R^a$ is methoxy, ethoxy, propoxy, isopropoxy, or 3-dimethylaminopropoxy. In certain embodiments, $R^{7c}$ is —OC(O)R$^a$, wherein $R^a$ is as defined herein. In certain embodiments, $R^{7c}$ is —OC(O)OR$^a$, wherein $R^a$ is as defined herein. In certain embodiments, $R^{7c}$ is —OC(O)NR$^b$R$^c$, wherein $R^b$ and $R^c$ are each as defined herein. In certain embodiments, $R^{7c}$ is —OC(=NR$^a$)NR$^b$R$^c$, wherein $R^a$, $R^b$, and $R^c$ are each as defined herein. In certain embodiments, $R^{7c}$ is —OS(O)R$^a$, wherein $R^a$ is as defined herein. In certain embodiments, $R^{7c}$ is —OS(O)$_2$R$^a$, wherein $R^a$ is as defined herein. In certain embodiments, $R^{7c}$ is —OS(O)NR$^b$R$^c$, wherein $R^b$ and $R^c$ are each as defined herein. In certain embodiments, $R^{7c}$ is —OS(O)$_2$NR$^b$R$^c$, wherein $R^b$ and $R^c$ are each as defined herein. In certain embodiments, $R^{7c}$ is —NR$^b$R$^c$, wherein $R^b$ and $R^c$ are each as defined herein. In certain embodiments, $R^{7c}$ is amino (—NH$_2$). In certain embodiments, $R^{7c}$ is —NR$^a$C(O)R$^d$, wherein $R^a$ and $R^d$ are each as defined herein. In certain embodiments, $R^{7c}$ is —NR$^a$C(O)OR$^d$, wherein $R^a$ and $R^d$ are each as defined herein. In certain embodiments, $R^{7c}$ is —NR$^a$C(O)NR$^b$R$^c$, wherein $R^a$, $R^b$, and $R^c$ are each as defined herein. In certain embodiments, $R^{7c}$ is —NR$^a$C(=NR$^d$)NR$^b$R$^c$, wherein $R^a$, $R^b$, $R^c$, and $R^d$ are each as defined herein. In certain embodiments, $R^{7c}$ is —NR$^a$S(O)R$^d$, wherein $R^a$ and $R^d$ are each as defined herein. In certain embodiments, $R^{7c}$ is —NR$^a$S(O)$_2$R$^d$, wherein $R^a$ and $R^d$ are each as defined herein. In certain embodiments, $R^{7c}$ is —NR$^a$S(O)NR$^b$R$^c$, wherein $R^a$, $R^b$, and $R^c$ are each as defined herein. In certain embodiments, $R^{7c}$ is —NR$^a$S(O)$_2$NR$^b$R$^c$, wherein $R^a$, $R^b$, and $R^c$ are each as defined herein. In certain embodiments, $R^{7c}$ is —SR$^a$, wherein $R^a$ is as defined herein. In certain embodiments, $R^{7c}$ is —S(O)R$^a$, wherein $R^a$ is as defined herein. In certain embodiments, $R^{7c}$ is —S(O)$_2$R$^a$, wherein $R^a$ is as defined herein. In certain embodiments, $R^{7c}$ is —S(O)NR$^b$R$^c$, wherein $R^b$ and $R^c$ are each as defined herein. In certain embodiments, $R^{7c}$ is —S(O)$_2$NR$^b$R$^c$; wherein $R^b$ and $R^c$ are each as defined herein.

In certain embodiments, $R^{7c}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$. In certain embodiments, $R^{7c}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, $R^{7d}$ is hydrogen. In certain embodiments, $R^{7d}$ is cyano. In certain embodiments, $R^{7d}$ is halo. In certain embodiments, $R^{7d}$ is fluoro, chloro, bromo, or iodo. In certain embodiments, $R^{7d}$ is nitro. In certain embodiments, $R^{7d}$ is $C_{1-6}$ alkyl, optionally substituted with one, two, three, or four substituents $Q^a$ as described herein. In certain embodiments, $R^{7d}$ is $C_{2-6}$ alkenyl, optionally substituted with one, two, three, or four substituents $Q^a$ as described herein. In certain embodiments, $R^{7d}$ is $C_{2-6}$ alkynyl, optionally substituted with one, two, three, or four substituents $Q^a$ as described herein. In certain embodiments, $R^{7d}$ is $C_{3-10}$ cycloalkyl, optionally substituted with one, two, three, or four substituents $Q^a$ as described herein. In certain embodiments, $R^{7d}$ is $C_{3-7}$ cycloalkyl, optionally substituted with one, two, three, or four substituents $Q^a$ as described herein. In certain embodiments, $R^{7d}$ is $C_{6-14}$ aryl, optionally substituted with one, two, three, or four substituents $Q^a$ as described herein. In certain embodiments, $R^{7d}$ is $C_{7-15}$ aralkyl, optionally substituted with one, two, three, or four substituents $Q^a$ as described herein. In certain embodiments, $R^{7d}$ is heteroaryl, optionally substituted with one, two, three, or four substituents $Q^a$ as described herein. In certain embodiments, $R^{7d}$ is heterocyclyl, optionally substituted with one, two, three, or four substituents $Q^a$ as described herein.

In certain embodiments, $R^{7d}$ is —C(O)R$^a$, wherein $R^a$ is as defined herein. In certain embodiments, $R^{7d}$ is —C(O)

OR$^a$, wherein R$^a$ is as defined herein. In certain embodiments, R$^{7d}$ is —C(O)NR$^b$R$^c$, wherein R$^b$ and R$^c$ are each as defined herein. In certain embodiments, R$^{7d}$ is —C(NR$^a$)NR$^b$R$^c$, wherein R$^a$, R$^b$, and R$^c$ are each as defined herein. In certain embodiments, R$^{7d}$ is —OR$^a$, wherein R$^a$ is as defined herein. In certain embodiments, R$^a$ is —O—C$_{1-6}$ alkyl, wherein the alkyl is optionally substituted with one, two, three, or four substituents Q$^a$ as described herein. In certain embodiments, R$^a$ is methoxy, ethoxy, propoxy, isopropoxy, or 3-dimethylaminopropoxy. In certain embodiments, R$^{7d}$ is —OC(O)R$^a$, wherein R$^a$ is as defined herein. In certain embodiments, R$^{7d}$ is —OC(O)OR$^a$, wherein R$^a$ is as defined herein. In certain embodiments, R$^{7d}$ is —OC(O)NR$^b$R$^c$, wherein R$^b$ and R$^c$ are each as defined herein. In certain embodiments, R$^{7d}$ is —OC(=NR$^a$)NR$^b$R$^c$, wherein R$^a$, R$^b$, and R$^c$ are each as defined herein. In certain embodiments, R$^{7d}$ is —OS(O)R$^a$, wherein R$^a$ is as defined herein. In certain embodiments, R$^{7d}$ is —OS(O)$_2$R$^a$, wherein R$^a$ is as defined herein. In certain embodiments, R$^{7d}$ is —OS(O)NR$^b$R$^c$, wherein R$^b$ and R$^c$ are each as defined herein. In certain embodiments, R$^{7d}$ is —OS(O)$_2$NR$^b$R$^c$, wherein R$^b$ and R$^c$ are each as defined herein. In certain embodiments, R$^{7d}$ is —NR$^b$R$^c$, wherein R$^b$ and R$^c$ are each as defined herein. In certain embodiments, R$^{7d}$ is amino (—NH$_2$). In certain embodiments, R$^{7d}$ is —NR$^a$C(O)R$^d$, wherein R$^a$ and R$^d$ are each as defined herein. In certain embodiments, R$^{7d}$ is —NR$^a$C(O)OR$^d$, wherein R$^a$ and R$^d$ are each as defined herein. In certain embodiments, R$^{7d}$ is —NR$^a$C(O)NR$^b$R$^c$, wherein R$^a$, R$^b$, and R$^c$ are each as defined herein. In certain embodiments, R$^{7d}$ is —NR$^a$C(=NR$^d$)NR$^b$R$^c$, wherein R$^a$, R$^b$, R$^c$, and R$^d$ are each as defined herein. In certain embodiments, R$^{7d}$ is —NR$^a$S(O)R$^d$, wherein R$^a$ and R$^d$ are each as defined herein. In certain embodiments, R$^{7d}$ is —NR$^a$S(O)$_2$R$^d$, wherein R$^a$ and R$^d$ are each as defined herein. In certain embodiments, R$^{7d}$ is —NR$^a$S(O)NR$^b$R$^c$, wherein R$^a$, R$^b$, and R$^c$ are each as defined herein. In certain embodiments, R$^{7d}$ is —NR$^a$S(O)$_2$NR$^b$R$^c$, wherein R$^a$, R$^b$, and R$^c$ are each as defined herein. In certain embodiments, R$^{7d}$ is —SR$^a$, wherein R$^a$ is as defined herein. In certain embodiments, R$^{7d}$ is —S(O)R$^a$, wherein R$^a$ is as defined herein. In certain embodiments, R$^{7d}$ is —S(O)$_2$R$^a$, wherein R$^a$ is as defined herein. In certain embodiments, R$^{7d}$ is —S(O)NR$^b$R$^c$, wherein R$^b$ and are each as defined herein. In certain embodiments, R$^{7d}$ is —S(O)$_2$NR$^b$R$^c$; wherein R$^b$ and are each as defined herein.

In certain embodiments, R$^{7d}$ is phenyl, imidazolyl, pyrozolyl, pyridinyl, pyrimidinyl, pyrrolidinyl, piperidinyl, or piperazinyl, each optionally substituted with one, two, three, or four substituents Q$^a$. In certain embodiments, R$^{7d}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, R$^{7e}$ is hydrogen. In certain embodiments, R$^{7e}$ is cyano. In certain embodiments, R$^{7e}$ is halo. In certain embodiments, R$^{7e}$ is fluoro, chloro, bromo, or iodo. In certain embodiments, R$^{7e}$ is nitro. In certain embodiments, R$^{7e}$ is C$_{1-6}$ alkyl, optionally substituted with one, two, three, or four substituents Q$^a$ as described herein. In certain embodiments, R$^{7e}$ is C$_{2-6}$ alkenyl, optionally substituted with one, two, three, or four substituents Q$^a$ as described herein. In certain embodiments, R$^{7e}$ is C$_{2-6}$ alkynyl, optionally substituted with one, two, three, or four substituents Q$^a$ as described herein. In certain embodiments, R$^{7e}$ is C$_{3-10}$ cycloalkyl, optionally substituted with one, two, three, or four substituents Q$^a$ as described herein. In certain embodiments, R$^{7e}$ is C$_{3-7}$ cycloalkyl, optionally substituted with one, two, three, or four substituents Q$^a$ as described herein. In certain embodiments, R$^{7e}$ is C$_{6-14}$ aryl, optionally substituted with one, two, three, or four substituents Q$^a$ as described herein. In certain embodiments, R$^{7e}$ is C$_{7-15}$ aralkyl, optionally substituted with one, two, three, or four substituents Q$^a$ as described herein. In certain embodiments, R$^{7e}$ is heteroaryl, optionally substituted with one, two, three, or four substituents Q$^a$ as described herein. In certain embodiments, R$^{7e}$ is heterocyclyl, optionally substituted with one, two, three, or four substituents Q$^a$ as described herein.

In certain embodiments, R$^{7e}$ is —C(O)R$^a$, wherein R$^a$ is as defined herein. In certain embodiments, R$^{7e}$ is —C(O)OR$^a$, wherein R$^a$ is as defined herein. In certain embodiments, R$^{7e}$ is —C(O)NR$^b$R$^c$, wherein R$^b$ and are each as defined herein. In certain embodiments, R$^{7e}$ is —C(NR$^a$)NR$^b$R$^c$, wherein R$^a$, R$^b$, and R$^c$ are each as defined herein. In certain embodiments, R$^{7e}$ is —OR$^a$, wherein R$^a$ is as defined herein. In certain embodiments, R$^a$ is —O—C$_{1-6}$ alkyl, wherein the alkyl is optionally substituted with one, two, three, or four substituents Q$^a$ as described herein. In certain embodiments, R$^a$ is methoxy, ethoxy, propoxy, isopropoxy, or 3-dimethylaminopropoxy. In certain embodiments, R$^{7e}$ is —OC(O)R$^a$, wherein R$^a$ is as defined herein. In certain embodiments, R$^{7e}$ is —OC(O)OR$^a$, wherein R$^a$ is as defined herein. In certain embodiments, R$^{7e}$ is —OC(O)NR$^b$R$^c$, wherein R$^b$ and R$^c$ are each as defined herein. In certain embodiments, R$^{7e}$ is —OC(=NR$^a$)NR$^b$R$^c$, wherein R$^a$, R$^b$, and R$^c$ are each as defined herein. In certain embodiments, R$^{7e}$ is —OS(O)R$^a$, wherein R$^a$ is as defined herein. In certain embodiments, R$^{7e}$ is —OS(O)$_2$R$^a$, wherein R$^a$ is as defined herein. In certain embodiments, R$^{7e}$ is —OS(O)NR$^b$R$^c$, wherein R$^b$ and are each as defined herein. In certain embodiments, R$^{7e}$ is —OS(O)$_2$NR$^b$R$^c$, wherein R$^b$ and are each as defined herein. In certain embodiments, R$^{7e}$ is —NR$^b$R$^c$, wherein R$^b$ and are each as defined herein. In certain embodiments, R$^{7e}$ is amino (—NH$_2$). In certain embodiments, R$^{7e}$ is —NR$^a$C(O)R$^d$, wherein R$^a$ and R$^d$ are each as defined herein. In certain embodiments, R$^{7e}$ is —NR$^a$C(O)OR$^d$, wherein R$^a$ and R$^d$ are each as defined herein. In certain embodiments, R$^{7e}$ is —NR$^a$C(O)NR$^b$R$^c$, wherein R$^a$, R$^b$, and are each as defined herein. In certain embodiments, R$^{7e}$ is —NR$^a$C(=NR$^d$)NR$^b$R$^c$, wherein R$^a$, R$^b$, R$^c$, and R$^d$ are each as defined herein. In certain embodiments, R$^{7e}$ is —NR$^a$S(O)R$^d$, wherein R$^a$ and R$^d$ are each as defined herein. In certain embodiments, R$^{7e}$ is —NR$^a$S(O)$_2$R$^d$, wherein R$^a$ and R$^d$ are each as defined herein. In certain embodiments, R$^{7e}$ is —NR$^a$S(O)NR$^b$R$^c$, wherein R$^a$, R$^b$, and are each as defined herein. In certain embodiments, R$^{7e}$ is —NR$^a$S(O)$_2$NR$^b$R$^c$, wherein R$^a$, R$^b$, and R$^c$ are each as defined herein. In certain embodiments, R$^{7e}$ is —SR$^a$, wherein R$^a$ is as defined herein. In certain embodiments, R$^{7e}$ is —S(O)R$^a$, wherein R$^a$ is as defined herein. In certain embodiments, R$^{7e}$ is —S(O)$_2$R$^a$, wherein R$^a$ is as defined herein. In certain embodiments, R$^{7e}$ is —S(O)NR$^b$R$^c$, wherein R$^b$ and are each as defined herein. In certain embodiments, $R^{7e}$ is —S(O)$_2$NR$^b$R$^c$; wherein $R^b$ and $R^c$ are each as defined herein.

In certain embodiments, $R^{7e}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$. In certain embodiments, $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-fluorophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, $R^{7a}$ and $R^{7b}$ together with the carbon atoms to which they are attached form $C_{3-10}$ cycloalkenyl, $C_{6-14}$ aryl, heteroaryl, or heterocyclyl, each optionally substituted with one, two, three, or four substituents $Q^a$. In certain embodiments, $R^{7a}$ and $R^{7b}$ together with the carbon atoms to which they are attached form $C_{3-10}$ cycloalkenyl, optionally substituted with one, two, three, or four substituents $Q^a$. In certain embodiments, $R^{7a}$ and $R^{7b}$ together with the carbon atoms to which they are attached form cyclohexenyl, optionally substituted with one, two, three, or four substituents $Q^a$. In certain embodiments, $R^{7a}$ and $R^{7b}$ together with the carbon atoms to which they are attached form $C_{6-14}$ aryl, optionally substituted with one, two, three, or four substituents $Q^a$. In certain embodiments, $R^{7a}$ and $R^{7b}$ together with the carbon atoms to which they are attached form phenyl, optionally substituted with one, two, three, or four substituents $Q^a$. In certain embodiments, $R^{7a}$ and $R^{7b}$ together with the carbon atoms to which they are attached form heteroaryl, optionally substituted with one, two, three, or four substituents $Q^a$. In certain embodiments, $R^{7a}$ and $R^{7b}$ together with the carbon atoms to which they are attached form monocyclic heteroaryl, optionally substituted with one, two, three, or four substituents $Q^a$. In certain embodiments, $R^{7a}$ and $R^{7b}$ together with the carbon atoms to which they are attached form 5- or 6-membered heteroaryl, optionally substituted with one, two, three, or four substituents $Q^a$. In certain embodiments, $R^{7a}$ and $R^{7b}$ together with the carbon atoms to which they are attached form bicyclic heteroaryl, optionally substituted with one, two, three, or four substituents $Q^a$. In certain embodiments, $R^{7a}$ and $R^{7b}$ together with the carbon atoms to which they are attached form heterocyclyl, optionally substituted with one, two, three, or four substituents $Q^a$. In certain embodiments, $R^{7a}$ and $R^{7b}$ together with the carbon atoms to which they are attached form monocyclic heterocyclyl, optionally substituted with one, two, three, or four substituents $Q^a$. In certain embodiments, $R^{7a}$ and $R^{7b}$ together with the carbon atoms to which they are attached form 5- or 6-membered heterocyclyl, optionally substituted with one, two, three, or four substituents $Q^a$. In certain embodiments, $R^{7a}$ and $R^{7b}$ together with the carbon atoms to which they are attached form bicyclic heterocyclyl, optionally substituted with one, two, three, or four substituents $Q^a$.

In certain embodiments, $R^{7b}$ and $R^{7c}$ together with the carbon atoms to which they are attached form $C_{3-10}$ cycloalkenyl, $C_{6-14}$ aryl, heteroaryl, or heterocyclyl, each optionally substituted with one, two, three, or four substituents $Q^a$. In certain embodiments, $R^{7b}$ and $R^{7c}$ together with the carbon atoms to which they are attached form $C_{3-10}$ cycloalkenyl, optionally substituted with one, two, three, or four substituents $Q^a$. In certain embodiments, $R^{7b}$ and $R^{7c}$ together with the carbon atoms to which they are attached form cyclohexenyl, optionally substituted with one, two, three, or four substituents $Q^a$. In certain embodiments, $R^{7b}$ and $R^{7c}$ together with the carbon atoms to which they are attached form $C_{6-14}$ aryl, optionally substituted with one, two, three, or four substituents $Q^a$. In certain embodiments, $R^{7b}$ and $R^{7c}$ together with the carbon atoms to which they are attached form phenyl, optionally substituted with one, two, three, or four substituents $Q^a$. In certain embodiments, $R^{7b}$ and $R^{7c}$ together with the carbon atoms to which they are attached form heteroaryl, optionally substituted with one, two, three, or four substituents $Q^a$. In certain embodiments, $R^{7b}$ and $R^{7c}$ together with the carbon atoms to which they are attached form monocyclic heteroaryl, optionally substituted with one, two, three, or four substituents $Q^a$. In certain embodiments, $R^{7b}$ and $R^{7c}$ together with the carbon atoms to which they are attached form 5- or 6-membered heteroaryl, optionally substituted with one, two, three, or four substituents $Q^a$. In certain embodiments, $R^{7b}$ and $R^{7c}$ together with the carbon atoms to which they are attached form bicyclic heteroaryl, optionally substituted with one, two, three, or four substituents $Q^a$. In certain embodiments, $R^{7b}$ and $R^{7c}$ together with the carbon atoms to which they are attached form heterocyclyl, optionally substituted with one, two, three, or four substituents $Q^a$. In certain embodiments, $R^{7b}$ and $R^{7c}$ together with the carbon atoms to which they are attached form monocyclic heterocyclyl, optionally substituted with one, two, three, or four substituents $Q^a$. In certain embodiments, $R^{7b}$ and $R^{7c}$ together with the carbon atoms to which they are attached form 5- or 6-membered heterocyclyl, optionally substituted with one, two, three, or four substituents $Q^a$. In certain embodiments, $R^{7b}$ and $R^{7c}$ together with the carbon atoms to which they are attached form bicyclic heterocyclyl, optionally substituted with one, two, three, or four substituents $Q^a$.

In certain embodiments, $R^{7c}$ and $R^{7d}$ together with the carbon atoms to which they are attached form $C_{3-10}$ cycloalkenyl, $C_{6-14}$ aryl, heteroaryl, or heterocyclyl, each optionally substituted with one, two, three, or four substituents $Q^a$. In certain embodiments, $R^{7c}$ and $R^{7d}$ together with the carbon atoms to which they are attached form $C_{3-10}$ cycloalkenyl, optionally substituted with one, two, three, or four substituents $Q^a$. In certain embodiments, $R^{7c}$ and $R^{7d}$ together with the carbon atoms to which they are attached form cyclohexenyl, optionally substituted with one, two, three, or four substituents $Q^a$. In certain embodiments, $R^{7c}$ and $R^{7d}$ together with the carbon atoms to which they are attached form $C_{6-14}$ aryl, optionally substituted with one, two, three, or four substituents $Q^a$. In certain embodiments, $R^{7c}$ and $R^{7d}$ together with the carbon atoms to which they are attached form phenyl, optionally substituted with one, two, three, or four substituents $Q^a$. In certain embodiments, $R^{7c}$ and $R^{7d}$ together with the carbon atoms to which they are attached form heteroaryl, optionally substituted with one, two, three, or four substituents $Q^a$. In certain embodiments, $R^{7c}$ and $R^{7d}$ together with the carbon atoms to which they are attached form monocyclic heteroaryl, optionally substituted with one, two, three, or four substituents $Q^a$. In certain embodiments, $R^{7c}$ and $R^{7d}$ together with the carbon atoms to which they are attached form 5- or 6-membered heteroaryl, optionally substituted with one, two, three, or four substituents $Q^a$. In certain embodiments, $R^{7c}$ and $R^{7d}$ together with the carbon atoms to which they are attached form bicyclic heteroaryl, optionally substituted with one, two, three, or four substituents $Q^a$. In certain embodiments, $R^{7c}$ and $R^{7d}$ together with the carbon atoms to which they are attached form heterocyclyl, optionally substituted with one, two, three, or four substituents $Q^a$. In certain embodiments, $R^{7c}$ and $R^{7d}$ together with the carbon atoms to which they are attached form monocyclic heterocyclyl, optionally substituted with one, two, three, or four substituents $Q^a$. In certain embodiments, $R^{7c}$ and $R^{7d}$ together with the carbon atoms to which they are attached form 5- or 6-membered heterocyclyl, optionally substituted with one, two, three, or four substituents $Q^a$. In certain embodiments, $R^{7c}$ and $R^{7d}$ together with the carbon atoms to which they are attached form bicyclic heterocyclyl, optionally substituted with one, two, three, or four substituents $Q^a$.

In certain embodiments, $R^{7d}$ and $R^{7e}$ together with the carbon atoms to which they are attached form $C_{3-10}$ cycloalkenyl, $C_{6-14}$ aryl, heteroaryl, or heterocyclyl, each optionally substituted with one, two, three, or four substituents $Q^a$. In certain embodiments, $R^{7d}$ and $R^{7e}$ together with the carbon atoms to which they are attached form $C_{3-10}$ cycloalkenyl, optionally substituted with one, two, three, or four substituents $Q^a$. In certain embodiments, $R^{7d}$ and $R^{7e}$ together with the carbon atoms to which they are attached form cyclohexenyl, optionally substituted with one, two, three, or four substituents $Q^a$. In certain embodiments, $R^{7d}$ and $R^{7e}$ together with the carbon atoms to which they are attached form $C_{6-14}$ aryl, optionally substituted with one, two, three, or four substituents $Q^a$. In certain embodiments, $R^{7d}$ and $R^{7e}$ together with the carbon atoms to which they are attached form phenyl, optionally substituted with one, two, three, or four substituents $Q^a$. In certain embodiments, $R^{7d}$ and $R^{7e}$ together with the carbon atoms to which they are attached form heteroaryl, optionally substituted with one, two, three, or four substituents $Q^a$. In certain embodiments, $R^{7d}$ and $R^{7e}$ together with the carbon atoms to which they are attached form monocyclic heteroaryl, optionally substituted with one, two, three, or four substituents $Q^a$. In certain embodiments, $R^{7d}$ and $R^{7e}$ together with the carbon atoms to which they are attached form a 5- or 6-membered heteroaryl, optionally substituted with one, two, three, or four substituents $Q^a$. In certain embodiments, $R^{7d}$ and $R^{7e}$ together with the carbon atoms to which they are attached form bicyclic heteroaryl, optionally substituted with one, two, three, or four substituents $Q^a$. In certain embodiments, $R^{7d}$ and $R^{7e}$ together with the carbon atoms to which they are attached form heterocyclyl, optionally substituted with one, two, three, or four substituents $Q^a$. In certain embodiments, $R^{7d}$ and $R^{7e}$ together with the carbon atoms to which they are attached form monocyclic heterocyclyl, optionally substituted with one, two, three, or four substituents $Q^a$. In certain embodiments, $R^{7d}$ and $R^{7e}$ together with the carbon atoms to which they are attached form 5- or 6-membered heterocyclyl, optionally substituted with one, two, three, or four substituents $Q^a$. In certain embodiments, $R^{7d}$ and $R^{7e}$ together with the carbon atoms to which they are attached form bicyclic heterocyclyl, optionally substituted with one, two, three, or four substituents $Q^a$.

In certain embodiments, m is 0. In certain embodiments, m is 1.

In certain embodiments, n is 0. In certain embodiments, n is 1. In certain embodiments, n is 2. In certain embodiments, n is 3. In certain embodiments, n is 4. In certain embodiments, n is 0, 1, or 2. In certain embodiments, n is 0, 1, 2, or 3. In certain embodiments, n is 1, 2, or 3. In certain embodiments, n is 1 or 2.

In certain embodiments, m is 0, and n is 0, 1, 2, or 3. In certain embodiments, m is 0, and n is 0, 1, or 2. In certain embodiments, m is 0, and n is 0 or 1. In certain embodiments, m is 0, and n is 0. In certain embodiments, m is 0, and n is 1. In certain embodiments, m is 1, and n is 0, 1, 2, or 3. In certain embodiments, m is 1, and n is 0, 1, or 2. In certain embodiments, m is 1, and n is 0 or 1. In certain embodiments, m is 1, and n is 0. In certain embodiments, m is 1, and n is 1.

In specific embodiments, m is 0, n is 1, and $R^{5a}$ and $R^{5b}$ are each methyl.

In certain embodiments, X is N In certain embodiments, X is $CR^x$, wherein $R^x$ is as defined herein. In certain embodiments, X is CH.

In certain embodiments, Y is N In certain embodiments, Y is $CR^x$, wherein $R^x$ is as defined herein. In certain embodiments, Y is CH.

In certain embodiments, Z is N In certain embodiments, Z is $CR^x$, wherein $R^x$ is as defined herein. In certain embodiments, Z is CH.

In certain embodiments, X, Y, and Z are N. In certain embodiments, X and Y are N, and Z is CH. In certain embodiments, X and Z are N, and Y is CH. In certain embodiments, Y and Z are N, and X is CH.

In certain embodiments, the compound provided herein is not 4-(2-(difluoromethyl)-1H-benzo[d]imidazol-1-yl)-6-morpholino-N-(2-phenyl-2-(pyrrolidin-1-yl)ethyl)-1,3,5-triazin-2-amine. In certain embodiments, the compound provided herein is not 6-(2-(difluoromethyl)-1H-benzo[d]imidazol-1-yl)-N-(1-(4-((R)-3-(methoxymethyl)morpholino)phenyl)ethyl)-2-morpholinopyrimidin-4-amine.

In certain embodiments, when X, Y, and Z are N, and $R^{5a}$ is hydrogen, $R^{5b}$ is not heterocyclyl. In certain embodiments, when X, Y, and Z are N, and $R^{5a}$ is hydrogen, $R^{5b}$ is not 5-membered heterocyclyl. In certain embodiments, when X, Y, and Z are N, and $R^{5a}$ is hydrogen, $R^{5b}$ is not pyrrolidinyl. In certain embodiments, when X, Y, and Z are N, and $R^{5a}$ is hydrogen, $R^{5b}$ is not pyrrolidin-1-yl.

In certain embodiments, when X and Z are N, Y is CH, and $R^{5a}$ is hydrogen, $R^{5b}$ is morpholino-substituted phenyl. In certain embodiments, when X and Z are N, Y is CH, and $R^{5a}$ is hydrogen, $R^{5b}$ is not 4-((R)-3-(methoxymethyl)morpholino)phenyl.

In one embodiment, provided herein is a compound selected from:

Compound I

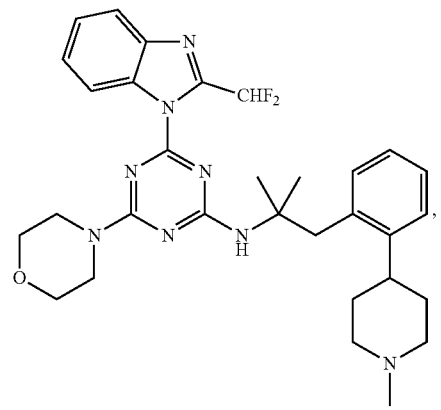

Compound II
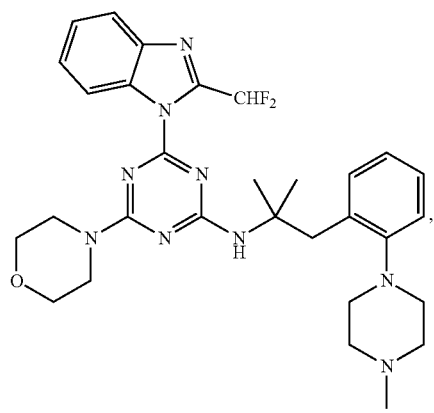
Compound III
Compound IV
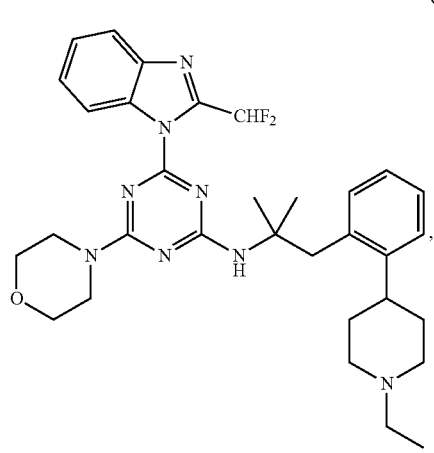
Compound V
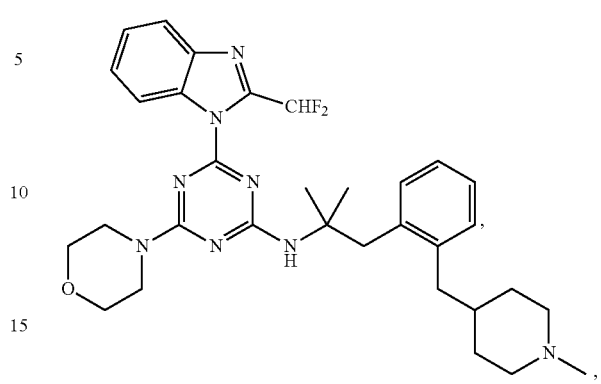
Compound VI
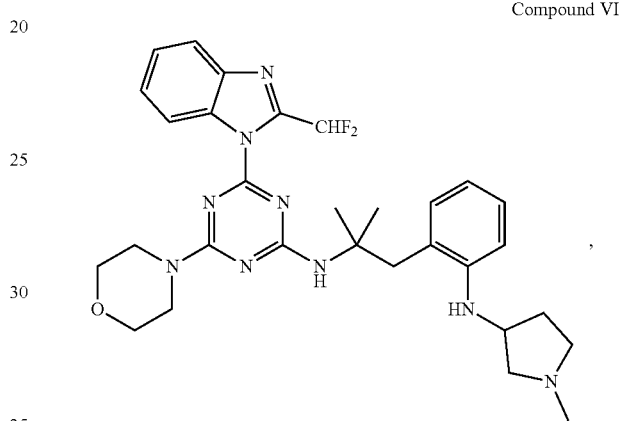
Compound VII
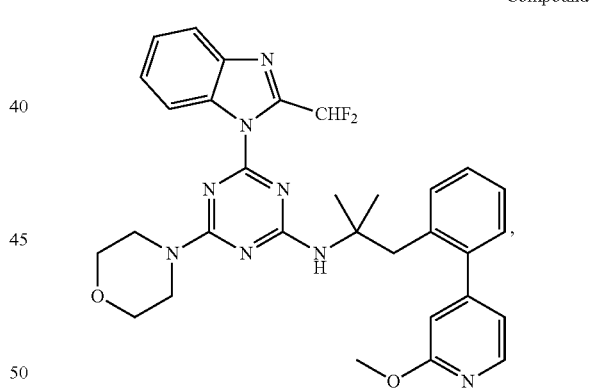
Compound VIII
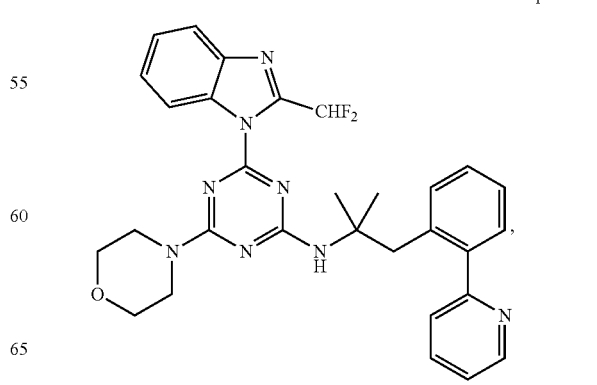

Compound IX
Compound X
Compound XI
Compound XII
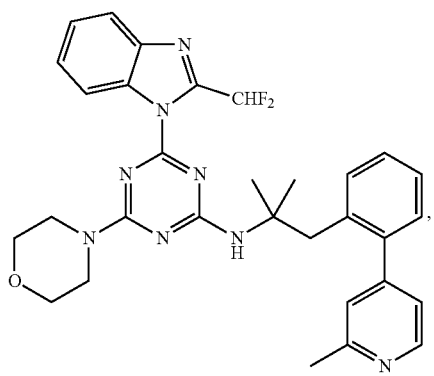
Compound XIII
Compound XIV
Compound XV
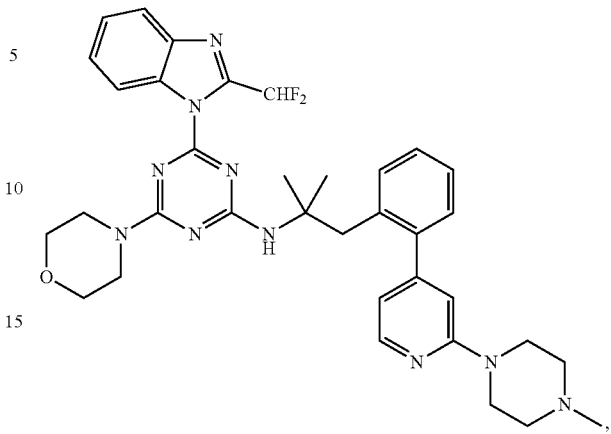
, and -continued Compound XVI

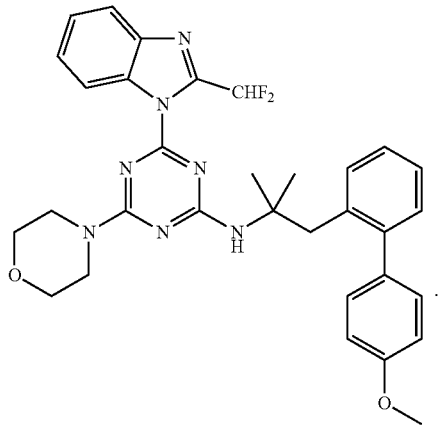

In one embodiment, the PI3K inhibitor is Compound I, or an isotopic variant, pharmaceutically acceptable salt, solvate, hydrate, or prodrug thereof. In one embodiment, the PI3K inhibitor is Compound II, or an isotopic variant, pharmaceutically acceptable salt, solvate, hydrate, or prodrug thereof. In one embodiment, the PI3K inhibitor is Compound III, or an isotopic variant, pharmaceutically acceptable salt, solvate, hydrate, or prodrug thereof. In one embodiment, the PI3K inhibitor is Compound IV, or an isotopic variant, pharmaceutically acceptable salt, solvate, hydrate, or prodrug thereof. In one embodiment, the PI3K inhibitor is Compound V, or an isotopic variant, pharmaceutically acceptable salt, solvate, hydrate, or prodrug thereof. In one embodiment, the PI3K inhibitor is Compound VI, or an isotopic variant, pharmaceutically acceptable salt, solvate, hydrate, or prodrug thereof. In one embodiment, the PI3K inhibitor is Compound VII, or an isotopic variant, pharmaceutically acceptable salt, solvate, hydrate, or prodrug thereof. In one embodiment, the PI3K inhibitor is Compound VIII, or an isotopic variant, pharmaceutically acceptable salt, solvate, hydrate, or prodrug thereof. In one embodiment, the PI3K inhibitor is Compound IX, or an isotopic variant, pharmaceutically acceptable salt, solvate, hydrate, or prodrug thereof. In one embodiment, the PI3K inhibitor is Compound X, or an isotopic variant, pharmaceutically acceptable salt, solvate, hydrate, or prodrug thereof. In one embodiment, the PI3K inhibitor is Compound XI, or an isotopic variant, pharmaceutically acceptable salt, solvate, hydrate, or prodrug thereof. In one embodiment, the PI3K inhibitor is Compound XII, or an isotopic variant, pharmaceutically acceptable salt, solvate, hydrate, or prodrug thereof. In one embodiment, the PI3K inhibitor is Compound XIII, or an isotopic variant, pharmaceutically acceptable salt, solvate, hydrate, or prodrug thereof. In one embodiment, the PI3K inhibitor is Compound XIV, or an isotopic variant, pharmaceutically acceptable salt, solvate, hydrate, or prodrug thereof. In one embodiment, the PI3K inhibitor is Compound XV, or an isotopic variant, pharmaceutically acceptable salt, solvate, hydrate, or prodrug thereof. In one embodiment, the PI3K inhibitor is Compound XVI, or an isotopic variant, pharmaceutically acceptable salt, solvate, hydrate, or prodrug thereof.

PD-1 and PD-L1 Inhibitors

Described herein are PI3K inhibitors in combination with PD-1 or PD-L1 inhibitors.

The PD-1 (programmed cell death 1) receptor (also known as CD279) is expressed on the surface of activated T cells. Its ligand, PD-L1, is commonly expressed on the surface of dendritic cells or macrophages. In some instances, PD1 and PD-L1 interaction halts or limits the development of the T cell response. When PD-L1 binds to PD-1, an inhibitory signal is transmitted into the T cell, which reduces cytokine production and suppresses T-cell proliferation. In some instances, cancer or tumor cells exploit this signaling pathway as a mechanism to evade detection and inhibit the immune response. In some instances, PD-L1 is overexpressed on cancer or tumor cells or on non-transformed cells in the tumor microenvironment. In some instances, PD-L1 expressed on the tumor cells binds to PD-1 receptors on the activated T cells, which leads to the inhibition of the cytotoxic T cells. These deactivated T cells remain inhibited in the tumor microenvironment. The PD1/PD-L1 pathway represents an adaptive immune resistance mechanism that is exerted by cancer or tumor cells in response to endogenous anti-tumor activity.

PD-1 inhibitors (or anti-PD-1 agents) and PD-L1 inhibitors (or anti-PD-L1 agents) block the interaction between PD-1 and PD-L1 and boost the immune response against cancer cells. In some instances, the blockade of receptor engagement results in the amplification of antigen-specific T cell responses against cancer cells. In some instances, antibodies that block the PD-1/PD-L1 interaction target lymphocyte receptors or their ligands in order to enhance endogenous antitumor activity. In some instances, PD-1 inhibitors and PD-L1 inhibitors overcome distinct immune suppressive pathways within the tumor microenvironment. In some instances, PD-1 inhibitors and/or PD-L1 inhibitors are useful for treating cancer.

Any suitable PD-1 inhibitor or PD-L1 inhibitor may be used in combination with a PI3K inhibitor described herein. In some embodiments, the PD-1 inhibitor is an antagonist of PD-1. In some embodiments, the PD-L1 inhibitor is an antagonist of PD-L1. In some embodiments, the PD-1 inhibitor or PD-L1 inhibitor is an antibody, variant, or biosimilar thereof. In some embodiments, the PD-1 inhibitor or PD-L1 inhibitor is a monoclonal antibody. In some embodiments, the method of treating cancer with a PI3K inhibitor described herein in combination with a PD-1 or PD-L1 inhibitor results in a transient reduction in the level of systemic immunosuppression.

Some embodiments provided herein describe a pharmaceutical compositions or methods for use the pharmaceutical compositions comprising a PI3K inhibitor described herein in combination with a PD-1 inhibitor. PD-1 inhibitors for use in pharmaceutical compositions and methods provided herein include, but are not limited to, nivolumab (Opdivo®), pembrolizumab (Keytruda®), MEDI0680 (AMP-514), AMP-224, AMP-514 (Amplimmune), BGB-A317, PDR001, REGN2810, JS001, AGEN2034, and variants and biosimilars thereof. In some embodiments, the PD-1 inhibitor is to nivolumab (Opdivo®), pembrolizumab (Keytruda®), MEDI0680 (AMP-514), AMP-224, AMP-514 (Amplimmune), or variants or biosimilars thereof. In some embodiments, the PD-1 inhibitor is pidilzumab (CT-011), or a variant or biosimilar thereof. In some embodiments, the PD-1 inhibitor is nivolumab (Opdivo®), or pembrolizumab (Keytruda®), or a variant or biosimilar thereof. In some embodiments, the PD-1 inhibitor is nivolumab (Opdivo®), a nivolumab variant, or a nivolumab biosimilar. In some embodiments, the PD-1 inhibitor is pembrolizumab (Keytruda®), a pembrolizumab variant, or a pembrolizumab biosimilar. In some embodiments, the PD-1 inhibitor is BGB-A317, a BGB-A317 variant, or a BGB-A317 biosimilar. In some embodiments, the PD-1 inhibitor is PDR001, a PDR001 variant, or a PDR001 biosimilar. In some embodiments, the PD-1 inhibitor is REGN2810, a REGN2810 variant, or a REGN2810 biosimilar.

Some embodiments provided herein describe pharmaceutical compositions or methods for using the pharmaceutical compositions comprising a PI3K inhibitor described herein in combination with a PD-L1 inhibitor. PD-L1 inhibitors for use in pharmaceutical compositions and methods provided herein include but are not limited to Atezolizumab (Tecentriq® or MPDL3280A), avelumab (Bavencio®), Durvalumab (MEDI4736), MPDL3280A (RG7446), BMS-936559 (MDX-1105), MSB0010718C, YW243.55.570, and variants and biosimilars thereof. In some embodiments, the PD-L1 inhibitor is Atezolizumab (Tecentriq® or MPDL3280A), avelumab (Bavencio®), or Durvaiumab (MEDI4736), or variants or biosimilars thereof. In some embodiments, the PD-L1 inhibitor is Atezolizumab (Tecentriq® or MPDL3280A) or avelumab (Bavencio®), or a variant or biosimilar thereof. In some embodiments, the PD-L1 inhibitor is atezolizumab (Tecentriq® or MPDL3280A), an atezolizumab variant, or an atezolizumab biosimilar. In some embodiments, the PD-L1 inhibitor is avelumab (Bavencio®), avelumab variant, or an avelumab biosimilar. In some embodiments, the PD-L1 inhibitor is BMS-936559 (MDX-1105), BMS-936559 variant, or a BMS-936559 biosimilar. In some embodiments, the PD-L1 inhibitor is durvaiumab (MEDI4736), a durvaiumab variant, or a durvaluniab biosimilar.

In some embodiments, the compounds of Formula (I), or isotopic variants, pharmaceutically acceptable salts, solvates, hydrates, or prodrugs thereof, demonstrate higher avidity and biologic activity for a PI3K (e.g., PI3Kδ) compared to other PI3K inhibitors, including but not limited to idelalisib. In some embodiments, the compounds of Formula (I), or isotopic variants, pharmaceutically acceptable salts, solvates, hydrates, or prodrugs thereof, demonstrate improved or superior drug distribution to blood cells compared to other PI3K inhibitors, including but not limited to idelalisib.

In some embodiments, the combination therapy of a PD-1 or PD-L1 inhibitor and a compound of Formula (I), or an isotopic variant, pharmaceutically acceptable salt, solvate, hydrate, or prodrug thereof, shows low toxicity to normal cells. In various embodiments, the combination of a compound of Formula (I), or an isotopic variant, pharmaceutically acceptable salt, solvate, hydrate, or prodrug thereof, and a PD-1 or PD-L1 inhibitor is selectively toxic or more toxic to rapidly proliferating cells, e.g., cancerous tumors, than to normal cells.

In some embodiments, the combination therapy described herein avoids or reduces adverse or unwanted, serious, or fatal side effects associated with the use of a PI3K inhibitor (e.g., idelalisib) and/or a PD-1 or PD-L1 inhibitor. In some embodiments, the combination therapy described herein avoids, reduces, or minimizes (serious) infections, neutropenia, (severe) diarrhea, colon inflammation, colitis, lung tissue inflammation (pneumonitis), intestinal perforation, pneumonia, anemia, thrombocytopenia, nausea, fever, fatigue, cough, abdominal pain, chills, rash, vomiting, hypertriglyceridemia, hyperglycemia, elevated levels of liver enzymes (e.g., ALT and ALST), liver toxicity, swelling in extremities, or a combination thereof in patients receiving the combination therapy. In certain embodiments, the combination therapy described herein avoids, reduces, or minimizes the incidence of infection, including serious infection. In certain embodiments, the combination therapy described herein avoids, reduces, or minimizes the incidence of neutropenia. In certain embodiments, the combination therapy described herein avoids, reduces, or minimizes the incidence of diarrhea, including severe diarrhea. In certain embodiments, the combination therapy described herein avoids, reduces, or minimizes the incidence of colon inflammation. In certain embodiments, the combination therapy described herein avoids, reduces, or minimizes the incidence of colitis. In certain embodiments, the combination therapy described herein avoids, reduces, or minimizes the incidence of lung tissue inflammation (pneumonitis). In certain embodiments, the combination therapy described herein avoids, reduces, or minimizes the incidence of intestinal perforation. In certain embodiments, the combination therapy described herein avoids, reduces, or minimizes the incidence of pneumonia. In certain embodiments, the combination therapy described herein avoids, reduces, or minimizes the incidence of anemia. In certain embodiments, the combination therapy described herein avoids, reduces, or minimizes the incidence of thrombocytopenia. In certain embodiments, the combination therapy described herein avoids, reduces, or minimizes the incidence of nausea. In certain embodiments, the combination therapy described herein avoids, reduces, or minimizes the incidence of fever. In certain embodiments, the combination therapy described herein avoids, reduces, or minimizes the incidence of fatigue. In certain embodiments, the combination therapy described herein avoids, reduces, or minimizes the incidence of cough. In certain embodiments, the combination therapy described herein avoids, reduces, or minimizes the incidence of abdominal pain. In certain embodiments, the combination therapy described herein avoids, reduces, or minimizes the incidence of chills. In certain embodiments, the combination therapy described herein avoids, reduces, or minimizes the incidence of rash. In certain embodiments, the combination therapy described herein avoids, reduces, or minimizes the incidence of vomiting. In certain embodiments, the combination therapy described herein avoids, reduces, or minimizes the incidence of hypertriglyceridemia.

In certain embodiments, the combination therapy described herein avoids, reduces, or minimizes the incidence of hyperglycemia. In certain embodiments, the combination therapy described herein avoids, reduces, or minimizes the incidence of elevated levels of liver enzymes (e.g., ALT and ALST). In certain embodiments, the combination therapy described herein avoids, reduces, or minimizes the incidence of liver toxicity. In certain embodiments, the combination therapy described herein avoids, reduces, or minimizes the incidence of swelling in the extremities.

In some embodiments, the combination therapy described herein avoids or reduces adverse or unwanted side effects associated with chemotherapy, radiotherapy, or cancer therapy. In some instances, the combination therapies and/or compositions described herein provide chemo-protective and/or radio-protective properties to non-cancerous cells. In further or additional embodiments, the lower amount/doses of PI3K inhibitor reduces or minimizes any undesired side-effects associated with chemotherapy. Non-limiting examples of side-effects associated with chemotherapy, radiotherapy, or cancer therapy include fatigue, anemia, appetite changes, bleeding problems, diarrhea, constipation, hair loss, nausea, vomiting, pain, peripheral neuropathy, swelling, skin and nail changes, urinary and bladder changes, and trouble swallowing.

Methods of Use

Some embodiments provided herein describe a method for treating or preventing a proliferative disease or disorder comprising administering a PI3K inhibitor in combination with a PD-1 inhibitor or a PD-L1 inhibitor. In certain embodiments, provided herein are methods for treating or preventing a disease comprising administering an effective amount of a compound of Formula (I), or an isotopic variant thereof or a pharmaceutically acceptable salt, solvate, hydrate, or prodrug thereof and an effective amount of a PD-1 or PD-L1 inhibitor. In some embodiments, the compound of Formula (I) is Compound I or an isotopic variant, pharmaceutically acceptable salt, solvate, hydrate, or prodrug thereof. In some embodiments, the compound of Formula (I) is Compound II or an isotopic variant, pharmaceutically acceptable salt, solvate, hydrate, or prodrug thereof. In some embodiments, the compound of Formula (I) is Compound III or an isotopic variant, pharmaceutically acceptable salt, solvate, hydrate, or prodrug thereof. In some embodiments, the compound of Formula (I) is Compound IV or an isotopic variant, pharmaceutically acceptable salt, solvate, hydrate, or prodrug thereof. In some embodiments, the compound of Formula (I) is Compound V or an isotopic variant, pharmaceutically acceptable salt, solvate, hydrate, or prodrug thereof. In some embodiments, the compound of Formula (I) is Compound VI or an isotopic variant, pharmaceutically acceptable salt, solvate, hydrate, or prodrug thereof. In some embodiments, the compound of Formula (I) is Compound VII or an isotopic variant, pharmaceutically acceptable salt, solvate, hydrate, or prodrug thereof. In some embodiments, the compound of Formula (I) is Compound VIII or an isotopic variant, pharmaceutically acceptable salt, solvate, hydrate, or prodrug thereof. In some embodiments, the compound of Formula (I) is Compound IX or an isotopic variant, pharmaceutically acceptable salt, solvate, hydrate, or prodrug thereof. In some embodiments, the compound of Formula (I) is Compound X or an isotopic variant, pharmaceutically acceptable salt, solvate, hydrate, or prodrug thereof. In some embodiments, the compound of Formula (I) is Compound XI or an isotopic variant, pharmaceutically acceptable salt, solvate, hydrate, or prodrug thereof. In some embodiments, the compound of Formula (I) is Compound XII or an isotopic variant, pharmaceutically acceptable salt, solvate, hydrate, or prodrug thereof. In some embodiments, the compound of Formula (I) is Compound XIII or an isotopic variant, pharmaceutically acceptable salt, solvate, hydrate, or prodrug thereof. In some embodiments, the compound of Formula (I) is Compound XIV or an isotopic variant, pharmaceutically acceptable salt, solvate, hydrate, or prodrug thereof. In some embodiments, the compound of Formula (I) is Compound XV or an isotopic variant, pharmaceutically acceptable salt, solvate, hydrate, or prodrug thereof. In some embodiments, the compound of Formula (I) is Compound XVI or an isotopic variant, pharmaceutically acceptable salt, solvate, hydrate, or prodrug thereof. In some embodiments, the PD-1 or PD-L1 inhibitor is pidilizumab, nivolumab, pembrolizumab, atezolizumab, avelumab, BMS-936559, BGB-A317, PDR001, REGN2810, or durvalumab. In other embodiments, the PD-1 or PD-L1 inhibitor is nivolumab, pembrolizumab, atezolizumab, BGB-A317, PDR001, REGN2810, or avelumab. In some embodiments, the PD-1 or PD-L1 inhibitor is pidilizumab, nivolumab, pembrolizumab, atezolizumab, avelumab, BMS-936559, or durvalumab. In other embodiments, the PD-1 or PD-L1 inhibitor is nivolumab, pembrolizumab, atezolizumab, or avelumab.

In some embodiments, the proliferative disease is cancer. In certain embodiments, the proliferative disease is hematological cancer. In certain embodiments, the proliferative disease is a cancer of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system.

In certain embodiments, the cancer treatable with the methods provided herein includes, but is not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, non-secretory myeloma, osteosclerotic myeloma, plasma cell leukemia, solitary plasmacytoma, and extramedullary plasmacytoma; (6) Waldenstrom's macroglobulinernia; (7) monoclonal gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, aligodendrogliorna, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mutinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prol actin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, nonserninoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; (42) reproductive cancers, such as cervical cancer, uterus cancer, ovarian cancer, or testicular cancer; (43) esophagus cancer; (44) laryngeal cancer; (45) head and neck cancer (such as mouth, nose, throat, larynx, sinuses, or salivary glands cancer); and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America). In some embodiments, the cancer is non-small cell lung cancer, melanoma, renal cell cancer, head and neck cancer, colon cancer, or mesothelioma. In some embodiments, the cancer is non-small cell lung cancer. In some embodiments, the cancer is melanoma.

In certain embodiments, provided herein are methods of treating a hematological malignancy with a combination of an effective amount of a compound of Formula (I), or an isotopic variant thereof; or a pharmaceutically acceptable salt, solvate, hydrate, or prodrug thereof and an effective amount of PD-1 or PD-L1 inhibitor in a patient. In certain embodiments, the hematological malignancy is a leukemia, a lymphoma, a myeloma, a non-Hodgkin's lymphoma, a Hodgkin's lymphoma, T-cell malignancy, or a B-cell malignancy. In some embodiments, the hematological malignancy is Hodgkin's lymphoma. In some embodiments, the hematological malignancy is chronic lymphocytic leukemia, follicular lymphoma, diffuse large B-cell lymphoma, or non-Hodgkin's lymphoma. In some embodiments, the hematological malignancy is chronic lymphocytic leukemia or non-Hodgkin's lymphoma. In some embodiments, the hematological malignancy is chronic lymphocytic leukemia. In other embodiments, the hematological malignancy is non-Hodgkin's lymphoma. In some embodiments, the hematological malignancy is follicular lymphoma. In other embodiments, the hematological malignancy is diffuse large B-cell lymphoma. In some embodiments, the compound of Formula (I) is Compound I or an isotopic variant, pharmaceutically acceptable salt, solvate, hydrate, or prodrug thereof. In some embodiments, the compound of Formula (I) is Compound II or an isotopic variant, pharmaceutically acceptable salt, solvate, hydrate, or prodrug thereof. In some embodiments, the compound of Formula (I) is Compound III or an isotopic variant, pharmaceutically acceptable salt, solvate, hydrate, or prodrug thereof. In some embodiments, the compound of Formula (I) is Compound IV or an isotopic variant, pharmaceutically acceptable salt, solvate, hydrate, or prodrug thereof. In some embodiments, the compound of Formula (I) is Compound V or an isotopic variant, pharmaceutically acceptable salt, solvate, hydrate, or prodrug thereof. In some embodiments, the compound of Formula (I) is Compound VI or an isotopic variant, pharmaceutically acceptable salt, solvate, hydrate, or prodrug thereof. In some embodiments, the compound of Formula (I) is Compound VII or an isotopic variant, pharmaceutically acceptable salt, solvate, hydrate, or prodrug thereof. In some embodiments, the compound of Formula (I) is Compound VIII or an isotopic variant, pharmaceutically acceptable salt, solvate, hydrate, or prodrug thereof. In some embodiments, the compound of Formula (I) is Compound IX or an isotopic variant, pharmaceutically acceptable salt, solvate, hydrate, or prodrug thereof. In some embodiments, the compound of Formula (I) is Compound X or an isotopic variant, pharmaceutically acceptable salt, solvate, hydrate, or prodrug thereof. In some embodiments, the compound of Formula (I) is Compound XI or an isotopic variant, pharmaceutically acceptable salt, solvate, hydrate, or prodrug thereof. In some embodiments, the compound of Formula (I) is Compound XII or an isotopic variant, pharmaceutically acceptable salt, solvate, hydrate, or prodrug thereof. In some embodiments, the compound of Formula (I) is Compound XIII or an isotopic variant, pharmaceutically acceptable salt, solvate, hydrate, or prodrug thereof. In some embodiments, the compound of Formula (I) is Compound XIV or an isotopic variant, pharmaceutically acceptable salt, solvate, hydrate, or prodrug thereof. In some embodiments, the compound of Formula (I) is Compound XV or an isotopic variant, pharmaceutically acceptable salt, solvate, hydrate, or prodrug thereof. In some embodiments, the compound of Formula (I) is Compound XVI or an isotopic variant, pharmaceutically acceptable salt, solvate, hydrate, or prodrug thereof.

In certain embodiments, the hematological malignancy is a T-cell malignancy. In certain embodiments, T-cell malignancies include peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

In certain embodiments, the hematological malignancy is a B-cell malignancy. In certain embodiments, B-cell malignancies include acute lymphoblastic leukemia (ALL), acute myelogenous leukemia (AML), chronic myelogenous leukemia (CML), acute monocytic leukemia (AMoL), chronic lymphocytic leukemia (CLL), high-risk chronic lymphocytic leukemia (CLL), small lymphocytic lymphoma (SLL), high-risk small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In certain embodiments, the B-cell malignancy is diffuse large B-cell lymphoma (DLBCL). In certain embodiments, the hematological malignancy is diffuse large B-cell lymphoma (DLBCL). In certain embodiments, the DLBCL is an activated B-cell DLBCL (ABC-DLBCL), a germinal center B-cell like DLBCL (GBC-DLBCL), a double hit DLBCL (DH-DLBCL), or a triple hit DLBCL (TH-DLBCL). In certain embodiments, the hematological malignancy is relapsed-refractory diffuse large B-cell lymphoma (r/r DLBCL).

In certain embodiments, the hematological malignancy is a relapsed or refractory hematological malignancy. In certain embodiments, the relapsed or refractory hematological malignancy is a relapsed or refractory T-cell malignancy. In certain embodiments, the relapsed or refractory hematological malignancy is a relapsed or refractory B-cell malignancy.

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration as described elsewhere herein.

Dosages and Dosing Regimens

In certain embodiments, the methods provided herein comprise administering a compound of Formula (I), or an isotopic variant thereof; or a pharmaceutically acceptable salt, solvate, hydrate, or prodrug thereof and a PD-1 or PD-L1 inhibitor to a patient simultaneously or sequentially by the same or different routes of administration.

The suitability of a particular route of administration employed for a particular active agent will depend on the active agent itself (e.g., whether it can be administered orally without decomposing prior to entering the blood stream) and the disease being treated. Recommended routes of administration for the second active agents are known to those of ordinary skill in the art. See, e.g., Physicians' Desk Reference, 1755-1760 (56th ed., 2002).

In certain embodiments, the compound of Formula (I), or an isotopic variant thereof, or a pharmaceutically acceptable salt, solvate, hydrate, or prodrug thereof and a PD-1 or PD-L1 inhibitor are administered simultaneously, at essentially the same time, or sequentially. If administration takes place sequentially, the PD-1 or PD-L1 inhibitor may be administered before or after administration of a compound of Formula (I), or an isotopic variant thereof, or a pharmaceutically acceptable salt, solvate, hydrate, or prodrug thereof. In some embodiments, the PD-1 or PD-L1 inhibitor is administered before administration of a compound of Formula (I), or an isotopic variant thereof, or a pharmaceutically acceptable salt, solvate, hydrate, or prodrug thereof. In some embodiments, the PD-1 or PD-L1 inhibitor is administered simultaneously with administration of a compound of Formula (I), an isotopic variant thereof; or a pharmaceutically acceptable salt, solvate, hydrate, or prodrug thereof. In some embodiments, the PD-1 or PD-L1 inhibitor is administered after the administration of a compound of Formula (I), an isotopic variant thereof; or a pharmaceutically acceptable salt, solvate, hydrate, or prodrug thereof.

In certain embodiments, a compound of Formula (I), or an isotopic variant thereof, or a pharmaceutically acceptable salt, solvate, hydrate, or prodrug thereof and the PD-1 or PD-L1 inhibitor need not be administered by means of the same vehicle. In some embodiments, the PD-1 or PD-L1 inhibitor and a compound of Formula (I), or an isotopic variant thereof; or a pharmaceutically acceptable salt, solvate, hydrate, or prodrug thereof are administered in different vehicles. The PD-1 or PD-L1 inhibitor may be administered one or more times, and the number of administrations of each component of the combination may be the same or different. In addition, a compound of Formula (I), or an isotopic variant thereof, or a pharmaceutically acceptable salt, solvate, hydrate, or prodrug thereof and the PD-1 or PD-L1 inhibitor need not be administered at the same site.

In some instances, the methods described herein further comprise administering the PI3K inhibitor in combination with PD-1 or PD-L1 inhibitor to the subject or patient in need thereof in multiple cycles repeated on a regular schedule with periods of rest in between each cycle. For example, in some instances, treatment is given for one week followed by three weeks of rest is one treatment cycle.

In some instances, a cycle comprises administration of the PI3K inhibitor at the same time as administration of the PD-1 or PD-L1 inhibitor. In some instances, the PI3K inhibitor and the PD-1 or PD-L1 inhibitor are administered for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days.

In some instances, a cycle comprises administration of the PI3K inhibitor first followed by administration of the PD-1 or PD-L1 inhibitor second. In some instances, the PI3K inhibitor is administered for about 1 day, about 2 days, about 3 days, about 4 days, about 5 days, about 6 days, about 7 days, about 8 days, about 9 days, about 10 days, about 11 days, about 12 days, about 13 days, or about 14 days followed by administration of the PD-1 or PD-L1 inhibitor for about 1 day, about 2 days, about 3 days, about 4 days, about 5 days, about 6 days, about 7 days, about 8 days, about 9 days, about 10 days, about 11 days, about 12 days, about 13 days, or about 14 days.

In some instances, a cycle comprises administration of the PI3K inhibitor first followed by concurrent administration of the PD-1 or PD-L1 inhibitor. In some instances, the PI3K inhibitor is first administered for about 1 day, about 2 days, about 3 days, about 4 days, about 5 days, about 6 days, about 7 days, about 8 days, about 9 days, about 10 days, about 11 days, about 12 days, about 13 days, or about 14 days followed by the concurrent administration of the PD-1 or PD-L1 inhibitor for about 1 day, about 2 days, about 3 days, about 4 days, about 5 days, about 6 days, about 7 days, about 8 days, about 9 days, about 10 days, about 11 days, about 12 days, about 13 days, or about 14 days. In some instances, the PI3K inhibitor is first administered for about 1 day, about 2 days, about 3 days, about 4 days, about 5 days, about 6 days, or about 7 days followed by the concurrent administration of the PD-1 or PD-L1 inhibitor for about 1 day, about 2 days, about 3 days, about 4 days, about 5 days, about 6 days, about 7 days, about 8 days, about 9 days, about 10 days, about 11 days, about 12 days, about 13 days, or about 14 days. In some instances, the PI3K inhibitor is first administered for about 7 days followed by the concurrent administration of the PD-1 or PD-L1 inhibitor for about 1 day, about 2 days, about 3 days, about 4 days, about 5 days, about 6 days, about 7 days, about 8 days, about 9 days, about 10 days, about 11 days, about 12 days, about 13 days, or about 14 days. In some instances, the PI3K inhibitor is first administered for about 7 days followed by the concurrent administration of the PD-1 or PD-L1 inhibitor for about 10 days, about 11 days, about 12 days, about 13 days, or about 14 days.

In some instances, a cycle comprises administration of the PI3K inhibitor only. In some instances, the PI3K inhibitor is administered for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days.

In some instances, a cycle comprises administration of the PD-1 or PD-L1 inhibitor only. In some instances, the PD-1 or PD-L1 inhibitor is administered for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days.

In some instances, the method for multiple cycle chemotherapy comprises the administration of a second cycle within about 60 days or about 3 months. In some instances, the method for multiple cycle chemotherapy comprises the administration of a second cycle within 50 days. In another instance, the second cycle is administered within 45, 40, 35, 30, 25, 21, 20, 15, 14, 10, 9, 8, 7, 6, 5, 4, 3, 2 or 1 day(s) of the first cycle. In some embodiments, the administration of any additional cycles is within 50 days of the previous cycle. In some embodiments, the administration of any additional cycles is within 10 days of the previous cycle. In some embodiments, the administration of any additional cycles is within 9 days of the previous cycle. In some embodiments, the administration of any additional cycles is within 8 days of the previous cycle. In some embodiments, the administration of any additional cycles is within 7 days of the previous cycle. In some embodiments, the administration of any additional cycles is within 6 days of the previous cycle.

In some embodiments, the administration of any additional cycles is within 5 days of the previous cycle. In some embodiments, the administration of any additional cycles is within 4 days of the previous cycle. In some embodiments, the administration of any additional cycles is within 3 days of the previous cycle. In some embodiments, the administration of any additional cycles is within 2 days of the previous cycle. In some embodiments, the administration of any additional cycles is within 1 day of the previous cycle. In another embodiment, the additional cycle is administered within 45, 40, 35, 30, 25, 21, 20, 15, 14, 10, 9, 8, 7, 6, 5, 4, 3, 2, or 1 days of the previous cycle.

The length of a treatment cycle depends on the treatment being given. In some embodiments, the length of a treatment cycle ranges from two to six weeks. In some embodiments, the length of a treatment cycle ranges from four to six weeks. In some embodiments, the length of a treatment cycle is 28 days. In some embodiments, the length of a treatment cycle is 56 days. In some embodiments, a treatment cycle lasts one, two, three, or four weeks. In some embodiments, a treatment cycle lasts four weeks. The number of treatment doses scheduled within each cycle also varies depending on the drugs being given.

In some instances, the method for the administration of multiple compounds comprises administering compounds within 48 hours or less of each other. In some embodiments administration occurs within 24 hours, 12 hours, 6 hours, 3 hours, 1 hour, or 15 minutes. In some instances, the compounds are administered simultaneously. One example of simultaneous administration is the injection of one compound immediately before, after, or during the oral administration of the second compound, immediately referring to a time less than about 5 minutes.

In some instances, the method for the administration of multiple compounds occurs in a sequential order, wherein the PI3K inhibitor is administered before the PD-1 or PD-L1 inhibitor. In another instance, the PD-1 or PD-L1 inhibitor is administered before the PI3K inhibitor.

In some instances, the method for administering the PI3K inhibitor is oral and the method for administering the PD-1 or PD-L1 inhibitor is by injection. In some instances, the method for administering the PI3K inhibitor is by inhalation and the method for administering the PD-1 or PD-L1 inhibitor is by injection. In some instances, the method for administering the PI3K inhibitor is by injection and the method for administering the PD-1 or PD-L1 inhibitor is by injection.

In certain embodiments, a compound of Formula (I), or an isotopic variant thereof; or a pharmaceutically acceptable salt, solvate, hydrate, or prodrug thereof and a PD-1 or PD-L1 inhibitor are cyclically administered to a patient. As discussed above, cycling therapy involves the administration of an active agent or a combination of active agents for a period of time, followed by a rest for a period of time, and repeating this sequential administration. In some embodiments, cycling therapy reduces the development of resistance to one or more of the therapies, avoid or reduce the side effects of one of the therapies, and/or improves the efficacy of the treatment.

In some embodiments, the compound of Formula (I) is administered daily, every other day, every other day 3 times a week, every 2 weeks, every 3 weeks, every 4 weeks, every 5 weeks, every 3 days, every 4 days, every 5 days, every 6 days, weekly, bi-weekly, 3 times a week, 4 times a week, 5 times a week, 6 times a week, once a month, twice a month, 3 times a month, once every 2 months, once every 3 months, once every 4 months, once every 5 months, or once every 6 months. In some embodiments, the compound of Formula (I) is administered daily.

In some embodiments, the PD-1 or PD-L1 inhibitor is administered daily, every other day, every other day 3 times a week, every 3 days, every 4 days, every 5 days, every 6 days, weekly, every 2 weeks, every 3 weeks, every 4 weeks, every 5 weeks, bi-weekly, 3 times a week, 4 times a week, 5 times a week, 6 times a week, once a month, twice a month, 3 times a month, once every 2 months, once every 3 months, once every 4 months, once every 5 months, or once every 6 months.

In some instances, the compound of Formula (I) or the PD-1 or PD-L1 inhibitor is optionally given continuously; alternatively, the dose of drug being administered is temporarily reduced or temporarily suspended for a certain length of time (i.e., a "drug holiday"). In some embodiments, the length of the drug holiday varies between 2 days and 1 year, including by way of example only, 2 days, 3 days, 4 days, 5 days, 6 days, 7 days, 8 days, 9 days, 10 days, 12 days, 14 days, 15 days, 20 days, 21 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

In certain embodiments, in the treatment, prevention, or amelioration of one or more symptoms of the disorders, diseases, or conditions described herein, an appropriate dosage level of a compound of Formula (I), or an isotopic variant thereof; or a pharmaceutically acceptable salt, solvate, hydrate, or prodrug thereof generally is ranging from about 1 to about 1000 mg, from about 1 to about 500 mg, from about 5 to about 500 mg, from about 5 to about 200 mg, from about 5 to about 250 mg or from about 10 to about 150 mg which can be administered in single or multiple doses. In certain embodiments, the compound of Formula (I), or an isotopic variant thereof; or a pharmaceutically acceptable salt, solvate, hydrate, or prodrug thereof is administered in an amount of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 450 or 500 mg. In certain embodiments, the compound of Formula (I), or an isotopic variant thereof; or a pharmaceutically acceptable salt, solvate, hydrate, or prodrug thereof is administered in an amount of about 1, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 225, about 250, about 275, about 300, about 325, about 350, about 375, about 400, about 450, or about 500 mg. In certain embodiments, the compound of Formula (I), or an isotopic variant thereof; or a pharmaceutically acceptable salt, solvate, hydrate, or prodrug thereof is administered in an amount of about 30 mg. In certain embodiments, the compound of Formula (I), or an isotopic variant thereof; or a pharmaceutically acceptable salt, solvate, hydrate, or prodrug thereof is administered in an amount of about 45 mg. In certain embodiments, the compound of Formula (I), or an isotopic variant thereof; or a pharmaceutically acceptable salt, solvate, hydrate, or prodrug thereof is administered in an amount of about 60 mg. In certain embodiments, the compound of Formula (I), or an isotopic variant thereof; or a pharmaceutically acceptable salt, solvate, hydrate, or prodrug thereof is administered in an amount of about 90 mg. In certain embodiments, the compound of Formula (I), or an isotopic variant thereof; or a pharmaceutically acceptable salt, solvate, hydrate, or prodrug thereof is administered in an amount of about 120 mg. In certain embodiments, the compound of Formula (I), or an isotopic variant thereof; or a pharmaceutically acceptable salt, solvate, hydrate, or prodrug thereof is administered in an amount of about 150 mg. In certain embodiments, the compound of Formula (I), or an isotopic variant thereof; or a pharmaceutically acceptable salt, solvate, hydrate, or prodrug thereof is administered in an amount of about 180 mg. In certain embodiments, the compound of Formula (I), or an isotopic variant thereof; or a pharmaceutically acceptable salt, solvate, hydrate, or prodrug thereof is administered in an amount of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 450 or 500 mg/day. In certain embodiments, the compound of Formula (I), or an isotopic variant thereof; or a pharmaceutically acceptable salt, solvate, hydrate, or prodrug thereof is administered in an amount of about 30 mg/day. In certain embodiments, the compound of Formula (I), or an isotopic variant thereof; or a pharmaceutically acceptable salt, solvate, hydrate, or prodrug thereof is administered in an amount of about 45 mg/day. In certain embodiments, the compound of Formula (I), or an isotopic variant thereof; or a pharmaceutically acceptable salt, solvate, hydrate, or prodrug thereof is administered in an amount of about 60 mg/day. In certain embodiments, the compound of Formula (I), or an isotopic variant thereof; or a pharmaceutically acceptable salt, solvate, hydrate, or prodrug thereof is administered in an amount of about 90/day mg. In certain embodiments, the compound of Formula (I), or an isotopic variant thereof; or a pharmaceutically acceptable salt, solvate, hydrate, or prodrug thereof is administered in an amount of about 120/day mg. In certain embodiments, the compound of Formula (I), or an isotopic variant thereof; or a pharmaceutically acceptable salt, solvate, hydrate, or prodrug thereof is administered in an amount of about 150/day mg. In certain embodiments, the compound of Formula (I), or an isotopic variant thereof; or a pharmaceutically acceptable salt, solvate, hydrate, or prodrug thereof is administered in an amount of about 180/day mg.

For oral administration, the pharmaceutical compositions provided herein can be formulated in the form of tablets or capsules containing from about 1.0 to about 1,000 mg of a compound of Formula (I), or an isotopic variant thereof; or a pharmaceutically acceptable salt, solvate, hydrate, or prodrug thereof, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the compound of Formula (I), or an isotopic variant thereof; or a pharmaceutically acceptable salt, solvate, hydrate, or prodrug thereof for the symptomatic adjustment of the dosage to the patient to be treated. In some embodiments, the pharmaceutical compositions provided herein can be formulated in the form of tablets containing about 60 mg of a compound of Formula (I), or an isotopic variant thereof; or a pharmaceutically acceptable salt, solvate, hydrate, or prodrug thereof. The pharmaceutical compositions can be administered on a regimen of 1 to 4 times per day, including once, twice, three times, and four times per day. In some embodiments, the compound of Formula (I), or an isotopic variant thereof; or a pharmaceutically acceptable salt, solvate, hydrate, or prodrug thereof is administered once per day. In some embodiments, about 30 mg, about 45 mg, or about 60 mg of the compound of Formula (I), or an isotopic variant thereof; or a pharmaceutically acceptable salt, solvate, hydrate, or prodrug thereof is administered once per day. In some embodiments, the compound of Formula (I), or an isotopic variant thereof; or a pharmaceutically acceptable salt, solvate, hydrate, or prodrug thereof is administered to a patient in need thereof in an amount of about 60 mg daily for 28 days or 56 days. In certain specific embodiments, a compound of Formula (I), or an isotopic variant thereof; or a pharmaceutically acceptable salt, solvate, hydrate, or prodrug thereof is administered to a patient in need thereof in an amount of about 60 mg daily for 28 days. In other specific embodiments, a compound of Formula (I), or an isotopic variant thereof; or a pharmaceutically acceptable salt, solvate, hydrate, or prodrug thereof is administered to a patient in need thereof in an amount of about 60 mg daily for 56 days.

In the methods of treatment, prevention, or amelioration of one or more symptoms of the disorders, diseases, or conditions described herein, an appropriate dosage level of a PD-1 or PD-L1 inhibitor generally is ranging from about 0.1 to 2000 mg per day. In some embodiments, 1-500 mg once or multiple times per day is effective to obtain the desired results.

In certain embodiments, the PD-1 or PD-L1 inhibitor is pidilizumab and the amount of pidilizumab that is administered is from about 10 mg/day up to, and including, 1000 mg/day. In certain embodiments, the amount of pidilizumab that is administered is from about 10 mg/day to 600 mg/day. In certain embodiments, the amount of pidilizumab that is administered is from about 100 mg/day to 600 mg/day. In certain embodiments, the amount of pidilizumab that is administered per day is about 10 mg, about 50 mg, about 100 mg, about 120 mg, about 240 mg, about 420 mg or about 560 mg.

In certain embodiments, the methods described herein further comprise administering pidilizumab intravenously at a dosage of 1-10 mg/kg each week. In certain embodiments, pidilizumab is administered intravenously at a dosage of 3 mg/kg each week. In another embodiment, pidilizumab is administered intravenously at a dosage of about 100 mg, about 150 mg, about 240 mg, about 360 mg or about 450 mg each week.

In certain embodiments, the PD-1 or PD-L1 inhibitor is nivolumab and the amount of nivolumab that is administered is from about 10 mg/day up to, and including, 1000 mg/day. In certain embodiments, the amount of nivolumab that is administered is from about 10 mg/day to 600 mg/day. In certain embodiments, the amount of nivolumab that is administered is from about 100 mg/day to 600 mg/day. In certain embodiments, the amount of nivolumab that is administered per day is about 10 mg, about 60 mg, about 120 mg, about 180 mg, about 240 mg, about 420 mg or about 560 mg.

In certain embodiments, the methods described herein further comprise administering nivolumab intravenously at a dosage of 1-10 mg/kg every two weeks. In certain embodiments, nivolumab is administered intravenously at a dosage of 3 mg/kg every two weeks. In certain embodiments, 3 mg/kg of nivolumab is administered as an intravenous infusion over 60 minutes every two weeks. In another embodiment, the amount of nivolumab that is administered is about 100 mg, about 150 mg, about 240 mg, about 360 mg or about 450 mg every two weeks.

In certain embodiments, the PD-1 or PD-L1 inhibitor is pembrolizumab and the amount of pembrolizumab that is administered is from about 10 mg/day up to, and including, 1000 mg/day. In certain embodiments, the amount of pembrolizumab that is administered is from about 10 mg/day to 600 mg/day. In certain embodiments, the amount of pembrolizumab that is administered is from about 100 mg/day to 600 mg/day. In certain embodiments, the amount of pembrolizumab that is administered per day is about 10 mg, about 60 mg, about 120 mg, about 180 mg, about 240 mg, about 420 mg or about 560 mg.

In certain embodiments, the methods described herein further comprise administering pembrolizumab intravenously at a dosage of 1-10 mg/kg every three weeks. In certain embodiments, pembrolizumab is administered intravenously at a dosage of 2 mg/kg every three weeks. In certain embodiments, 2 mg/kg of pembrolizumab is administered as an intravenous infusion over 30 minutes every three weeks. In another embodiment, the amount of pembrolizumab that is administered is about 50 mg, about 100 mg, about 200 mg, about 300 mg or about 400 mg every three weeks.

In certain embodiments, the PD-1 or PD-L1 inhibitor is BGB-A317 and BGB-A317 is administered to a subject in need thereof with doses ranging from 0.5 to 10 mg/kg. In some embodiments, BGB-A317 is administered at a dosage of about 2 mg/kg or about 5 mg/kg. In some embodiments, BGB-A317 is administered at a dosage of about 2 mg/kg. In some embodiments, BGB-A317 is administered at a dosage of about 5 mg/kg.

In certain embodiments, the PD-1 or PD-L1 inhibitor is BGB-A317 and BGB-A317 is administered to a subject in need thereof with biweekly intravenous doses ranging from 0.5 to 10 mg/kg. In some embodiments, BGB-A317 is administered biweekly at a dosage of about 2 mg/kg or about 5 mg/kg. In some embodiments, BGB-A317 is administered biweekly at a dosage of about 2 mg/kg. In some embodiments, BGB-A317 is administered biweekly at a dosage of about 5 mg/kg. In some embodiments, BGB-A317 is administered biweekly at a dosage of about 2 mg/kg or about 5 mg/kg intravenously.

In some embodiments, BGB-A317 is administered intravenously once every three weeks at a dose ranging from about 0.5 to 10 mg/kg. In some embodiments, BGB-A317 is administered once every three weeks at a dosage of about 2 mg/kg or about 5 mg/kg. In some embodiments, BGB-A317 is administered once every three weeks at a dosage of about 2 mg/kg. In some embodiments, BGB-A317 is administered once every three weeks at a dosage of about 5 mg/kg. In some embodiments, BGB-A317 is administered once every three weeks at a dosage of about 2 mg/kg or about 5 mg/kg intravenously.

In some embodiments, BGB-A317 is administered to the subject in need thereof in an amount of about 200 mg or 300 mg. In some embodiments, BGB-A317 is administered to the subject in need thereof in an amount of about 200 mg once every two weeks. In some embodiments, BGB-A317 is administered to the subject in need thereof in an amount of about 300 mg once every two weeks. In some embodiments, BGB-A317 is administered to the subject in need thereof in an amount of about 200 mg once every three weeks. In some embodiments, BGB-A317 is administered to the subject in need thereof in an amount of about 300 mg once every three weeks.

In some embodiments, the PD-1 or PD-L1 inhibitor is PDR001 and PDR001 is administered to a subject in need thereof via intravenous infusion over 30 mins. In other embodiments, PDR001 is administered to a subject in need thereof via intravenous infusion for up to 2 hours. In some embodiments, PDR001 is administered to a subject in need thereof once every 4 or 8 weeks. In certain embodiments, PDR001 is administered to a subject in need thereof once every 4 weeks. In other embodiments, PDR001 is administered to a subject in need thereof once every 8 weeks.

In some embodiments, the PD-1 or PD-L1 inhibitor is REGN2810 and REGN2810 is administered to a subject in need thereof intravenously every 2 weeks. In some embodiments, REGN2810 is administered to a subject in need thereof in an amount of about 200 mg. In some embodiments, REGN2810 is administered to a subject in need thereof in an amount of about 3 mg/kg. In other embodiments, REGN2810 is administered to a subject in need thereof in an amount of about 1 mg/kg. In some embodiments, REGN2810 is administered to a subject in need thereof in an amount of about 200 mg once every two weeks. In some embodiments, REGN2810 is administered to a subject in need thereof in an amount of about 3 mg/kg once every two weeks. In other embodiments, REGN2810 is administered to a subject in need thereof in an amount of about 1 mg/kg once every two weeks.

In certain embodiments, the PD-1 or PD-L1 inhibitor is atezolizumab and the amount of atezolizumab that is administered is from about 10 mg/day up to, and including, 1200 mg/day. In certain embodiments, the amount of atezolizumab that is administered is from about 10 mg/day to 600 mg/day. In certain embodiments, the amount of atezolizumab that is administered is from about 100 mg/day to 600 mg/day. In certain embodiments, the amount of atezolizumab that is administered per day is about 10 mg, about 60 mg, about 120 mg, about 180 mg, about 240 mg, about 420 mg or about 560 mg.

In certain embodiments, the methods described herein further comprise administering atezolizumab at a dosage of 1200 mg/20 mL in a single dose. In certain embodiments, atezolizumab is administered at a dosage of 15 mg/kg in a single dose. In some embodiments, atezolizumab is administered at a dosage of 1200 mg as an intravenous infusion. In some embodiments, atezolizumab is administered at a dosage of 1200 mg as an intravenous infusion every 3 weeks. In some embodiments, atezolizumab is administered at a dosage of 1200 mg as an intravenous infusion over 60 minutes every 3 weeks. In another embodiment, the amount of atezolizumab that is administered is about 600 mg, about 900 mg, about 1000 mg, about 1100 mg, about 1200 mg, about 1300 mg, about 1500 mg, or about 1800 mg in a single dose.

In certain embodiments, the PD-1 or PD-L1 inhibitor is avelumab and the amount of avelumab that is administered is from about 10 mg/day up to, and including, 1000 mg/day. In certain embodiments, the amount of avelumab that is administered is from about 10 mg/day to 600 mg/day. In certain embodiments, the amount of avelumab that is administered is from about 100 mg/day to 600 mg/day. In certain embodiments, the amount of avelumab that is administered per day is about 10 mg, about 50 mg, about 100 mg, about 300 mg, about 500 mg, about 700 mg or about 900 mg.

In certain embodiments, the methods described herein further comprise administering avelumab at a dosage of 10 mg/kg every two weeks. In some embodiments, 10 mg/kg of avelumab is administered as an intravenous infusion every two weeks. In some embodiments, 10 mg/kg of avelumab is administered as an intravenous infusion over 60 minutes every two weeks. In certain embodiments, avelumab is administered at a dosage of 20 mg/kg every two weeks. In another embodiment, the amount of avelumab that is administered is about 100 mg, 300 mg, 500 mg, 750 mg, 1200 mg or 1500 mg in a every two weeks. In some instances, the patient is premedicated with acetaminophen and/or an antihistamine for the first 4 infusions and subsequently as needed.

In certain embodiments, the PD-1 or PD-L1 inhibitor is BMS-936559 and the amount of BMS-936559 that is administered is from about 10 mg/day up to, and including, 1000 mg/day. In certain embodiments, the amount of BMS-936559 that is administered is from about 10 mg/day to 600 mg/day. In certain embodiments, the amount of BMS-936559 that is administered is from about 100 mg/day to 600 mg/day. In certain embodiments, the amount of BMS-936559 that is administered per day is about 10 mg, about 30 mg, about 80 mg, about 100 mg, about 200 mg, about 300 mg or about 500 mg.

In certain embodiments, the PD-1 or PD-L1 inhibitor is BMS-936559 and the amount of BMS-936559 that is administered is 3 mg/kg every two weeks. In certain embodiments, the amount of BMS-936559 that is administered is 2 mg/kg every two weeks. In another embodiment, the amount of BMS-936559 that is administered is about 50 mg, 100 mg, 100 mg, 250 mg, 350 mg or 500 mg every two weeks.

In certain embodiments, the PD-1 or PD-L1 inhibitor is durvalumab and the amount of durvalumab that is administered is from about 10 mg/day up to, and including, 1000 mg/day. In certain embodiments, the amount of durvalumab that is administered is from about 10 mg/day to 600 mg/day. In certain embodiments, the amount of durvalumab that is administered is from about 100 mg/day to 600 mg/day. In certain embodiments, the amount of durvalumab that is administered per day is about 10 mg, about 50 mg, about 100 mg, about 300 mg, about 500 mg, about 700 mg or about 900 mg.

In certain embodiments, the PD-1 or PD-L1 inhibitor is durvalumab and the amount of durvalumab that is administered is 10 mg/kg every two weeks. In certain embodiments, the amount of durvalumab that is administered is 20 mg/kg every four weeks. In another embodiment, the amount of durvalumab that is administered is about 100 mg, 400 mg, 800 mg, 1200 mg, 1500 mg or 2000 mg in a single dose.

In certain embodiments, a PD-1 or PD-L1 inhibitor is administered once per day, twice per day, or three times per day. In certain embodiments, the PD-1 or PD-L1 inhibitor is administered once per day. In certain embodiments, the PD-1 or PD-L1 inhibitor is administered once per day, twice per day, or three times per day. In certain embodiments, the PD-1 or PD-L1 inhibitor is administered once per day. In certain embodiments, the PD-1 or PD-L1 inhibitor is co-administered (e.g., in a single dosage form), once per day.

In certain embodiments, the PD-1 or PD-L1 inhibitor is administered once a week. In certain embodiments, the PD-1 or PD-L1 inhibitor is administered once every two, three, four or five weeks. In certain embodiments, the PD-1 or PD-L1 inhibitor is administered intravenously or through direct injection. In certain embodiments of the combination therapy described herein, one agent is administered orally and another agent is administered intravenously.

It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Additional Combination Therapy

In certain embodiments, the methods of combination therapy comprising a compound of Formula (I), an isotopic variant thereof; or a pharmaceutically acceptable salt, solvate, hydrate, or prodrug thereof and a PD-1 or PD-L1 inhibitor can also be combined or used in combination with a third agent or therapies useful in the treatment, prevention, or amelioration of one or more symptoms of a proliferative disorders, diseases, or conditions.

Suitable third agent of therapies include, but are not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and xirnelagatran, (7) antidiabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma monists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., nonsteroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid secjuestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) famesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat, and (54) other miscellaneous agents, such as, hydroxyurea, procarbazine, mitotane, hexamethylmelamine, and gold compounds.

In certain embodiments, the third therapies that may be used in combination with the methods provided herein include, but are not limited to, surgery, endocrine therapy, biologic response modifiers (e.g., interferons, interleukins, and tumor necrosis factor (TNF)), hyperthermia and cryotherapy, and agents to attenuate any adverse effects (e.g., antiemetics).

In certain embodiments, the third therapeutic agents that may be used in combination with the compounds provided herein include, but are not limited to, alkylating drugs (mechlorethamine, chlorambucil, cyclophosphamide, melphalan, and ifosfamide), antimetabolites (cytarabine (also known as cytosine arabinoside or Ara-C), and methotrexate), purine antagonists and pyrimidine antagonists (6-mercaptopurine, 5-fluorouracil, cytarbine, and gemcitabine), spindle poisons (vinblastine, vincristine, and vinorelbine), podophyllotoxins (etoposide, irinotecan, and topotecan), antibiotics (daunorubicin, doxorubicin, bleomycin, and mitomycin), nitrosoureas (carmustine and lomustine), enzymes (asparaginasc), and hormones (tamoxifen, leuprolide, flutamide, and megestrol), imatinib, adriamycin, dexamethasone, and cyclophosphamide. For a more comprehensive discussion of updated cancer therapies; See, http://www.nci.nih.gov/, a list of the FDA approved oncology drugs at http://www.fda.gov/cder/cancer/dniglistframe.htm, and The Merck Manual, Seventeenth Ed. 1999, the entire contents of which are hereby incorporated by reference.

In another embodiment, methods provided herein comprise administration of a compound of Formula (I), or an isotopic variant thereof, or a pharmaceutically acceptable salt, solvate, hydrate, or prodrug thereof and a PD-1 or PD-L1 inhibitor, together with administration of one or more chemotherapeutic agents and/or therapies selected from: alkylation agents (e.g., cisplatin, carboplatin); antimetabolites (e.g., methotrexate and 5-FU); antitumor antibiotics (e.g., adriamymycin and bleomycin); antitumor vegetable alkaloids (e.g., taxol and etoposide); antitumor hormones (e.g., dexamethasone and tamoxifen); antitumor immunological agents (e.g., interferon $\alpha$, $\beta$, and $\gamma$); radiation therapy; and surgery. In certain embodiments, the one or more chemotherapeutic agents and/or therapies are administered to the subject before, during, or after the administration of a compound of Formula (I), or an isotopic variant thereof, or a pharmaceutically acceptable salt, solvate, hydrate, or prodrug thereof and a PD-1 or PD-L1 inhibitor.

Such other agents, or drugs, can be administered, by a route and in an amount commonly used therefor, simultaneously or sequentially with a compound of Formula (I), or an isotopic variant thereof; or a pharmaceutically acceptable salt, solvate, hydrate, or prodrug thereof and a PD-1 or PD-L1 inhibitor. When a compound of Formula (I) and a PD-1 or PD-L1 inhibitor are used contemporaneously with one or more other drugs, a pharmaceutical composition containing such other drugs in addition to the compound of Formula (I), or an isotopic variant thereof; or a pharmaceutically acceptable salt, solvate, hydrate, or prodrug thereof and a PD-1 or PD-L1 inhibitor can be utilized, but is not required. Accordingly, the pharmaceutical compositions provided herein include those that also contain one or more other active ingredients or therapeutic agents, in addition to a compound of Formula (I).

Pharmaceutical Compositions and Routes of Administration

Provided herein is a pharmaceutical composition comprising a compound of Formula (I), a PD-1 or PD-L1 inhibitor, and a pharmaceutically acceptable excipient, adjuvant, carrier, buffer, or stabilizer. In some embodiments, the compound of Formula (I) and a PD-1 or PD-L1 inhibitor are present in the same pharmaceutical composition. In some embodiments, the compound of Formula (I) and the PD-1 or PD-L1 inhibitor are in different pharmaceutical compositions.

In one embodiment, the pharmaceutical compositions are provided in a dosage form for oral administration, which comprise a compound provided herein, and one or more pharmaceutically acceptable excipients or carriers. The pharmaceutical compositions provided herein that are formulated for oral administration may be in tablet, capsule, powder, or liquid form. In some embodiments, a tablet comprises a solid carrier or an adjuvant. Liquid pharmaceutical compositions generally comprise a liquid carrier such as water, petroleum, animal or vegetable oils, mineral oil, or synthetic oil. Physiological saline solution, dextrose or other saccharide solution, or glycols such as ethylene glycol, propylene glycol, or polyethylene glycol may be included. In some embodiments, a capsule comprises a solid carrier such as gelatin.

In another embodiment, the pharmaceutical compositions are provided in a dosage form for parenteral administration, which comprise a compound provided herein, and one or more pharmaceutically acceptable excipients or carriers. Where pharmaceutical compositions may be formulated for intravenous, cutaneous or subcutaneous injection, the active ingredient will be in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. In some embodiments, preservatives, stabilizers, buffers, antioxidants, and/or other additives are included as required.

In yet another embodiment, the pharmaceutical compositions are provided in a dosage form for topical administration, which comprise a compound provided herein, and one or more pharmaceutically acceptable excipients or carriers.

The pharmaceutical compositions can also be formulated as modified release dosage forms, including delayed-, extended-, prolonged-, sustained-, pulsatile-, controlled-, accelerated-, fast-, targeted-, and programmed-release, and gastric retention dosage forms. These dosage forms can be prepared according to conventional methods and techniques known to those skilled in the art (see, *Remington: The Science and Practice of Pharmacy, supra; Modified-Release Drug Delivery Technology*, 2nd Edition, Rathbone et al., Eds., Marcel Dekker, Inc.: New York, N.Y., 2008).

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In certain embodiments, the pharmaceutical compositions provided herein further comprise one or more chemotherapeutic agents as defined herein.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SILO (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409, 239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimetboxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfate, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfate and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungi static concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutylmethacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and metliacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, buty] rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Phar-*

*macy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. In some embodiments, the emulsifier in a cream formulation is a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinyl alcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfate and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324;

6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate), polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinyl acetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxyethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, Multiparticulate Oral Drug Delivery; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Articles of Manufacture

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes one or more containers and a dosage form of a compound of Formula (I), or an isotopic variant thereof; or a pharmaceutically acceptable salt, solvate, hydrate, or prodrug thereof and a PD-1 or PD-L1 inhibitor.

In certain embodiments, the kit provided herein includes one or more containers and a dosage form of a compound of Formula (I), or an isotopic variant thereof; or a pharmaceutically acceptable salt, solvate, hydrate, or prodrug thereof and PD-1 or PD-L1 inhibitor. Kits provided herein can further include devices that are used to administer the active ingredients. Examples of such devices include, but are not limited to, syringes, needle-less injectors drip bags, patches, and inhalers.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

ADDITIONAL EMBODIMENTS

Embodiments include embodiment P1 to P31 following.

Embodiment P1

A method for treating or preventing a disease comprising administering:
(i) an effective amount of a compound of Formula (I);

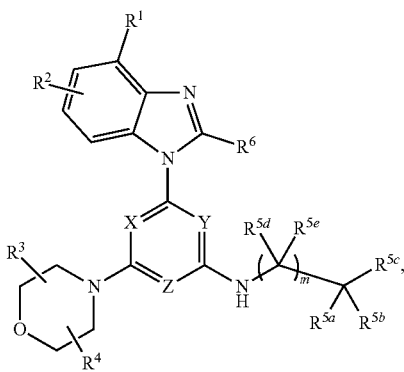

Formula (I)

or an enantiomer, a mixture of enantiomers, a mixture of two or more diastereomers, or an isotopic variant thereof; or a pharmaceutically acceptable salt, solvate, hydrate, or prodrug thereof; wherein:
X, Y, and Z are each independently N or $CR^X$, with the proviso that at least two of X, Y, and Z are nitrogen atoms; where $R^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$; wherein each R$^{1a}$, R$^{1b}$, R$^{1c}$, and R$^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) R$^{1b}$ and R$^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(C)NR$^{1b}$R$^{1c}$, or —S(O)$_2$NR$^{1b}$R$^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1a}$)NR$^{1b}$R$^{1c}$, —NR$^{1a}$S(O)R$^{1d}$, —NR$^{1a}$S(O)$_2$R$^{1d}$, —NR$^{1a}$S(C)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$, —

$R^{5c}$ is —(CR$^{5f}$R$^{5g}$)$_n$—(C$_{6-14}$ aryl) or —(CR$^{5f}$R$^{5g}$)$_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$; or —S(O)$_2$NR$^{1b}$R$^{1c}$; or (d) when one occurrence of R$^{5f}$ and one occurrence of R$^{5g}$ are attached to the same carbon atom, the R$^{5f}$ and R$^{5g}$ together with the carbon atom to which they are attached form a C$_{3-10}$ cycloalkyl or heterocyclyl;

R$^6$ is hydrogen, C$_{1-6}$ alkyl, —S—C$_{1-6}$ alkyl, —S(O)—C$_{1-6}$ alkyl, or —SO$_2$—C$_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl in R$^1$, R$^2$, R$^3$, R$^4$, R$^6$, R$^X$, R$^{1a}$, R$^{1b}$, R$^{1c}$, R$^{1d}$, R$^{5a}$, R$^{5b}$, R$^{5c}$, R$^{5d}$, R$^{5e}$, R$^{5f}$, and R$^{5g}$ is optionally substituted with one, two, three, four, or five substituents Q, wherein each substituent Q is independently selected from (a) oxo, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl, each of which is further optionally substituted with one, two, three, or four substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is further optionally substituted with one, two, three, or four substituents Q$^a$; or (iii) R$^b$ and R$^c$ together with the N atom to which they are attached form heterocyclyl, which is further optionally substituted with one, two, three, or four substituents Q$^a$;

wherein each Q$^a$ is independently selected from the group consisting of (a) oxo, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$_e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl; or wherein two substituents Q that are adjacent to each other optionally form a C$_{3-10}$ cycloalkenyl, C$_{6-14}$ aryl, heteroaryl, or heterocyclyl, each optionally substituted with one, two, three, or four substituents Q$^a$; and (ii) an effective amount of a PD-1 or PD-L1 inhibitor, wherein the disease is cancer.

Embodiment P2

The method of embodiment P1, wherein R$^{5b}$ is (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, or heteroaryl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —S(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

Embodiment P3

The method of embodiment P1, wherein R$^{5a}$ and R$^{5b}$ are each independently (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1a}$)NR$^{1b}$R$^{1c}$, —NR$^{1a}$S(C)R$^{1d}$, —NR$^{1a}$S(O)$_2$R$^{1d}$, —NR$^{1a}$S(C)NR$^{1b}$R$^{1c}$, —NR$^{1a}$S(O)$_2$NR$^{1b}$R$^{1c}$, —SR$^1$, —S(O)R$^{1a}$, —S(O)$_2$R$^{1a}$, —S(O)NR$^{1b}$R$^{1c}$, or —S(O)$_2$NR$^{1b}$R$^{1c}$.

Embodiment P4

The method of embodiment P3, wherein R$^{5a}$ and R$^{5b}$ are each methyl, optionally substituted with one, two, or three halo(s).

Embodiment P5

The method of any one of embodiments P1-P4, wherein n is 1.

Embodiment P6

The method of any one of embodiments P1-P5, wherein R$^{5f}$ and R$^{5g}$ are each hydrogen.

Embodiment P7

The method of any one of embodiments P1-P4, wherein n is 0.

Embodiment P8

The method of any one of embodiments P1-P7, wherein m is 0.

Embodiment P9

The method of any one of embodiments P1-P8, wherein the compound of Formula (I) is of Formula (XI):

Formula (XI)

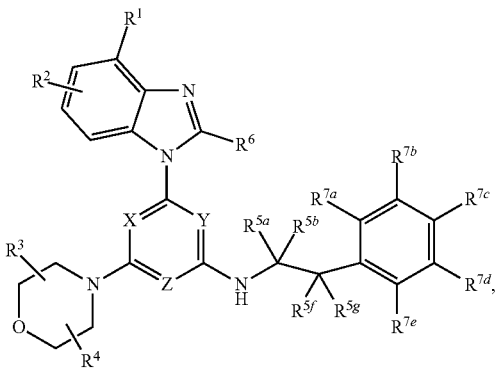

or an enantiomer, a mixture of enantiomers, a mixture of two or more diastereomers, or an isotopic variant thereof; or a pharmaceutically acceptable salt, solvate, hydrate, or prodrug thereof; wherein:

$R^{7a}$, $R^{7b}$, $R^{7c}$, $R^{7d}$, and $R^{7e}$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one, two, three, or four substituents $Q^a$; or (c) —C(O)$R^a$, —C(O)O$R^a$, —C(O)NR$^b$R$^c$, —C(NR$^a$)NR$^b$R$^c$, —O$R^a$, —OC(O)$R^a$, —OC(O)O$R^a$, —OC(O)NR$^b$R$^c$, —OC(=NR$^a$)NR$^b$R$^c$, —OS(O)$R^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —S$R^a$, —S(O)$R^a$, —S(O)$_2$R$^a$, —S(O)NR$^b$R$^c$, or —S(O)$_2$NR$^b$R$^c$; or two of $R^{7a}$, $R^{7b}$, $R^{7c}$, $R^{7d}$, and $R^{7e}$ that are adjacent to each other form $C_{3-10}$ cycloalkenyl, $C_{6-14}$ aryl, heteroaryl, or heterocyclyl, each optionally substituted with one, two, three, or four substituents $Q^a$.

Embodiment P10

The method of any one of embodiments P1-P9, wherein the compound of Formula (I) is Compound I:

Compound I

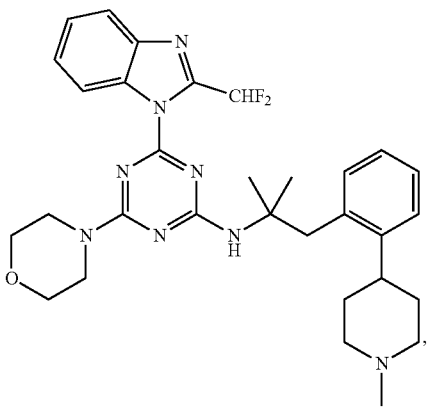

or an isotopic variant thereof, or a pharmaceutically acceptable salt, solvate, hydrate, or prodrug thereof.

Embodiment P11

The method of any one of embodiments P1-P10, wherein the PD-1 or PD-L1 inhibitor is pidilizumab, nivolumab, pembrolizumab, atezolizumab, avelumab, BMS-936559, BGB-A317, PDR001, REGN2810, or durvalumab, or a variant or biosimilar thereof, or combinations thereof.

Embodiment P12

The method of embodiment P11, wherein the PD-1 or PD-L1 inhibitor is pidilizumab, or a variant or biosimilar thereof.

Embodiment P13

The method of embodiment P11, wherein the PD-1 or PD-L1 inhibitor is nivolumab, or a variant or biosimilar thereof.

Embodiment P14

The method of embodiment P11, wherein the PD-1 or PD-L1 inhibitor is pembrolizumab, or a variant or biosimilar thereof.

Embodiment P15

The method of embodiment P11, wherein the PD-1 or PD-L1 inhibitor is atezolizumab, or a variant or biosimilar thereof.

Embodiment P16

The method of embodiment P11, wherein the PD-1 or PD-L1 inhibitor is BMS-936559, or a variant or biosimilar thereof.

Embodiment P17

The method of embodiment P11, wherein the PD-1 or PD-L1 inhibitor is durvalumab, or a variant or biosimilar thereof.

Embodiment P18

The method of embodiment P11, wherein the PD-1 or PD-L1 inhibitor is BGB-A317, or a variant or biosimilar thereof.

Embodiment P19

The method of embodiment P11, wherein the PD-1 or PD-L1 inhibitor is PDR001, or a variant or biosimilar thereof.

Embodiment P20

The method of embodiment P11, wherein the PD-1 or PD-L1 inhibitor is REGN2810, or a variant or biosimilar thereof.

Embodiment P21

The method of any one of embodiments P1-P20, wherein the cancer is non-Hodgkin's lymphoma, non-small cell lung cancer, melanoma, renal cell cancer, head and neck cancer, colon cancer, or mesothelioma.

Embodiment P22

The method of any one of embodiments P1-P21, wherein the cancer is melanoma.

Embodiment P23

The method of any one of embodiments P1-P22, wherein the administration of compounds occurs in one or more cycles.

Embodiment P24

A method for multiple cycle chemotherapy in a subject, wherein the method comprises administering to the subject at least two chemotherapy cycles, wherein in each chemotherapy cycle, a PI3K inhibitor and a PD-1 or PD-L1 inhibitor is administered to the subject.

Embodiment P25

The method of embodiment 24, wherein the compounds are administered within 6 hours or less of each other.

Embodiment P26

The method of either of embodiments P24 or P25, wherein the compounds are administered within 1 hour or less of each other.

Embodiment P27

The method of any one of embodiments P24-P26, wherein the compounds are administered simultaneously.

Embodiment P28

The method of any one of embodiments P24-P26, wherein the compounds are administered sequentially.

Embodiment P29

The method of any one of embodiments P24-P28, wherein the PI3K inhibitor is administered orally and the PD-1 or PD-L1 inhibitor is administered by injection.

Embodiment P30

The method of any one of embodiments P24-P29, wherein the administration of the second cycle is within 50 days.

Embodiment P31

The method of any one of embodiments P24-P29, wherein the administration of any additional cycle is within 50 days of the previous cycle.

Further embodiments include embodiments 1 to 42 following.

Embodiment 1

A method for treating or preventing cancer, comprising administering:

(i) an effective amount of a compound of Formula (I);

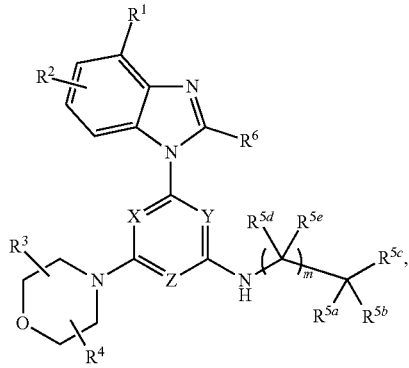

Formula (I)

or an enantiomer, a mixture of enantiomers, a mixture of two or more diastereomers, or an isotopic variant thereof; or a pharmaceutically acceptable salt, solvate, hydrate, or prodrug thereof; wherein:

X, Y, and Z are each independently N or $CR^X$, with the proviso that at least two of X, Y, and Z are nitrogen atoms; where $R^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$S(O)R^{1a}$, —$S(O)_2R^{1a}$, —$S(O)NR^{1b}R^{1c}$, or —$S(O)_2NR^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(C)NR^{1b}R^{1c}$, or —$S(O)_2NR^{1b}R^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —$C(O)R^{1a}$, —$C(O)OR^{1a}$, —$C(O)NR^{1b}R^{1c}$, —$C(NR^{1a})NR^{1b}R^{1c}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C (O)OR$^{1d}$, —NR$^{1a}$C(O)NR$^{1b}$R$^{1c}$, —NR$^{1a}$C(=NR$^{1a}$)NR$^{1b}$R$^{1c}$, —NR$^{1a}$S(O)R$^{1d}$, —NR$^{1a}$S(O)$_2$R$^{1d}$, —NR$^{1a}$S(C)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5c}$ is —(CR$^{5f}$R$^{5g}$)$_n$—(C$_{6-14}$ aryl) or —(CR$^{5f}$R$^{5g}$)$_n$-heteroaryl;

R$^{5d}$ and R$^{5e}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5f}$ and R$^{5g}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$; or —S(O)$_2$NR$^{1b}$R$^{1c}$; or (d) when one occurrence of R$^{5f}$ and one occurrence of R$^{5g}$ are attached to the same carbon atom, the R$^{5f}$ and R$^{5g}$ together with the carbon atom to which they are attached form a C$_{3-10}$ cycloalkyl or heterocyclyl;

R$^6$ is hydrogen, C$_{1-6}$ alkyl, —S—C$_{1-6}$ alkyl, —S(O)—C$_{1-6}$ alkyl, or —SO$_2$—C$_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl in R$^1$, R$^2$, R$^3$, R$^4$, R$^6$, R$^X$, R$^{1a}$, R$^{1b}$, R$^{1c}$, R$^{1d}$, R$^{5a}$, R$^{5b}$, R$^{5c}$, R$^{5d}$, R$^{5e}$, R$^{5f}$, and R$^{5g}$ is optionally substituted with one, two, three, four, or five substituents Q, wherein each substituent Q is independently selected from (a) oxo, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl, each of which is further optionally substituted with one, two, three, or four substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is further optionally substituted with one, two, three, or four substituents Q$^a$; or (iii) R$^b$ and R$^c$ together with the N atom to which they are attached form heterocyclyl, which is further optionally substituted with one, two, three, or four substituents Q$^a$;

wherein each Q$^a$ is independently selected from the group consisting of (a) oxo, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl; or wherein two substituents Q that are adjacent to each other optionally form a C$_{3-10}$ cycloalkenyl, C$_{6-14}$ aryl, heteroaryl, or heterocyclyl, each optionally substituted with one, two, three, or four substituents Q$^a$; and (ii) an effective amount of a PD-1 or PD-L1 inhibitor.

Embodiment 2

The method of embodiment 1, wherein R$^{5b}$ is (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, or heteroaryl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —S(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

Embodiment 3

The method of embodiment 1, wherein R$^{5a}$ and R$^{5b}$ are each independently (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1a}$)NR$^{1b}$R$^{1c}$, —NR$^{1a}$S(O)R$^{1d}$, —NR$^{1a}$S(O)$_2$R$^{1d}$, —NR$^{1a}$S(C)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

Embodiment 4

The method of embodiment 3, wherein R$^{5a}$ and R$^{5b}$ are each methyl, optionally substituted with one, two, or three halo(s).

Embodiment 5

The method of any one of embodiments 1-4, wherein n is 1.

Embodiment 6

The method of any one of embodiments 1-5, wherein $R^{5f}$ and $R^{5g}$ are each hydrogen.

Embodiment 7

The method of any one of embodiments 1-4, wherein n is 0.

Embodiment 8

The method of any one of embodiments 1-7, wherein m is 0.

Embodiment 9

The method of any one of embodiments 1-6 or 8, wherein the compound of Formula (I) is of Formula (XI):

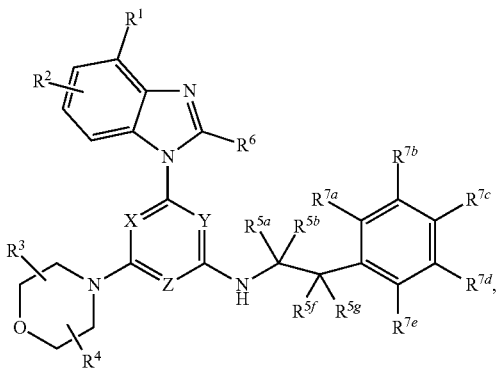

Formula (XI)

or an enantiomer, a mixture of enantiomers, a mixture of two or more diastereomers, or an isotopic variant thereof; or a pharmaceutically acceptable salt, solvate, hydrate, or prodrug thereof; wherein:

$R^{7a}$, $R^{7b}$, $R^{7c}$, $R^{7d}$, and $R^{7e}$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one, two, three, or four substituents $Q^a$; or (c) —C(O)$R^a$, —C(O)O$R^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, or —S(O)$_2$NR$^b$R$^c$; or two of $R^{7a}$, $R^{7b}$, $R^{7c}$, $R^{7d}$, and $R^{7e}$ that are adjacent to each other form $C_{3-10}$ cycloalkenyl, $C_{6-14}$ aryl, heteroaryl, or heterocyclyl, each optionally substituted with one, two, three, or four substituents $Q^a$.

Embodiment 10

The method of any one of embodiments 1-9, wherein the compound of Formula (I) is Compound I:

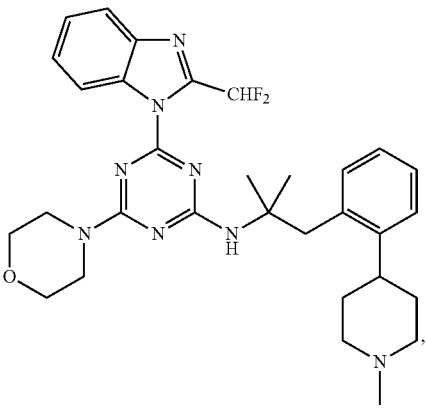

Compound I or an isotopic variant thereof, or a pharmaceutically acceptable salt, solvate, hydrate, or prodrug thereof.

Embodiment 11

The method of any one of embodiments 1-9, wherein the compound of Formula (I) is Compound II:

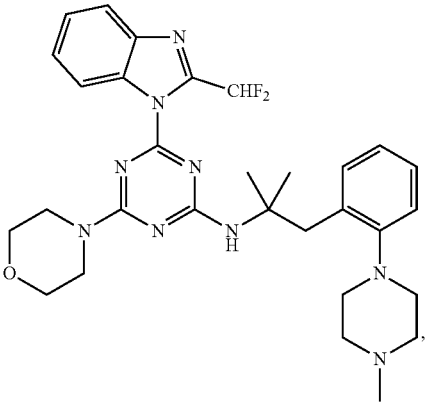

Compound II or an isotopic variant thereof, or a pharmaceutically acceptable salt, solvate, hydrate, or prodrug thereof.

Embodiment 12

The method of any one of embodiments 1-9, wherein the compound of Formula (I) is Compound III:

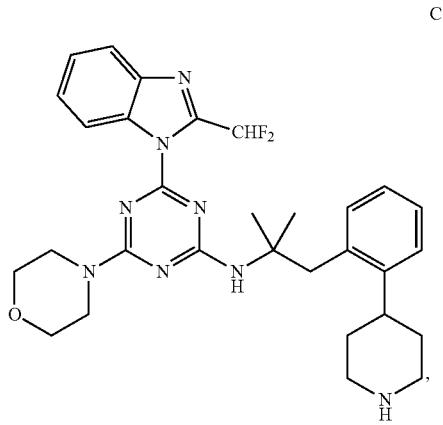

Compound III or an isotopic variant thereof, or a pharmaceutically acceptable salt, solvate, hydrate, or prodrug thereof.

Embodiment 13

The method of any one of embodiments 1-9, wherein the compound of Formula (I) is Compound IV:

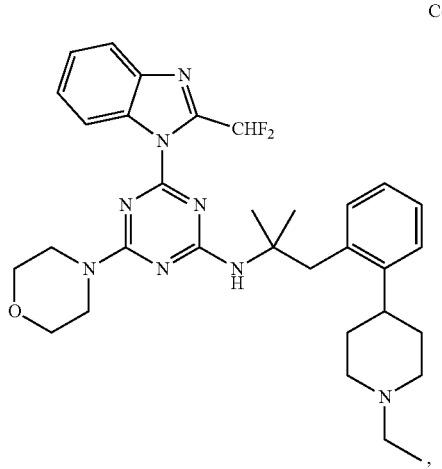

Compound IV or an isotopic variant thereof, or a pharmaceutically acceptable salt, solvate, hydrate, or prodrug thereof.

Embodiment 14

The method of any one of embodiments 1-9, wherein the compound of Formula (I) is Compound V:

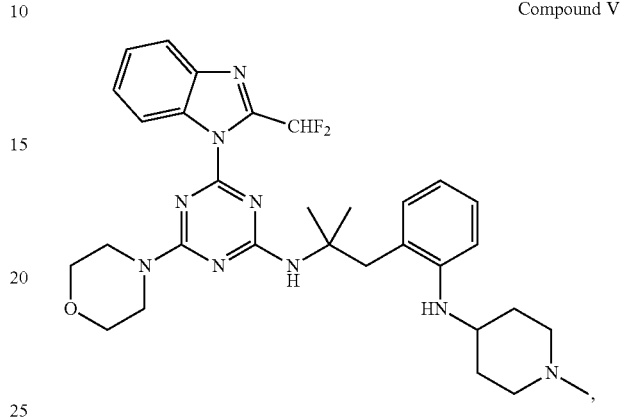

Compound V or an isotopic variant thereof, or a pharmaceutically acceptable salt, solvate, hydrate, or prodrug thereof.

Embodiment 15

The method of any one of embodiments 1-9, wherein the compound of Formula (I) is Compound VI:

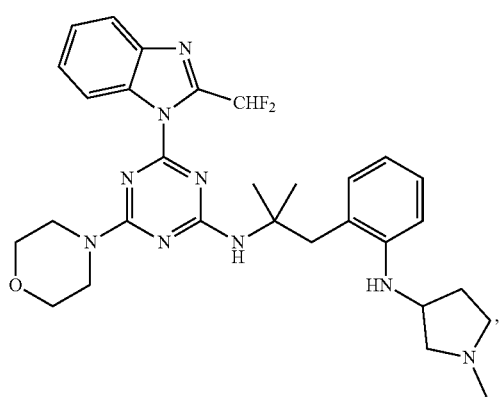

Compound VI or an isotopic variant thereof, or a pharmaceutically acceptable salt, solvate, hydrate, or prodrug thereof.

Embodiment 16

The method of any one of embodiments 1-9, wherein the compound of Formula (I) is Compound VII:

Compound VII

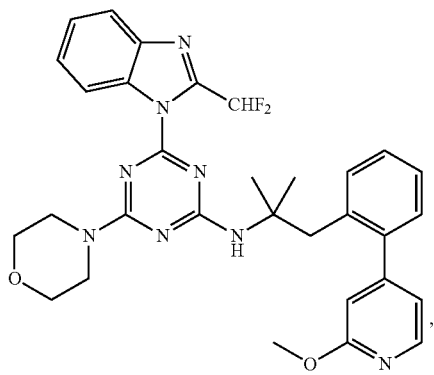

or an isotopic variant thereof, or a pharmaceutically acceptable salt, solvate, hydrate, or prodrug thereof.

Embodiment 17

The method of any one of embodiments 1-9, wherein the compound of Formula (I) is Compound VIII:

Compound VIII

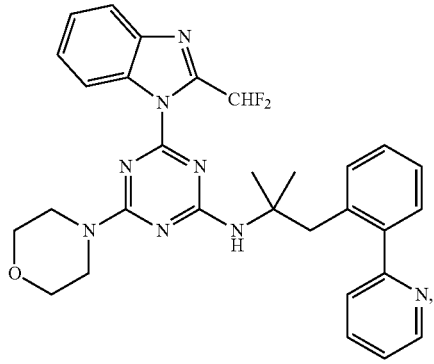

or an isotopic variant thereof, or a pharmaceutically acceptable salt, solvate, hydrate, or prodrug thereof.

Embodiment 18

The method of any one of embodiments 1-9, wherein the compound of Formula (I) is Compound IX:

Compound IX

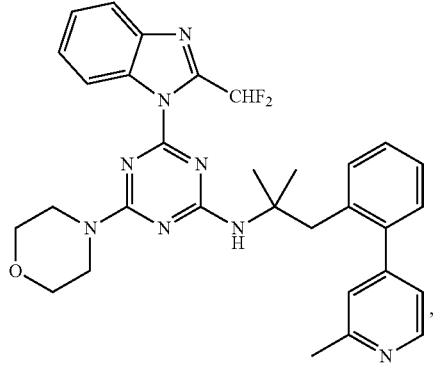

or an isotopic variant thereof, or a pharmaceutically acceptable salt, solvate, hydrate, or prodrug thereof.

Embodiment 19

The method of any one of embodiments 1-9, wherein the compound of Formula (I) is Compound X:

Compound X

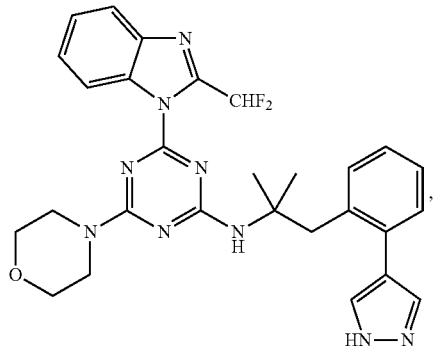

or an isotopic variant thereof, or a pharmaceutically acceptable salt, solvate, hydrate, or prodrug thereof.

Embodiment 20

The method of any one of embodiments 1-19, wherein the PD-1 or PD-L1 inhibitor is pidilizumab, nivolumab, pembrolizumab, atezolizumab, avelumab, BMS-936559, BGB-A317, PDR001, REGN2810, or durvalumab, or a variant or biosimilar thereof, or combinations thereof.

Embodiment 21

The method of embodiment 20, wherein the PD-1 or PD-L1 inhibitor is pidilizumab, or a variant or biosimilar thereof.

Embodiment 22

The method of embodiment 20, wherein the PD-1 or PD-L1 inhibitor is nivolumab, or a variant or biosimilar thereof.

Embodiment 23

The method of embodiment 20, wherein the PD-1 or PD-L1 inhibitor is pembrolizumab, or a variant or biosimilar thereof.

Embodiment 24

The method of embodiment 20, wherein the PD-1 or PD-L1 inhibitor is atezolizumab, or a variant or biosimilar thereof.

Embodiment 25

The method of embodiment 20, wherein the PD-1 or PD-L1 inhibitor is BMS-936559, or a variant or biosimilar thereof.

Embodiment 26

The method of embodiment 20, wherein the PD-1 or PD-L1 inhibitor is durvalumab, or a variant or biosimilar thereof.

Embodiment 27

The method of embodiment 20, wherein the PD-1 or PD-L1 inhibitor is BGB-A317, or a variant or biosimilar thereof.

Embodiment 28

The method of embodiment 20, wherein the PD-1 or PD-L1 inhibitor is PDR001, or a variant or biosimilar thereof.

Embodiment 29

The method of embodiment 20, wherein the PD-1 or PD-L1 inhibitor is REGN2810, or a variant or biosimilar thereof.

Embodiment 30

The method of any one of embodiments 1-29, wherein the cancer is non-Hodgkin's lymphoma, non-small cell lung cancer, melanoma, renal cell cancer, head and neck cancer, colon cancer, or mesothelioma.

Embodiment 31

The method of any one of embodiments 1-30, wherein the cancer is melanoma.

Embodiment 32

The method of any one of embodiments 1-31, wherein the administration of compounds occurs in one or more cycles.

Embodiment 33

A method for multiple cycle chemotherapy in a subject, wherein the method comprises administering to the subject at least two chemotherapy cycles, wherein in each chemotherapy cycle, a PI3K inhibitor and a PD-1 or PD-L1 inhibitor are administered to the subject.

Embodiment 34

The method of embodiment 33, wherein the compounds are administered within 6 hours or less of each other.

Embodiment 35

The method of either of embodiments 33 or 34, wherein the compounds are administered within 1 hour or less of each other.

Embodiment 36

The method of any one of embodiments 33-35, wherein the compounds are administered simultaneously.

Embodiment 37

The method of any one of embodiments 33-35, wherein the compounds are administered sequentially.

Embodiment 38

The method of any one of embodiments 33-35 or 37, wherein the PI3K inhibitor is administered before the PD-1 or PD-L1 inhibitor.

Embodiment 39

The method of of any one of embodiments 33-35 or 37, wherein the PI3K inhibitor is administered after the PD-1 or PD-L1 inhibitor.

Embodiment 40

The method of any one of embodiments 33-39, wherein the PI3K inhibitor is administered orally and the PD-1 or PD-L1 inhibitor is administered by injection.

Embodiment 41

The method of any one of embodiments 33-40, wherein the administration of a second cycle is within 50 days of completion of a first cycle.

Embodiment 42

The method of any one of embodiments 33-40, wherein the administration of any additional cycle is within 50 days of completion of a previous cycle.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL, (microliters); M (molar); mM (millimolar), µM (micro molar); eq. (equivalent);

mmol (millimoles), Hz (Hertz), MHz (megahertz); hr or hrs (hour or hours); min (minutes); and MS (mass spectrometry).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies illustrated herein are intended to exemplify the applicable chemistry through the use of specific examples and are not indicative of the scope of the disclosure.

Synthesis of Compound I is described in U.S. Pat. No. 9,056,852 B2, which is incorporated by reference for such disclosure.

Example 1: Synthesis of 4-(2-(difluoromethyl)-1H-benzo[d]imidazol-1-yl)-N-(2-methyl-1-(2-(1-methylpiperidin-4-yl)phenyl)propan-2-yl)-6-morpholino-1,3,5-triazin-2-amine, Compound I A mixture of 4-(2-(difluoromethyl)-1H-benzo[d]imidazol-1-yl)-N-(2-methyl-1-(2-(piperidin-4-yl)phenyl)propan-2-yl)-6-morpholino-1,3,5-triazin-2-amine (80 mg, 0.14 mmol), aq. formaldehyde (37%, 23 mg), and sodium cyanoborohydride (11 mg, 0.17 mmol) in methanol (2 mL) was stirred at room temperature for 1 hr. The crude product was purified by prep-HPLC to give compound I (11 mg, 13% yield) as a white solid: 99% purity (HPLC); MS m/z: 577.3 (M+1); $^1$H NMR (CDCl$_3$, 500 MHz) δ 8.37 (d, 1H), 7.90 (d, 1H), 7.64 (t, 1H), 7.42 (m, 2H), 7.32 (d, 1H), 7.24 (1, 1H), 7.13 (t, 1H), 7.07 (d, 1H), 5.15 (s, 1H), 4.00-3.70 (m, 8H), 3.28 (s, 2H), 2.94 (m, 2H), 2.78 (m, 2H), 2.28 (s, 3H), 1.89-1.60 (m, 6H), 1.53 (s, 6H) ppm.

Example 2: MC38 Murine Colon Carcinoma Model for Combination of PI3K Inhibitor and PD-1 Inhibitor The combination of a PI3K inhibitor (Compound I) and a PD-1 inhibitor (RPM1-14) was evaluated utilizing a MC38 murine colon carcinoma syngeneic model in female immunocompetent C57BL/6 mice. The study was designed to plot the survival time of murine specimens when treated with the combination of Compound I and the PD-1 inhibitor.

Compound I dosing solutions were prepared weekly. Formulations of Compound I were prepared by adding the appropriate amount of 20% VE-TPGS, 80% 100 mM citrate buffer, pH 3.5 solution (vehicle) to Compound I. The resulting suspension was stirred overnight to yield a 5 mg/mL dose solution. This solution provided a dosage of 50 mg/kg in a dosing volume of 10 mL/kg. The Compound I dosing solution was stored at 4° C. when not in use.

The PD-1 inhibitor (anti-PD-1 antibody Clone RMP1-14, Lot No. 5792-599016J1) was purchased by CR Discovery Services from Bio X Cell and stored at 4° C. upon receipt. Anti-PD-1 antibody dosing solutions were prepared by diluting aliquots of the stock (6.37 mg/mL) to 0.5 mg/mL in sterile PBS, yielding a dosage of 100 µg/animal in a fixed dosing volume of 0.2 mL/animal.

Tumors were measured twice weekly. Treatment response was to be evaluated from tumor growth delay (TGD), the increase in median time-to-endpoint (TTE) in treated versus control mice, and from comparison of survival curves using logrank analysis. Each animal was marked for tumor progression when its tumor reached the 1000 mm$^3$ volume endpoint, and any animal that did not reach the endpoint was euthanized at the end of the study and assigned a TTE value equal to the last day of the study (Day 45).

The median TTE for control Group 1 was 19.0 days, establishing a maximum TGD of 137% for this study. All treatments evaluated in the study were acceptably-tolerated, with acceptable mean BW losses and no treatment-related (TR) deaths.

Tumor Growth Delay (TGD) Analysis

Animals were monitored individually for tumor growth until Day 45. The study protocol specified a tumor growth delay assay based on the median time to endpoint (TTE) in a treated group versus the control group. Each animal was marked for tumor progression (TP) when its tumor reached the 1000 mm3 volume endpoint. The TTE for each mouse was calculated with the following equation:

$$TTE = \frac{\log_{10}(\text{endpoint volume}) - b}{m}$$

where b is the intercept and m is the slope of the line obtained by linear regression of a log-transformed tumor growth data set. The data set is comprised of the first observation that exceeded the study endpoint volume and the three consecutive observations that immediately preceded the attainment of the endpoint volume. Any animal that did not reach endpoint was euthanized at the end of the study and assigned a TTE value equal to the last day of the study (Day 45). In instances in which the log-transformed calculated TTE preceded the day prior to reaching endpoint or exceeded the day of reaching tumor volume endpoint, a linear interpolation was performed to approximate TTE.

On Day 45, MTV (n) was defined as the median tumor volume of the number of animals, n, that survived to the last day and whose tumors had not reached the volume endpoint. Any animal determined to have died from TR causes was to be assigned a TTE value equal to the day of death. Any animal that died from NTR causes was to be excluded from the analysis. Treatment outcome was evaluated from TGD, which was defined as the increase in the median TTE for a treatment group compared to the control group:

TGD=T−C expressed in days, or as a percentage of the median TTE of the control group:

$$\% \; TGD = \frac{T-C}{C} \times 100$$

where
T=median TTE for a treatment group,
C=median TTE for the control group.

Survival was analyzed by the Kaplan-Meier method. The logrank (Mantel-Cox) and Gehan-Breslow-Wilcoxon tests determined the significance of the difference between the overall survival experiences (survival curves) of two groups, based on TTE values. A scatter plot was constructed to show TTE values for individual mice, by group. Group median tumor volumes were plotted as functions of time. When an animal exited the study because of tumor size, the final tumor volume recorded for the animal was included with the data used to calculate the median volume at subsequent time points. A Kaplan-Meier plot was constructed to show the percentage of animals in each group remaining on study versus time.

Example 2a

On Day 1 of the study, four groups of C57BL/6 mice (n=10 for control group and PD-1 monotherapy; n=20 for combination therapy) began dosing. Compound I was administered by oral gavage (p.o.) at a dosage of 50 mg/kg in a dosing volume of 10 mL/kg and was adjusted according to the most recent body weight measurement. The PD-1 inhibitor was administered intraperitoneally (i.p.) at a dosage of 100 μg/animal in a fixed dosing volume of 0.2 mL/animal.

Group 1 was left untreated and served as the control group for the % TGD.

Group 2 was treated with the PD-1 inhibitor i.p. at a dosage of 100 μg/animal twice weekly for two weeks.

Group 3 received Compound I p.o. at 50 mg/kg qd×7 starting on Day 1. Beginning on Day 8, this group was then treated with the PD-1 inhibitor i.p. at 100 μg/animal biwk×2.

Group 4 received Compound I p.o. at 50 mg/kg qd×7 starting on Day 1. Beginning on Day 8, this group was treated with the PD-1 inhibitor i.p. at 100 μg/animal biwk×2 with the final dose occurring on Day 18. On Day 22, treatment with Compound I resumed at 50 mg/kg once daily for five days (qd×5, start Day 22).

Group 5 received Compound I p.o. at 50 mg/kg qd×7 starting on Day 1. On Day 8, these animals received the PD-1 inhibitor i.p. at 100 μg/animal biwk×2 with the final dose occurring on Day 18. A second course of the PD-1 inhibitor was administered biwk×2 beginning on Day 27.

Group 6 received Compound I p.o. at 50 mg/kg qd×7 starting on Day 1. On Day 8, these animals received the PD-1 inhibitor i.p. at 100 μg/animal biwk×2 with the final dose occurring on Day 18. On Day 22, treatment with Compound I resumed at 50 mg/kg qd×5. A second course of the PD-1 inhibitor was administered biwk×2 beginning on Day 27.

Treatment with Compound I and the PD-1 inhibitor was well-tolerated. All of the Compound I/PD-1 inhibitor combinations provided statistically significant survival benefits. Combination regimens that administered Compound I and the PD-1 inhibitor in two chemotherapy cycles were more effective than one chemotherapy cycle (Group 6 vs Group 3) and more effective than a single cycle of the PD-1 inhibitor (Group 6 vs Group 2). The results are depicted in FIG. 1.

Figure 2:
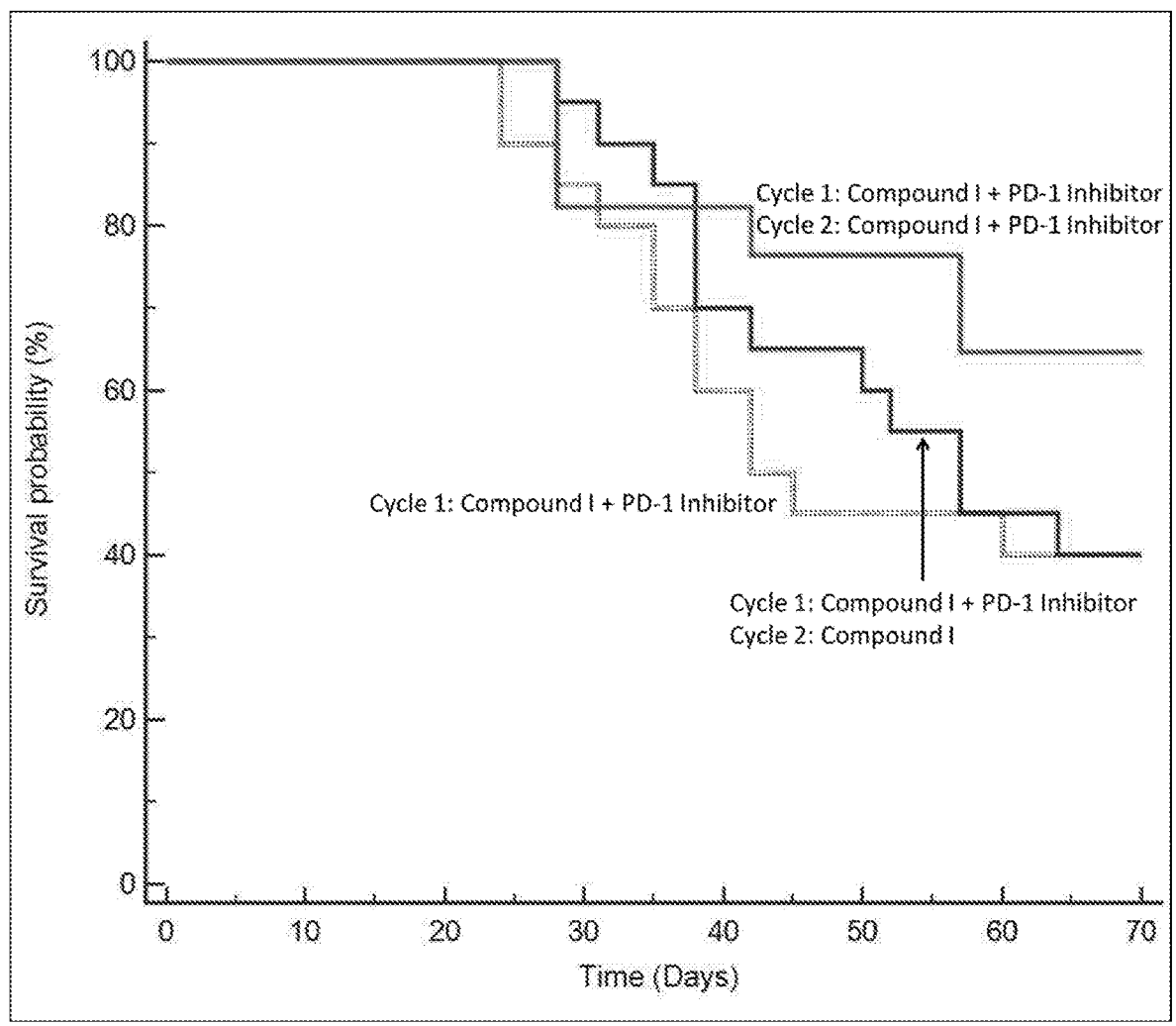
FIG. 2 illustrates the Kaplan-Meier survival curves obtained from Example 2a, wherein a study was performed evaluating the efficacy of a combination treatment of Compound I and the PD-1 inhibitor (RPM1-14) in a MC38 murine adenocarcinoma model. The figure depicts the efficacy of two cycles of the combination treatment in comparison to a single cycle of a combination treatment or a single cycle of the combination with an additional cycle of Compound I.

Combination regimens that administered Compound I and the PD-1 inhibitor in two chemotherapy cycles were more effective than the administration of one combination cycle and one Compound I cycle (Group 6 vs Group 4) and more effective than the administration of a single cycle of a combination treatment with Compound I and the PD-1 inhibitor. (Group 6 vs Group 3). The results are depicted in FIG. 2.

Figure 3:
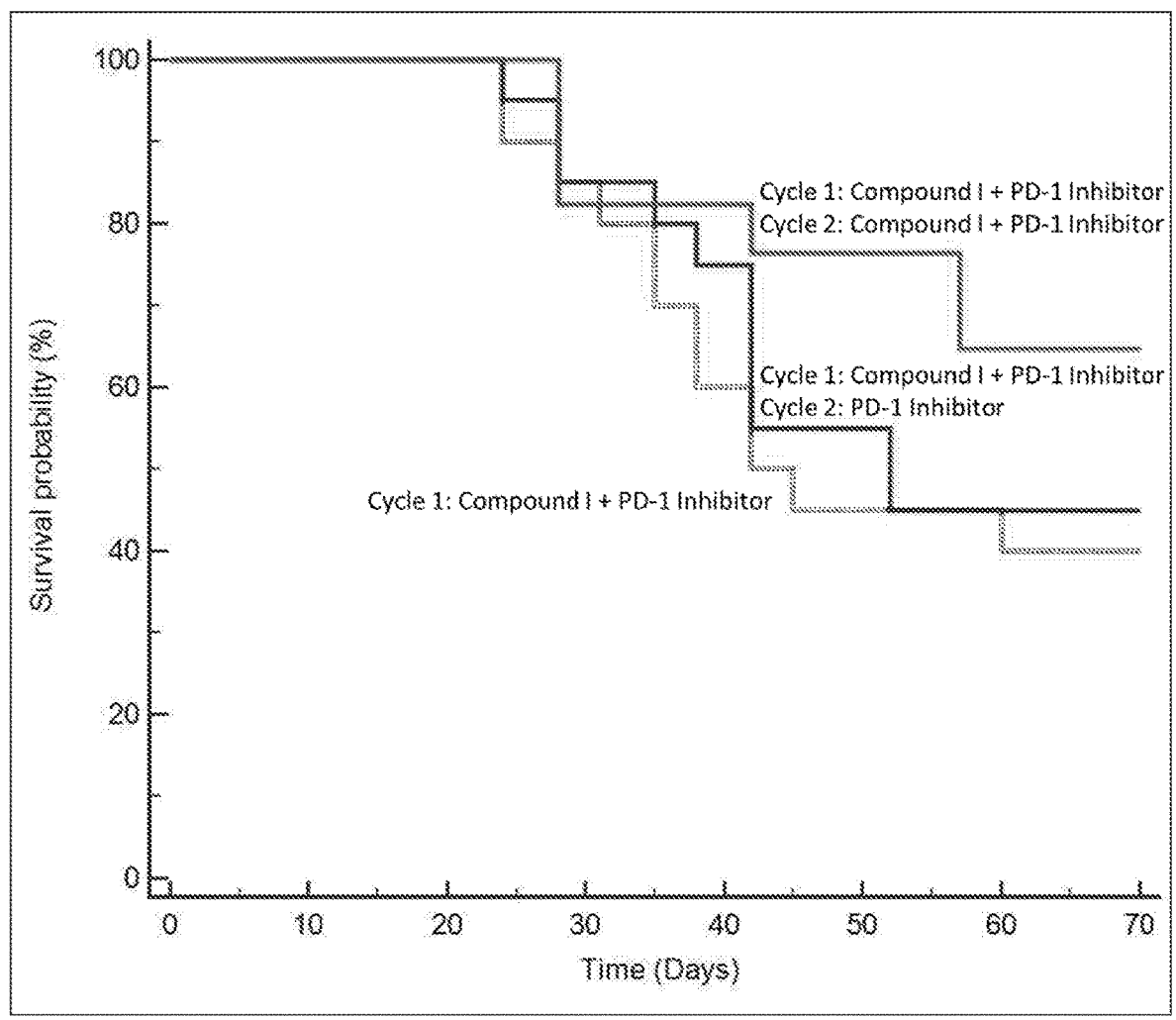
FIG. 3 illustrates the Kaplan-Meier survival curves obtained from Example 2a, wherein a study was performed evaluating the efficacy of a combination treatment of Compound I and the PD-1 inhibitor (RPM1-14) in a MC38 murine adenocarcinoma model. The figure depicts the efficacy of two cycles of the combination treatment in comparison to a single cycle of a combination treatment or a single cycle of the combination with an additional cycle of the PD-1 inhibitor.

Combination regimens that administered Compound I and the PD-1 inhibitor in two chemotherapy cycles were more effective than the administration one combination cycle and one PD-1 inhibitor cycle (Group 6 vs Group 5) and more effective than the administration of a single cycle of a combination treatment with Compound I and the PD-1 inhibitor. (Group 6 vs Group 3). The results are depicted in FIG. 3.

What is claimed is:
1. A method for treating a non-Hodgkin's lymphoma, non-small cell lung cancer, melanoma, renal cell cancer, head and neck cancer, colon cancer, mesothelioma, comprising administering:
(i) an effective amount of a compound of Formula (I);

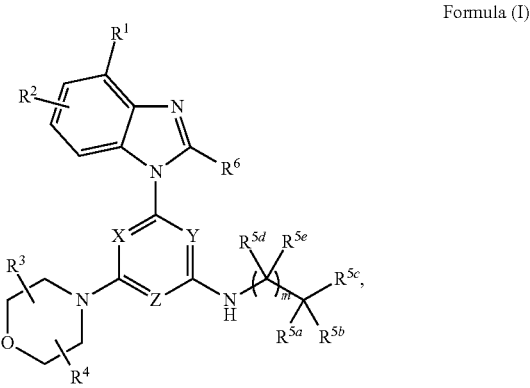

Formula (I)

or an enantiomer, a mixture of enantiomers, a mixture of two or more diastereomers, or an isotopic variant thereof; or a pharmaceutically acceptable salt, solvate, hydrate, or prodrug thereof; wherein:

X, Y, and Z are each independently N or $CR^x$, with the proviso that at least two of X, Y, and Z are nitrogen atoms; where $R^x$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5c}$ is —(CR$^{5f}$R$^{5g}$)$_n$—(C$_{6-14}$ aryl) or —(CR$^{5f}$R$^{5g}$)$_n$-heteroaryl;

R$^{5d}$ and R$^{5e}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{5f}$ and R$^{5g}$ are each independently (a) hydrogen or halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$; or —S(O)$_2$NR$^{1b}$R$^{1c}$; or (d) when one occurrence of R$^{5f}$ and one occurrence of R$^{5g}$ are attached to the same carbon atom, the R$^{5f}$ and R$^{5g}$ together with the carbon atom to which they are attached form a C$_{3-10}$ cycloalkyl or heterocyclyl;

R$^6$ is hydrogen, C$_{1-6}$ alkyl, —S—C$_{1-6}$ alkyl, —S(O)—C$_{1-6}$ alkyl, or —SO$_2$—C$_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl in R$^1$, R$^2$, R$^3$, R$^4$, R$^6$, R$^X$, R$^{1a}$, R$^{1b}$, R$^{1c}$, R$^{1d}$, R$^{5a}$, R$^{5b}$, R$^{5c}$, R$^{5d}$, R$^{5e}$, R$^{5f}$, and R$^{5g}$ is optionally substituted with one, two, three, four, or five substituents Q, wherein each substituent Q is independently selected from (a) oxo, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl, each of which is further optionally substituted with one, two, three, or four substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is further optionally substituted with one, two, three, or four substituents Q$^a$; or (iii) R$^b$ and R$^c$ together with the N atom to which they are attached form heterocyclyl, which is further optionally substituted with one, two, three, or four substituents Q$^a$;

wherein each Q$^a$ is independently selected from the group consisting of (a) oxo, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl; or wherein two substituents Q that are adjacent to each other optionally form a C$_{3-10}$ cycloalkenyl, C$_{6-14}$ aryl, heteroaryl, or heterocyclyl, each optionally substituted with one, two, three, or four substituents Q$^a$;

and (ii) an effective amount of a PD-1 or PD-L1 inhibitor.

2. The method of claim 1, wherein R$^{5b}$ is (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, or heteroaryl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —S(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

3. The method of claim 1, wherein R$^{5a}$ and R$^{5b}$ are each independently (a) halo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

4. The method of claim 3, wherein R$^{5a}$ and R$^{5b}$ are each methyl, optionally substituted with one, two, or three halo(s).

5. The method of claim 1, wherein n is 1, m is 0, and R$^{5f}$ and R$^{5g}$ are each hydrogen.

6. The method of claim 1, wherein the compound of Formula (I) is of Formula (XI):

Formula (XI)

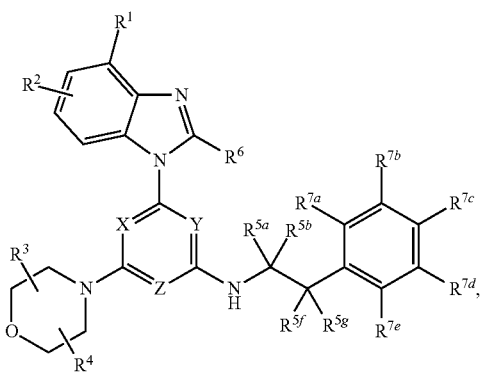

or an enantiomer, a mixture of enantiomers, a mixture of two or more diastereomers, or an isotopic variant thereof; or a pharmaceutically acceptable salt, solvate, hydrate, or prodrug thereof; wherein:

$R^{7a}$, $R^{7b}$, $R^{7c}$, $R^{7d}$, and $R^{7e}$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one, two, three, or four substituents $Q^a$; or (c) —C(O)$R^a$, —C(O)O$R^a$, —C(O)N$R^b R^c$, —C(N$R^a$)N$R^b R^c$, —O$R^a$, —OC(O)$R^a$, —OC(O)O$R^a$, —OC(O)N$R^b R^c$, —OC(=N$R^a$)N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(=N$R^d$)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —S$R^a$, —S(O)$R^a$, —S(O)$_2 R^a$, —S(O)N$R^b R^c$, or —S(O)$_2$N$R^b R^c$; or two of $R^{7a}$, $R^{7b}$, $R^{7c}$, $R^{7d}$, and $R^{7e}$ that are adjacent to each other form $C_{3-10}$ cycloalkenyl, $C_{6-14}$ aryl, heteroaryl, or heterocyclyl, each optionally substituted with one, two, three, or four substituents $Q^a$.

7. The method of claim 1, wherein the compound of Formula (I) is Compound I:

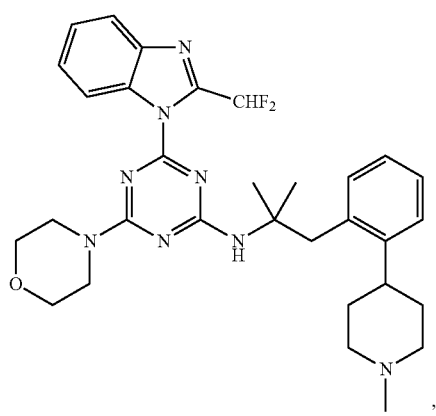

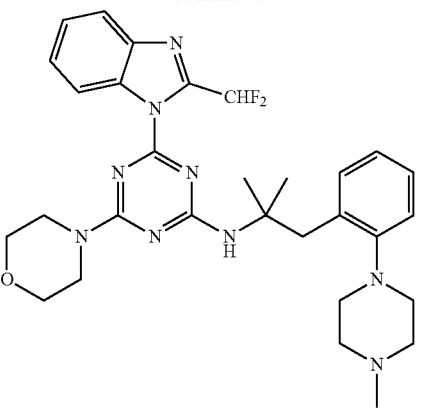

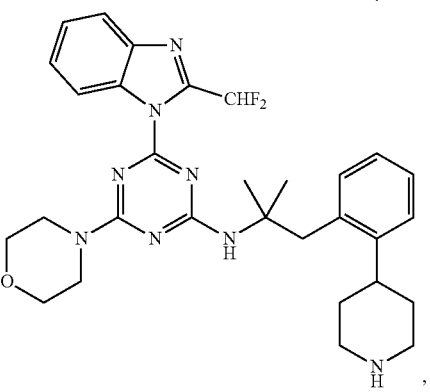

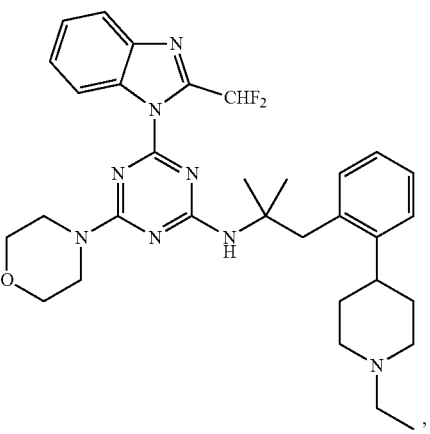

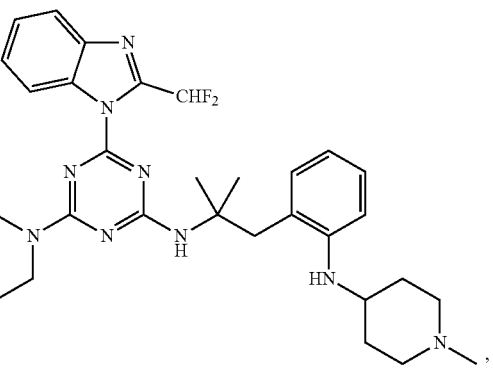

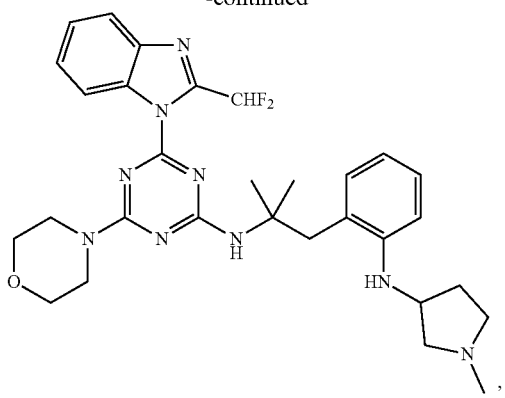

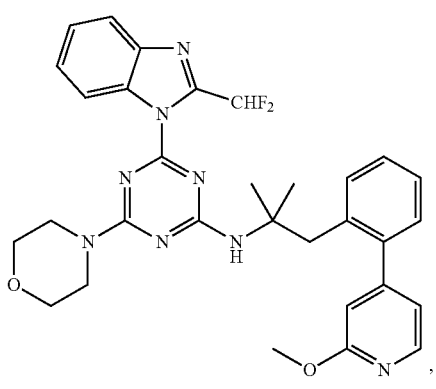

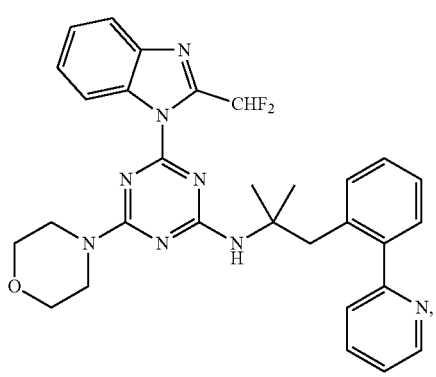

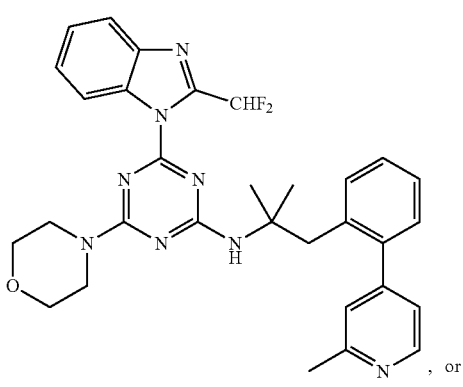

, or

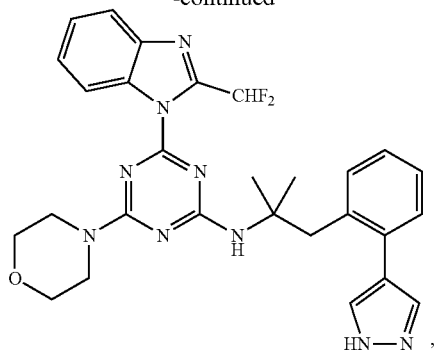

or an isotopic variant thereof, or a pharmaceutically acceptable salt, solvate, hydrate, or prodrug thereof.

8. The method of claim 1, wherein the compound of Formula (I) is Compound II:

Compound I

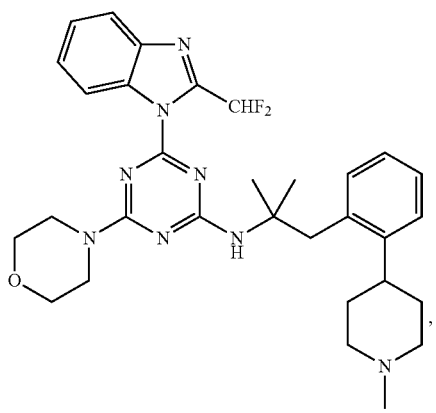

or an isotopic variant thereof, a pharmaceutically acceptable salt, solvate, hydrate, or prodrug thereof.

9. The method of claim 1, wherein the PD-1 or PD-L1 inhibitor is pidilizumab, nivolumab, pembrolizumab, atezolizumab, avelumab, BMS-936559, BGB-A317, PDR001, REGN2810, or durvalumab, or a variant or biosimilar thereof, or combinations thereof.

10. The method of claim 9, wherein the PD-1 or PD-L1 inhibitor is nivolumab, or a variant or biosimilar thereof.

11. The method of claim 9, wherein the PD-1 or PD-L1 inhibitor is atezolizumab, or a variant or biosimilar thereof.

12. The method of claim 1, wherein the cancer is melanoma.

13. The method of claim 1, wherein the administration of compounds occurs in one or more cycles.

14. A method for multiple cycle chemotherapy in a subject, wherein the method comprises administering to the subject at least two chemotherapy cycles, wherein in each chemotherapy cycle, a PI3K inhibitor and a PD-1 or PD-L1 inhibitor are administered to the subject.

15. The method of claim 14, wherein the compounds are administered within 6 hours or less of each other.

16. The method of claim 14, wherein the compounds are administered within 1 hour or less of each other.

17. The method of claim 14, wherein the compounds are administered simultaneously.

18. The method of claim 14, wherein the compounds are administered sequentially.

19. The method of claim 14, wherein the administration of any additional cycle is within 50 days of completion of a previous cycle.

* * * * *

UNITED STATES PATENT AND TRADEMARK OFFICE
CERTIFICATE OF CORRECTION

| | | |
|---|---|---|
| PATENT NO. | : 11,304,953 B2 | |
| APPLICATION NO. | : 16/613638 | |
| DATED | : April 19, 2022 | |
| INVENTOR(S) | : Daniel P. Gold | |

It is certified that error appears in the above-identified patent and that said Letters Patent is hereby corrected as shown below:

In the Claims

Column 131, Line 66: -- or -- should appear after colon cancer, and before mesothelioma.
Column 138, Line 20: "Compound II" should read: -- Compound I --.
Column 138, Line 49: -- pembrolizumab, or REGN2810, -- should appear after nivolumab.
Column 138, Line 51: -- avelumab, or durvalumab, -- should appear after atezolizumab.

Signed and Sealed this
Thirty-first Day of May, 2022

Katherine Kelly Vidal
*Director of the United States Patent and Trademark Office*